US007595306B2

(12) United States Patent
Bumcrot

(10) Patent No.: US 7,595,306 B2
(45) Date of Patent: Sep. 29, 2009

(54) METHOD OF TREATING NEURODEGENERATIVE DISEASE

(76) Inventor: David Bumcrot, 30 Leicester Rd., Belmont, MA (US) 02478

( * ) Notice: Subject to any disclaimer, the term of this patent is extended or adjusted under 35 U.S.C. 154(b) by 0 days.

(21) Appl. No.: 11/548,890

(22) Filed: Oct. 12, 2006

(65) Prior Publication Data

US 2007/0161595 A1 Jul. 12, 2007

Related U.S. Application Data

(63) Continuation-in-part of application No. 10/991,286, filed on Nov. 17, 2004, which is a continuation-in-part of application No. PCT/US2004/018271, filed on Jun. 9, 2004.

(60) Provisional application No. 60/476,947, filed on Jun. 9, 2003.

(51) Int. Cl.
*A61K 48/00* (2006.01)
*C07H 21/04* (2006.01)
*C07H 21/02* (2006.01)
*C12N 15/85* (2006.01)

(52) U.S. Cl. ............... 514/44; 536/23.1; 536/24.31; 536/24.5; 435/325

(58) Field of Classification Search .............. None
See application file for complete search history.

(56) References Cited

U.S. PATENT DOCUMENTS

| | | | |
|---|---|---|---|
| 5,328,470 A | 7/1994 | Nabel et al. | |
| 5,460,959 A | 10/1995 | Mulligan et al. | |
| 5,691,316 A | 11/1997 | Agrawal et al. | |
| 5,814,014 A | 9/1998 | Elsberry et al. | |
| 5,994,127 A | 11/1999 | Selden et al. | |
| 6,048,729 A | 4/2000 | Selden et al. | |
| 6,063,630 A | 5/2000 | Treco et al. | |
| 6,093,180 A | 7/2000 | Elsberry | |
| 6,107,094 A | 8/2000 | Crooke | |
| 6,534,261 B1 | 3/2003 | Cox, III et al. | |
| 6,590,323 B1 | 7/2003 | Stekelenburg | |
| 6,607,882 B1 | 8/2003 | Cox, III et al. | |
| 2002/0062419 A1 | 5/2002 | Konson et al. | |
| 2003/0008818 A1 | 1/2003 | Pun et al. | |
| 2003/0027322 A1 | 2/2003 | Federoff et al. | |
| 2003/0143732 A1 | 7/2003 | Fosnaugh et al. | |
| 2004/0219671 A1* | 11/2004 | McSwiggen et al. | ........ 435/375 |
| 2007/0031844 A1 | 2/2007 | Khvorova et al. | |

FOREIGN PATENT DOCUMENTS

| | | |
|---|---|---|
| AU | 2003/295600 A1 | 7/2005 |
| WO | WO 96/37194 | 11/1996 |
| WO | WO 00/44895 | 8/2000 |
| WO | WO 00/44914 | 8/2000 |
| WO | WO 01/36646 A1 | 5/2001 |
| WO | WO 2004/080406 | 9/2004 |
| WO | 2005097817 | 10/2005 |
| WO | WO 2005/097817 | 10/2005 |

OTHER PUBLICATIONS

During, et al. (1998) In vivo Expression of Therapeutic Human Genes for Dopamine Production in the Caudates of MPTP-Treated Monkeys Using an AAV Vector. Gene Therapy, v.5: 820-827.*
Altschul, et al. (1997) Gapped BLAST and PSI-PLAST: a New Generation of Protein Database Search Programs. Nucleic Acids Research, v.25(17):3389-3402.*
Ueda, et al. (1993) Molecular Cloning of cDNA Encoding an unrecognized component of Amyloid in Alzheimer Disease. PNAS, v.90:11282-11286.*
Savitt, et al. (2006) Diagnosis and Treatment of Parkinson Disease: Molecules to Medicine. J. Clin. Invest. v.116(7):1744-1754.*
Yuan, et al. (2004) siRNA Selection Server: an Automated siRNA Oligonucleotide Prediction Server. Nucleic Acids Research, v.32: W130-W134.*
Pontius, et al. (2003) The NCBI Handbook. [on-line], Internet <URL: http://www.ncbi.nlm.nih.gov/books/bv.fcgi?>.rid=handbook.*
Whitehead Institute siRNA Selection Tool [online], Internet <URL: http://jura.wi.mit.edu/bioc/siRNAext/home.php>.*
Bird et al., "Single-Chain Antigen-Binding Proteins", *Science*, 242: 423-426, (1988).
Chaloin et al., "Design of Carrier Peptide-Oligonucleotide Conjugates with Rapid Membrane Translocation and Nuclear Localization Properties", *Biochemical and Biophysical Research Communications*, 243: 601-608 (1998).
Chen et al., "Gene Therapy for Brain Tumors: Regression of Experimental Gliomas by Adenovirus—Mediated Gene Transfer in vivo", *Proc. Natl. Acad. Sci. USA*, 91: 3054-3057 (1994).
Chiba-Falek et al., "Effect of Allelic Variation at the NACP-Rep1 Repeat Upstream of the α-synuclein gene (SNCA) on Transcription in a Cell Culture Luciferase Reporter System", *Human Molecular Genetics*, 10(26): 3101-3109(2001).
Chiba-Falek et al., "Functional Analysis of Intra-Allelic Variation at NACP-Rep1 in the α-synuclein Gene", *Hum. Genet.*, 113: 426-431 (2003).
Derossi et al., "The Third Helix of Antennapedia Homeodomain Translocates through Biological Membranes", *The Journal of Biological Chemistry*, 269(14); 10444-10450 (1994).
Elbashir etal., "RNA Interference is Mediated bu 21- and 22-Nucleotide RNAs", *Genes & Development*, 15: 188-200 (2001).
Elmquist et al., "VE-Cadherin-Derived Cell-Penetrating Peptide, pVEC, with Carrier Functions", *Experimental Cell Research*, 269: 237-244 (2001).
Fire et al., "Potent and Specific Genetic Interference by Double-Stranded RNA in *Caenorhabditis elegans*", *Nature*, 391: 806-811 (1998).

(Continued)

*Primary Examiner*—Amy Bowman

(57) ABSTRACT

Aspects featured in the invention relate to compositions and methods for inhibiting alpha-synuclein (SNCA) gene expression, such as for the treatment of neurodegenerative disorders. An anti-SNCA agent featured herein that targets the SNCA gene can have been modified to alter distribution in favor of neural cells.

11 Claims, 15 Drawing Sheets

OTHER PUBLICATIONS

Giasson et al., "Neuronal α-Synucleinopathy with Severe Movement Disorder in Mice Expressing A53T Human α-synuclein", *Neuron*, 34: 521-533, (2002).

Hammond et al., "Argonaute2, A Link Between Genetic and Biochemical Analyses of RNAi", *Science*, 293: 1146-1150 (2001).

Heid et al., "Real Time Quantitative PCR", *Genome Research*, 6: 986-994 (1996).

Huston et al., "Protein Engineering of Antibody Binding Sites: Recovery of Specific Activity in an Anti-Digoxin Single-Chain Fv Analogue Produced in *Escherichia coli*", *Proc. Natl. Acad. Sci. USA*, 85: 5879-5883 (1988).

Ketting et al., "Dicer Functions in RNA Interference and in Synthesis of Small RNA involved in Developmental Timing in *C. elegans*", *Genes & Development*, 15: 2654-2659 (2001).

Kruger et al., "Increased Susceptibility to Sporadic Parkinson's Disease by a Certain Combined α-Synuclein/Apolipoprotein E Genotype", *Annals of Neurology*, 45(5): 611-617, (1999).

Lam et al., "A New Type of Synthetic Peptide Library for Identifying Ligand-Binding Activity", *Nature*, 354: 82-84 (1991).

Lee et al., "Human α-synuclein-harboring familial Parkinson's disease-linked Ala-53 -> Thr mutation casues neurodegenerative disease with α-synuclein aggregation in transgenic mice", *Proc. Natl. Acad. Sci. USA*, 99 (13): 8968-8973 (2002).

Limbach et al., "Summary: The Modified Nucleosides of RNA", *Nucleic Acids Research*, 22(12): 2183-2196 (1994).

Masliah et al., "Dopaminergic Loss and Inclusion Body Formation in α-Synuclein Mice: Implications for Neurodegenerative Disorders", *Science*, 287 (5456): 1265-1269 (2000).

Mi et al., "Characterization of a Class of Cationic Peptides Able to Facilitate Efficient Protein Transduction in Vitro and in Vivo" *Molecular Therapy*, 2(4): 339-347 (2000).

Mitchell et al., "Polyarginine Enters Cells More Efficiently than Other Polycationic Homopolymers", *J. Peptide Res.*, 56: 318-325 (2000).

Nykanen et al., "ATP Requirements and Small Interfering RNA Structure in the RNA Interference Pathway", *Cell*, 107: 309-321, (2001).

Pooga et al., "Cell Penetration by Transportation", *The FASEB Journal*, 12: 67-77(1998).

Richfield et al., "Behavioral and Neurochemical Effects of Wild-Type and Mutated Human α-Synuclein in Transgenic Mice", *Experimental Neurology*, 175: 35-48 (2002).

Simeoni et al., "Insight into the Mechanism of the Peptide-Based Gene Delivery System MPG: Implications for Delivery of siRNA into Mammalian Cells", *Nucleic Acids Research*, 31(11): 2717-2724, (2003).

Singleton et al., "α-Synuclein Locus Triplication Causes Parkinson's Disease", *Science*, 302: 841 (2003).

Touchman et al., "Human and Mouse α-synuclein Genes: Comparative Genomic Sequence Analysis and Identification of a Novel Gene Regulatory Element", *Genome Research*, 11: 78-86, (2001).

Vives et al., "A Truncated HIV-1 Tat Protein Basic Domain Rapidly Translocates through the Plasma Membrane and Accumulates in the Cell Nucleus", *The Journal of Biological Chemistry*, 272(25): 16010-16017 (1997).

Ward et al., "Binding Activities of a Repertoire of Single Immunoglobulin Variable Domains Secreted from *Escherichia coil*" *Nature*, 341: 544-546 (1989).

GenBank Access. No. NM_000345; 42 pages (priority: Oct. 1, 2006).

Boese et al., "Mechanical Insights Aid Computational Short Interfering RNA Design," Methods in Enzymology 392:73-96 (2005).

Reynolds et al., "Rational siRNA design for RNA interference," Nature Biotechnology 22:326-330 (2004).

Amosova et al., "Effect of the 1-(2'-deoxy-beta-D-ribofuranosyl)-3-nitropyrrole residue on the stability of DNA duplexes and triplexes" *Nucleic Acids Res*. 25:1930-1934 (1997).

Ausin et al., "Synthesis of Amino- and Guanidino-G-Clamp PNA Monomers" *Organic Letters* 4:4073-4075 (2002).

Berger et al., "Universal bases for hybridization, replication and chain termination" *Nucleic Acids Res*. 28:2911-2914 (2000).

Bergstrom et al., "Synthesis, Structure, and Deoxyribonucleic Acid Sequencing with a Universal Nucleoside: 1-(2'-Deoxy-J-D-ribofuranosyl)-3-nitropyrrole" *Am. Chem. Soc.* 117:1201-1209 (1995).

Brotschi et al., "A Stable DNA Duplex Containing a Non-Hydrogen-Bonding and Non-Shape-Complementary Base Couple: Interstrand Stacking as the Stability Determining Factor" *Agnew Chem. Int. Ed.* 40:3012-3014 (2001).

Flanagan et al., "A cytosine analog that confers enhanced potency to antisense olignucleotides," *Proceedings Of The National Academy Of Sciences Of The United States Of America* 96:3513-3518 (1999).

Guckian et al., "Structure and Base Pairing Properties of a Replicable Nonpolar Isostere for Deoxyadenosine" *J. Org. Chem*. 63:9652-9656 (1998).

Holmes et al., "Steric inhibition of human immunodeficiency virus type-1 Tat-dependent trans-activation in vitro and in cells by oligonucleotides containing 2'-O-methyl G-clamp ribonucleoside analogues," *Nucleic Acids Res*. 31:2759-2768 (2003).

Holmes et al., "The Synthesis of 2'-O-Methyl G-Clamp Containing Oligonucleotides and Their Inhibition of the HIV-1 Tat-TAR Interaction" *Nucleotides & Nucleic Acids* 22:1259-1262 (2003).

Lan et al., "Minor Groove Hydration is Critical to the Stability of DNA Duplexes" *J. Am. Chem. Soc.* 122:6512-6513 (2000).

Liu et al., "Bi-stranded, multisite replication of a base pair between difluorotoluene and adenine: confirmation by 'inverse' sequencing" *Chem. Biol*. 4:919-926 (1997).

Maier et al., "Nuclease resistance of oligonucleotides containing the tricycle cystosine analogues phenoxazine and 9-(2-aminoethoxy)-phenoxazine ("G-clamp") and origins of their nuclease resistance properties," *Biochemistry* 41:1323-1327 (2002).

Matray et al., "Selective and Stable DNA Base Pairing without Hydrogen Bonds" *J. Am. Chem. Soc.* 120:6191-6192 (1998).

McMinn et al., "Efforts toward Expansion of the Genetic Alphabet; DNA Polymerase Recognition of a Highly Stable, Self-Pairing Hydrophobic Base" *J. Am. Chem. Soc.* 121:11585-11586 (1999).

Morales et al., "Importance of Terminal Base Pair Hydrogen-Bonding in 3'-End Proofreading by the Klenow Fragment of DNA Polyerase1" *Biochem*. 39:2626-2632 (2000).

Moran et al., "Difluorotoluene, a Nonpolar Isotere for Thymine, Codes Specifically and Efficiently for Adenine in DNA Replication" *J. Am. Chem. Soc.* 119:2056-2057 (1997).

Nakatani et al., "Specific binding of 2-amino-1,8-naphthyridine into a single guanine bulge as evidenced by photooxidation of GG doublet" *Bioorg. Med. Chem. Lett.* 11:335-337 (2001).

Nakatani et al., "Recognition of a Single Guanine Bulge by 2-Acylamino-1, 8-naphthyridine" *J. Am. Chem. Soc.* 122:2172-2177 (2000).

Ogawa et al., "Efforts toward the Expansion of the Genetic Alphabet: Information Storage and Replication with Unnatural Hydrophobic Base Pairs" *J. Am. Chem. Soc.* 122:3274-3287 (2000).

Ogawa et al., "Rational Design of an Unnatural Base Pair with Increased Kinetic Selectivity" *J. Am. Chem. Soc.* 122:8803-8804 (2000).

Oliver et al., "Effect of the universal base 3-nitropyrrole on the selectivity of neighboring natural bases" *Organic Lett*. 3:1977-1980 (2001).

Pirrung et al., "A universal, photocleavable DNA base: nitropiperonyl 2'-deoxyriboside" *J. Org. Chem.* 66:2067-2071 (2001).

Rajeev et al., "High Affinity Peptide Nucleic Acid Oligomers Containing Tricyclic Cystosine Analogues" *Organic Letters* 4:4395-4398 (2002).

Tae et al., "Efforts toward expansion of the genetic alphabet: replication of DNA with three base pairs" *J. Am. Chem. Soc.* 123:7439-7440 (2001).

Weizman et al., "2,2'-Bipyridine ligandoside: a novel building block for modifying DNA with intra-duplex metal complexes" *J. Am. Chem. Soc.* 123:3375-3376 (2001).

Wilds et al., "Structural basis for recognition of guanosine by a synthetic tricyclic cytosine analogue: Guanidinium G-clamp" *Helvetica Chimica Acta* 86:966-978 (2003).

Wu et al., "Efforts toward Expansion of the Genetic Alphabet: Optimization of Interbase Hydrophobic Interactions" *J. Am. Chem. Soc.* 122(32):7621-7632 (2000).

Zimmerman et al., "Model Studies Directed toward a General Triplex DNA Recognition Scheme: A Novel DNA Base That Binds a CG Base-Pair in an Organic Solvent" *J. Am. Chem. Soc.* 117:10769-10770 (1995).

International Search Report and Written Opinion, PCT/US2004/018271, Feb. 13, 2008.

Examiner's First Report on Patentability, Australian Patent Application No. AU 2004255557, Nov. 6, 2008.

Appeal Brief filed with the United States Patent and Trademark Office on Jun. 16, 2008, U.S. Appl. No. 10/991,286, filed Nov. 17, 2004.

Examiner's Answer to Appeal Brief, Notification from United States Patent and Trademark office on Sep. 5, 2008, U.S. Appl. No. 10/991,286, filed Nov. 17, 2004.

Reply Brief filed with the United States Patent and Trademark Office on Oct. 24, 2008, U.S. Appl. No. 10/991,286, filed Nov. 17, 2004.

\* cited by examiner

```
  1 ggagtggcca ttcgacgaca gtgtggtgta aaggaattca ttagccatgg atgtattcat
 61 gaaaggactt tcaaaggcca aggagggagt tgtggctgct gctgagaaaa ccaaacaggg
121 tgtggcagaa gcagcaggaa agacaaaaga gggtgttctc tatgtag[gct ccaaaaccaa
181 ggagggagtg gtgcatggtg tggc                              agagc aagtgacaaa
241 tgttggagga gcagtggtga cgggtgtgac agcagtagcc cagaagacag tggagggagc
301 agggagcatt gcagcagcca ctggctttgt caaaaaggac cagttgggca ag[aatgaaga
361 aggagcccca caggaaggaa ttctggaaga tatgcctgtg ga
421 ]gaaatgcct tctgag]gaag ggtatcaaga                              g aaatatcttt
481 gctcccagtt tcttgagatc tgctgacaga tgttccatcc tgtacaagtg ctcagttcca
541 atgtgcccag tcatgacatt tctcaaagtt tttacagtgt atctcgaagt cttccatcag
601 cagtgattga agtatctgta cctgccccca ctcagcattt cggtgcttcc ctttcactga
661 agtgaataca tggtagcagg gtctttgtgt gctgtggatt ttgtggcttc aatctacgat
721 gttaaaacaa attaaaaaca cctaagtgac taccacttat ttctaaatcc tcactatttt
781 tttgttgctg ttgttcagaa gttgttagtg atttgctatc atatattata agattttttag
841 gtgtcttta atgatactgt ctaagaataa tgacgtattg tgaaatttgt taatatatat
901 aatacttaaa aatatgtgag catgaaacta tgcacctata aatactaaat atgaaatttt
961 accattttgc gatgtgtttt attcacttgt gtttgtatat aaatggtgag aattaaaata
1021 aaacgttatc tcattgcaaa atatttttat ttttatccca tctcacttta ataataaaaa
1081 tcatgcttat aagcaacatg aattaagaac tgacacaaag gacaaaaata taaagttatt
1141 aatagccatt tgaagaagga ggaatttag aagaggtaga gaaatggaa cattaaccct
1201 acactcggaa ttccctgaag caacactgcc agaagtgtgt tttggtatgc actggttcct
1261 taagtggctg tgattaatta ttgaaagtgg ggtgttgaag accccaacta ctattgtaga
1321 gtggtctatt tctcccttca atcctgtcaa tgtttgcttt atgtattttg gggaactgtt
1381 gtttgatgtg tatgtgttta taattgttat acatttttaa ttgagccttt tattaacata
1441 tattgttatt tttgtctcga aataattttt tagttaaaat ctattttgtc tgatattggt
1501 gtgaatgctg tacctttctg acaataaata atattcgacc atg
```

SEQ ID NO:1

FIG. 1A

```
1    MDVFMKGLSK AKEGVVAAAE KTKQGVAEAA GKTKEGVLYV GSKTKEGVVH
51   GVATVAEKTK EQVTNVGGAV VTGVTAVAQK TVEGAGSIAA ATGFVKKDQL
101  GKNEEGAPQE GILEDMPVDP DNEAYEMPSE EGYQDYEPEA
```

SEQ ID NO:2

FIG. 1B

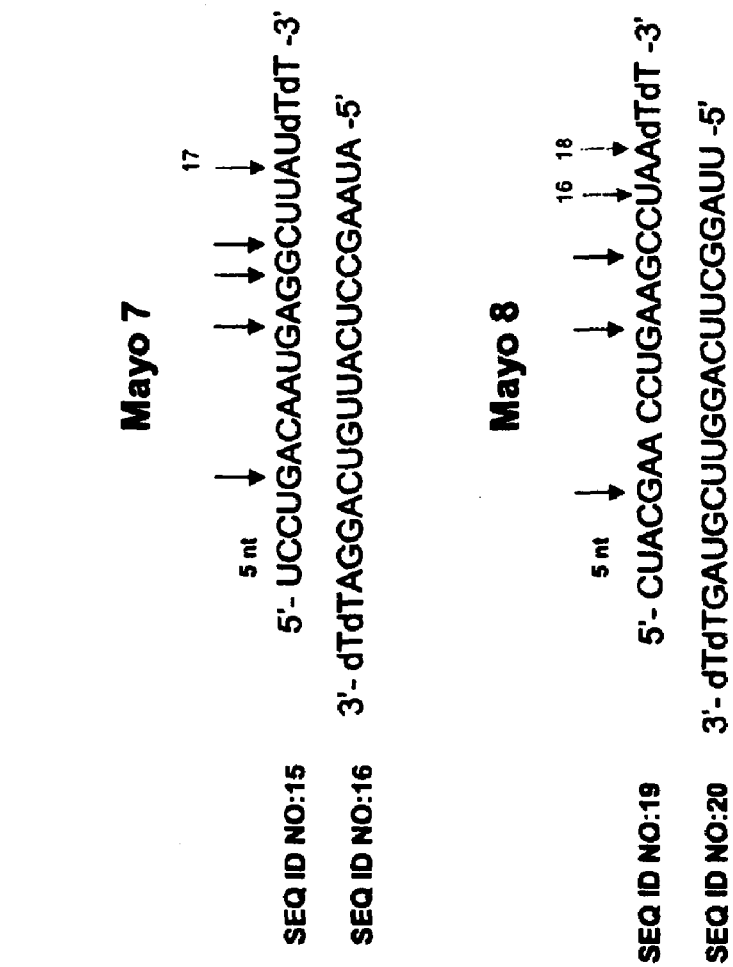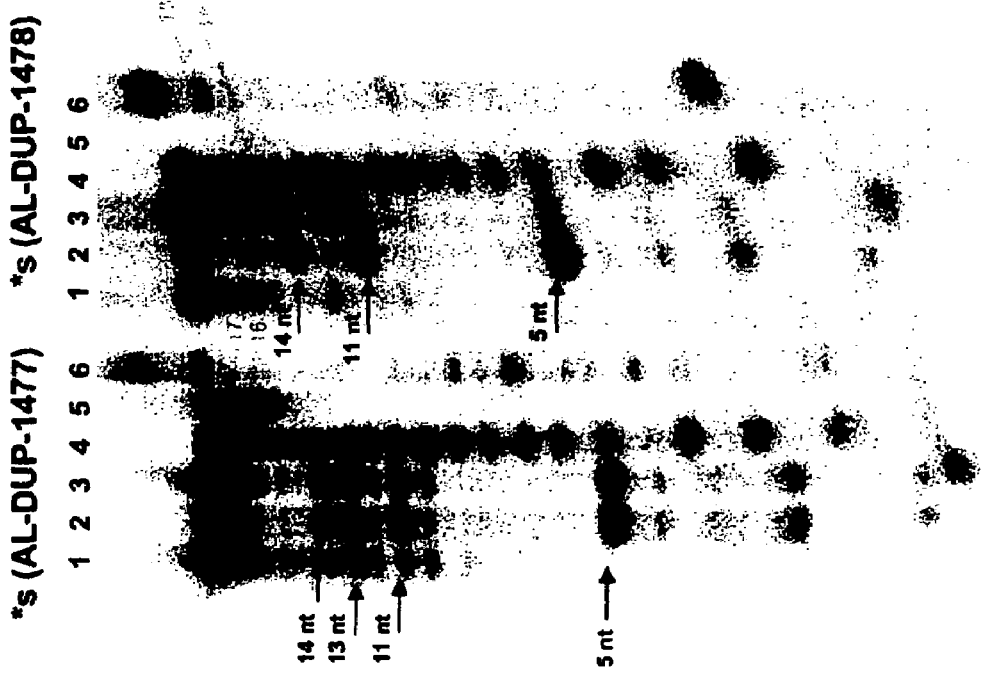
FIG. 8A
FIG. 8B

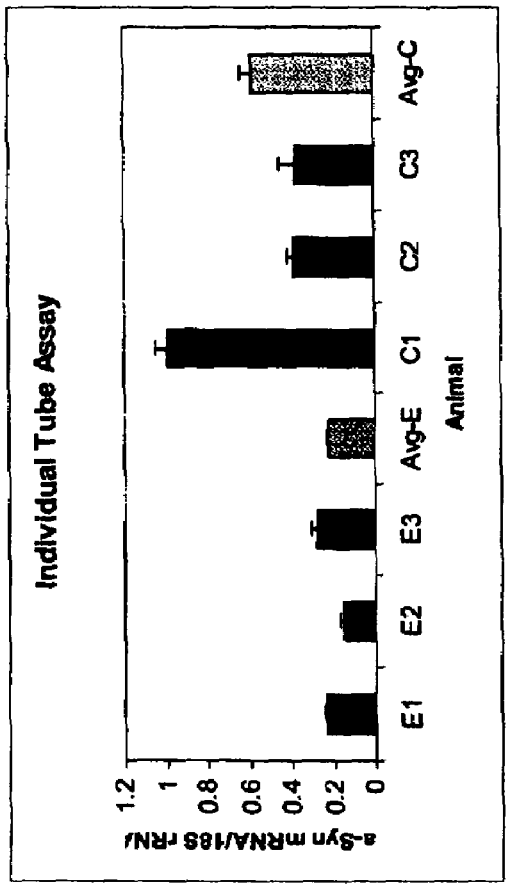
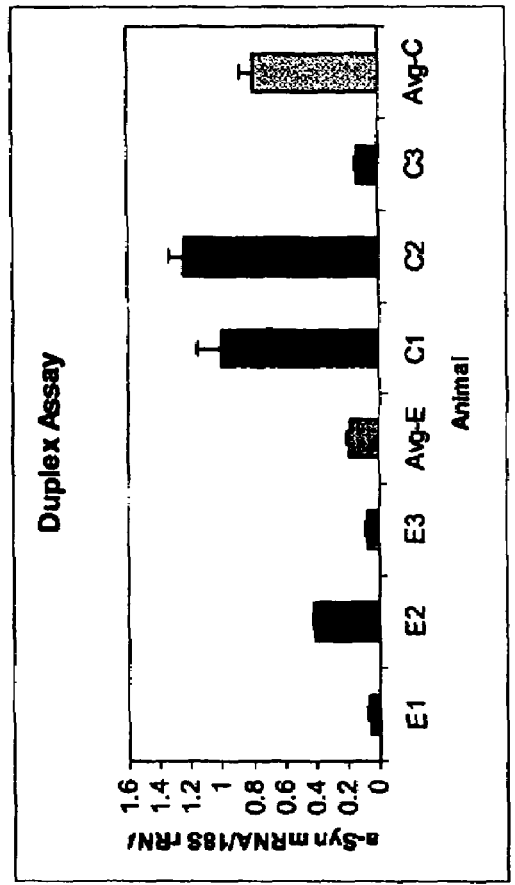
FIG. 12A
FIG. 12B

METHOD OF TREATING NEURODEGENERATIVE DISEASE

RELATED APPLICATIONS

This application is a continuation-in-part of U.S. application Ser. No. 10/991,286, filed Nov. 17, 2004, which is a continuation-in-part of International Application No. PCT/US2004/018271, filed Jun. 9, 2004, which claims the benefit of U.S. Provisional Application No. 60/476,947, filed Jun. 9, 2003. The contents of these applications are incorporated herein by reference in their entirety.

GOVERNMENT SUPPORT

The work described herein was carried out, at least in part, using funds from the U.S. government under grant number ES10751 awarded by National Institute of Environmental Health Sciences, and grant numbers NS33978 and NS40256 awarded by the National Institute of Neurological Disorders and Stroke. The government may therefore have certain rights in the invention.

TECHNICAL FIELD

This invention relates to methods and compositions for treating neurodegenerative disease, and more particularly to the downregulation of the alpha-synuclein gene for the treatment of synucleinopathies.

BACKGROUND

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function.

Expression of the SNCA gene produces the protein alpha-synuclein. Mutations in the SNCA gene and SNCA gene multiplications have been linked to familial Parkinson's disease (PD). PD patients demonstrate alpha-synuclein protein aggregates in the brain. Similar aggregates are observed in patients diagnosed with sporadic PD, Alzheimer's Disease, multiple system atrophy, and Lewy body dementia.

SUMMARY

Aspects of the invention relate to compositions for inhibiting alpha-synuclein (SNCA) expression, and methods of using those compositions. In one aspect, the invention features a method of treating a subject by administering an agent which inhibits expression of SNCA. In a preferred embodiment, the subject is a mammal, such as a human, e.g., a subject diagnosed as having, or at risk for developing, a neurodegenerative disorder. The inhibition can be effected at any level, e.g., at the level of transcription, the level of translation, or post-transitionally. Agents that inhibit SNCA expression include iRNA agents, ribozymes, and antisense molecules that target SNCA RNA, zinc finger proteins, as well as antibodies or naturally occurring or synthetic polypeptides, or small molecules, which, in preferred embodiments, bind to and inhibit the SNCA protein.

In a particularly preferred embodiment the inhibitory agent is an iRNA agent that targets an SNCA nucleic acid, e.g., an SNCA RNA. The iRNA agent has an antisense strand complementary to a nucleotide sequence of an SNCA RNA, and a sense strand sufficiently complementary to hybridize to the antisense strand. In one embodiment, the iRNA agent includes a modification that stabilizes the iRNA agent in a biological sample. For example, the modified iRNA agent is less susceptible to degradation, e.g., less susceptible to cleavage by an exo- or endonuclease. The iRNA agent can include, for example, at least one 5'-uridine-adenine-3' (5'-UA-3') dinucleotide wherein the uridine is a 2'-modified nucleotide, or at least one 5'-uridine-guanine-3' (5'-UG-3') dinucleotide, wherein the 5'-uridine is a 2'-modified nucleotide, or at least one 5'-cytidine-adenine-3' (5'-CA-3') dinucleotide, wherein the 5'-cytidine is a 2'-modified nucleotide, or at least one 5'-uridine-uridine-3' (5'-UU-3') dinucleotide, wherein the 5'-uridine is a 2'-modified nucleotide, or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of the dinucleotides. In one embodiment, the 2'-modified nucleotide is a 2'-O-methylated nucleotide. In another embodiment the iRNA agent includes a phosphorothioate.

In another embodiment, the antisense strand of the iRNA agent includes the nucleotide sequence of SEQ ID NOs:6, 16, 18, 20, 22, or 24. In another embodiment, the sense strand of the iRNA agent includes the nucleotide sequence of SEQ ID NOs:5, 15, 17, 19, 21, or 23. In yet another embodiment, the antisense strand of the iRNA agent overlaps the nucleotide sequence of SEQ ID NOs:6, 16, 18, 20, 22, or 24, e.g., by at least 1, 5, 10, 11, 12, 13, 14, 15, 16, 17, 18, 19, 20, 21, 22, 23, or 24 nucleotides. Likewise, the sense strand of the iRNA agent can overlap the nucleotide sequence of SEQ ID NOs:5, 15, 17, 19, 21, or 23, e.g., by at least 1, 5, 10, 11, 12, 13, 14, 15, 16, 17, 18, 19, 20, 21, 22, 23, or 24 nucleotides.

In another embodiment, the iRNA agent targets a wildtype SNCA nucleic acid, and in yet another embodiment, the iRNA agent targets a polymorphism or mutation of SNCA. For example, the iRNA agent can target a mutation in a codon of the SNCA open reading frame that corresponds to an A53T, A30P, or E46K mutation. In some embodiments, the iRNA agent targets the 3'UTR or the 5'UTR of SNCA. In some embodiment, the iRNA agent targets a spliced isoform of SNCA. For example, the iRNA agent can target the splice junction between exons 2 and 4 to downregulate expression of the 128 amino acid isoform, or the iRNA agent can target the splice junction between exons 4 and 6 to target the 112 amino acid isoform.

In some embodiments, the subject (e.g., the human) carries a multiplication (e.g., a duplication or triplication) of the SNCA gene, or a genetic variation in the Parkin or ubiquitin carboxy-terminal hydrolase L1 (UCHL1) gene. In another embodiment, the subject is diagnosed with a synucleinopathy. The synucleinopathy is characterized by the aggregation of alpha-synuclein monomers. An iRNA agent can be administered to a human diagnosed as having, e.g., Parkinson's disease (PD), Alzheimer's disease, multiple system atrophy, Lewy body dementia, or a retinal disorder, e.g., a retinopathy.

In another embodiment, the iRNA agent is at least 21 nucleotides long and includes a sense RNA strand and an antisense RNA strand, wherein the antisense RNA strand is 25 or fewer nucleotides in length, and the duplex region of the iRNA agent is 18-25 nucleotides in length. The iRNA agent may further include a nucleotide overhang having 1 to 4 unpaired nucleotides, and the unpaired nucleotides may have at least one phosphorothioate dinucleotide linkage. The nucleotide overhang can be, e.g., at the 3' end of the antisense strand of the iRNA agent.

In another aspect, the invention features an iRNA agent that targets an SNCA nucleic acid, e.g., an SNCA RNA. The iRNA agent has an antisense strand complementary to a nucleotide sequence of an SNCA RNA, and a sense strand sufficiently complementary to hybridize to the antisense strand. In one embodiment, the iRNA agent includes a modification that stabilizes the iRNA agent in a biological sample. For example, the modified iRNA agent is less susceptible to degradation, e.g., less susceptible to cleavage by an exo- or endonuclease. In another embodiment, the iRNA agent comprises a phosphorothioate or 2'-O-methylated (2'-O-Me) nucleotide. The iRNA agent can include, for example, at least one 5'-uridine-adenine-3' (5'-UA-3') dinucleotide wherein the uridine is a 2'-modified nucleotide, or at least one 5'-uridine-guanine-3' (5'-UG-3') dinucleotide, wherein the 5'-uridine is a 2'-modified nucleotide, or at least one 5'-cytidine-adenine-3' (5'-CA-3') dinucleotide, wherein the 5'-cytidine is a 2'-modified nucleotide, or at least one 5'-uridine-uridine-3' (5'-UU-3') dinucleotide, wherein the 5'-uridine is a 2'-modified nucleotide, or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of the dinucleotides. In one embodiment, the 2'-modified nucleotide is a 2'-O-methylated nucleotide.

In another embodiment, the iRNA agent is at least 21 nucleotides long and includes a sense RNA strand and an antisense RNA strand, wherein the antisense RNA strand is 25 or fewer nucleotides in length, and the duplex region of the iRNA agent is 18-25 nucleotides in length. The iRNA agent may further include a nucleotide overhang having 1 to 4 unpaired nucleotides, and the unpaired nucleotides may have at least one phosphorothioate dinucleotide linkage. The nucleotide overhang can be, e.g., at the 3' end of the antisense strand of the iRNA agent.

In another embodiment, the antisense strand of the iRNA agent includes the nucleotide sequence of SEQ ID NOs:6, 16, 18, 20, 22, or 24 (see Table 1). In another embodiment, the sense strand of the iRNA agent includes the nucleotide sequence of SEQ ID NOs:5, 15, 17, 19, 21, or 23 (see Table 1). In yet another embodiment, the antisense strand of the iRNA agent overlaps the nucleotide sequence of SEQ ID NOs:6, 16, 18, 20, 22, or 24, e.g., by at least 1, 5, 10, 11, 12, 13, 14, 15, 16, 17, 18, 19, 20, 21, 22, 23, or 24 nucleotides. Likewise, the sense strand of the iRNA agent can overlap the nucleotide sequence of SEQ ID NOs:5, 15, 17, 19, 21, or 23, e.g., by at least 1, 5, 10, 11, 12, 13, 14, 15, 16, 17, 18, 19, 20, 21, 22, 23, or 24 nucleotides.

In another embodiment, the iRNA agent targets a wildtype SNCA nucleic acid, and in yet another embodiment, the iRNA agent targets a polymorphism or mutation of SNCA. For example, the iRNA agent can target a mutation in a codon of the SNCA open reading frame that corresponds to an A53T, A30P, or E46K mutation (see FIG. 1B). In some embodiments, the iRNA agent targets the 5'UTR or the 3'UTR of SNCA. In some embodiment, the iRNA agent targets a spliced isoform of SNCA. For example, the iRNA agent can target the splice junction between exons 2 and 4 to downregulate expression of the 128 amino acid isoform, or the iRNA agent can target the splice junction between exons 4 and 6 to target the 112 amino acid isoform.

The SNCA gene can be a target for treatment methods of neurodegenerative disease. In one embodiment, an antisense oligonucleotide, ribozyme, or zinc finger protein can be used to inhibit gene expression, or an antibody or small molecule can be used to target an SNCA polypeptide. A combination of therapies to downregulate SNCA expression and activity can also be used.

In another aspect, the invention features a pharmaceutical composition of an inhibitory agent described herein, e.g., an iRNA agent, ribozyme, or antisense molecule which targets SNCA RNA, an antibody or naturally occurring or synthetic polypeptide, or small molecule, which preferably binds to and inhibits the SNCA protein, and a pharmaceutically acceptable carrier.

In a particularly preferred embodiment, the pharmaceutical composition includes an iRNA agent targeting the SNCA gene and a pharmaceutically acceptable carrier. The iRNA agent has an antisense strand complementary to a nucleotide sequence of an SNCA RNA, and a sense strand sufficiently complementary to hybridize to the antisense strand. In one embodiment, the iRNA agent of the pharmaceutical composition includes a modification that stabilizes the iRNA agent in a biological sample. For example, the modified iRNA agent is less susceptible to degradation, e.g., less susceptible to cleavage by an exo- or endonuclease. The iRNA agent can include, for example, at least one 5'-uridine-adenine-3' (5'-UA-3') dinucleotide wherein the uridine is a 2'-modified nucleotide, or at least one 5'-uridine-guanine-3' (5'-UG-3') dinucleotide, wherein the 5'-uridine is a 2'-modified nucleotide, or at least one 5'-cytidine-adenine-3' (5'-CA-3') dinucleotide, wherein the 5'-cytidine is a 2'-modified nucleotide, or at least one 5'-uridine-uridine-3' (5'-UU-3') dinucleotide, wherein the 5'-uridine is a 2'-modified nucleotide, or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of the dinucleotides. In one embodiment, the 2'-modified nucleotide is a 2'-O-methylated nucleotide. In another embodiment the iRNA agent includes a phosphorothioate.

In another embodiment, the iRNA agent of the pharmaceutical composition is at least 21 nucleotides long and includes a sense RNA strand and an antisense RNA strand, wherein the antisense RNA strand is 25 or fewer nucleotides in length, and the duplex region of the iRNA agent is 18-25 nucleotides in length. The iRNA agent of the composition may further include a nucleotide overhang having 1 to 4 unpaired nucleotides, and the unpaired nucleotides may have at least one phosphorothioate dinucleotide linkage. The nucleotide overhang can be, e.g., at the 3' end of the antisense strand of the iRNA agent.

In another embodiment, the antisense strand of the iRNA agent of the pharmaceutical composition includes the nucleotide sequence of SEQ ID NOs:6, 16, 18, 20, 22, or 24. In another embodiment, the sense strand of the iRNA agent of the pharmaceutical composition includes the nucleotide sequence of SEQ ID NOs:5, 15, 17, 19, 21, or 23. In yet another embodiment, the antisense strand of the iRNA agent overlaps the nucleotide sequence of SEQ ID NOs:6, 16, 18, 20, 22, or 24, e.g., by at least 1, 5, 10, 11, 12, 13, 14, 15, 16, 17, 18, 19, 20, 21, 22, 23, or 24 nucleotides. Likewise, the sense strand of the iRNA agent can overlap the nucleotide sequence of SEQ ID NOs:5, 15, 17, 19, 21, or 23, e.g., by at least 1, 5, 10, 11, 12, 13, 14, 15, 16, 17, 18, 19, 20, 21, 22, 23, or 24 nucleotides.

In another embodiment, the iRNA agent targets a wildtype SNCA nucleic acid, and in another embodiment, the iRNA agent targets a polymorphism or mutation of SNCA. For example, the iRNA agent can target a mutation in a codon of the SNCA open reading frame that corresponds to an A53T, A30P, or E46K mutation. In some embodiments, the iRNA agent targets the 3'UTR or the 5'UTR of SNCA. In some embodiments, the iRNA agent targets a spliced isoform of SNCA. For example, the iRNA agent can target the splice junction between exons 2 and 4 to downregulate expression of the 128 amino acid isoform, or the iRNA agent can target the splice junction between exons 4 and 6 to target the 112 amino acid isoform. In another aspect, the invention features a method of reducing the amount of SNCA or SNCA RNA in a cell of a subject (e.g., a mammalian subject, such as a human). The method includes contacting cell with an agent which inhibits the expression of SNCA. The inhibition can be effected at any level, e.g., at the level of transcription, the level of translation, or post-translationally. Agents which inhibit SNCA expression include iRNA agents and antisense molecules which target SNCA RNA, as well as antibodies or naturally occurring or synthetic polypeptides, or small molecules, which, in preferred embodiments, bind to and inhibit the SNCA protein.

In a particularly preferred embodiment SNCA RNA is reduced by contacting a cell of the subject with an iRNA agent. In one embodiment, the iRNA agent includes a modification that stabilizes the iRNA agent in a biological sample. For example, the modified iRNA agent is less susceptible to degradation, e.g., less susceptible to cleavage by an exo- or endonuclease. The iRNA agent can include, for example, at least one 5'-uridine-adenine-3' (5'-UA-3') dinucleotide wherein the uridine is a 2'-modified nucleotide, or at least one 5'-uridine-guanine-3' (5'-UG-3') dinucleotide, wherein the 5'-uridine is a 2'-modified nucleotide, or at least one 5'-cytidine-adenine-3' (5'-CA-3') dinucleotide, wherein the 5'-cytidine is a 2'-modified nucleotide, or at least one 5'-uridine-uridine-3' (5'-UU-3') dinucleotide, wherein the 5'-uridine is a 2'-modified nucleotide, or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of the dinucleotides. In one embodiment, the 2'-modified nucleotide is a 2'-O-methylated nucleotide. In another embodiment the iRNA agent includes a phosphorothioate.

In another embodiment, the antisense strand of the iRNA agent of the pharmaceutical composition includes the nucleotide sequence of SEQ ID NOs:6, 16, 18, 20, 22, or 24. In another embodiment, the sense strand of the iRNA agent of the pharmaceutical composition includes the nucleotide sequence of SEQ ID NOs:5, 15, 17, 19, 21, or 23. In yet another embodiment, the antisense strand of the iRNA agent overlaps the nucleotide sequence of SEQ ID NOs:6, 16, 18, 20, 22, or 24, e.g., by at least 1, 5, 10, 11, 12, 13, 14, 15, 16, 17, 18, 19, 20, 21, 22, 23, or 24 nucleotides. Likewise, the sense strand of the iRNA agent can overlap the nucleotide sequence of SEQ ID NOs:5, 15, 17, 19, 21, or 23, e.g., by at least 1, 5, 10, 11, 12, 13, 14, 15, 16, 17, 18, 19, 20, 21, 22, 23, or 24 nucleotides.

In another embodiment, the iRNA agent targets a wildtype SNCA nucleic acid, and in another embodiment, the iRNA agent targets a polymorphism or mutation of SNCA. For example, the iRNA agent can target a mutation in a codon of the SNCA open reading frame that corresponds to an A53T, A30P, or E46K mutation. In some embodiments, the iRNA agent targets the 3'UTR or the 5'UTR of SNCA. In some embodiments, the iRNA agent targets a spliced isoform of SNCA. For example, the iRNA agent can target the splice junction between exons 2 and 4 to downregulate expression of the 128 amino acid isoform, or the iRNA agent can target the splice junction between exons 4 and 6 to target the 112 amino acid isoform.

In another embodiment, the iRNA agent is at least 21 nucleotides long and includes a sense RNA strand and an antisense RNA strand, wherein the antisense RNA strand is 25 or fewer nucleotides in length, and the duplex region of the iRNA agent is 18-25 nucleotides in length. The iRNA agent may further include a nucleotide overhang having 1 to 4 unpaired nucleotides, and the unpaired nucleotides may have at least one phosphorothioate dinucleotide linkage. The nucleotide overhang can be, e.g., at the 3' end of the antisense strand of the iRNA agent.

In another aspect, the invention features a method of making an iRNA agent. The method includes selecting a nucleotide sequence of between 18 and 25 nucleotides long from the nucleotide sequence of an SNCA mRNA, and synthesizing the iRNA agent. The sense strand of the iRNA agent includes the nucleotide sequence selected from SNCA RNA, and the antisense strand is sufficiently complementary to hybridize to the sense strand. In one embodiment, the method further includes administering the iRNA agent to a subject (e.g., a mammalian subject, such as a human subject) as described herein.

In another aspect, the invention features a method of evaluating an agent, e.g., an agent of a type described herein, such as a small molecule (a small molecule has a molecular weight of preferably less than 3,000 Daltons, more preferably less than 2,000 Daltons and yet more preferably of less than 1000 Daltons), antisense, ribozyme, iRNA agent, or protein, polypeptide, or peptide, e.g., a zinc finger protein, for the ability to inhibit SNCA expression, e.g., an agent that targets an SNCA or SNCA nucleic acid. The method includes: providing a candidate agent and determining, e.g., by the use of one or more of the test systems described herein, if said candidate agent modulates, e.g., inhibits, SNCA expression.

In a preferred embodiment the method includes evaluating the agent in a first test system; and, if a predetermined level of modulation is seen, evaluating the candidate in a second, preferably different, test system. In a particularly preferred embodiment the second test system includes administering the candidate agent to an animal and evaluating the effect of the candidate agent on SNCA expression in the animal. In a preferred embodiment two test systems are used and the first is a high-throughput system, e.g., in such embodiments the first or initial test is used to screen at least 100, 1,000, or 10,000 times more compounds than is the second, preferably animal, system.

A test system can include: contacting the candidate agent with a target molecule, e.g., SNCA, an SNCA nucleic acid, e.g., an RNA or DNA, preferably in vitro, and determining if there is an interaction, e.g., binding of the candidate agent to the target, or modifying the target, e.g., by making or breaking a covalent bond in the target. Modification is correlated with the ability to modulate SNCA expression. The test system can include contacting the candidate agent with a cell and evaluating modulation of SNCA expression. E.g., this can include contacting the candidate agent with a cell capable of expressing SNCA or SCNA RNA (from an endogenous gene or from an exogenous construct) and evaluating the level of SNCA or SNCA RNA. In another embodiment the test system can include contacting the candidate agent with a cell which expresses an RNA or protein from an SNCA control region (e.g., an SNCA control region) linked to a heterologous sequence, e.g., a marker protein, e.g., a fluorescent protein such as GFP, which construct can be either chromosomal or episomal, and determining the effect on RNA or protein levels. The test system can also include contacting the candidate agent, in vitro, with a tissue sample, e.g., a brain tissue sample, e.g., a slice or section, an optical tissue sample, or other sample which includes neural tissue, and evaluating the level of SNCA or SNCA RNA. The test system can include administering the candidate agent, in vivo, to an animal, and evaluating the level of SNCA or SNCA RNA. In any of these the effect of the candidate agent on SNCA expression can include comparing SNCA gene expression with a predetermined standard, e.g., with control, e.g., an untreated cell, tissue or animal. SNCA gene expression can be compared, e.g., before and after contacting with the candidate agent. The method allows determining whether the iRNA agent is useful for inhibiting SNCA gene expression.

In one embodiment, SNCA gene expression can be evaluated by a method to examine SNCA RNA levels (e.g., Northern blot analysis, RT-PCR, or RNAse protection assay) or SNCA protein levels (e.g., Western blot).

In one embodiment, e.g., as a second test, the agent is administered to an animal, e.g., a mammal, such as a mouse, rat, rabbit, human, or non-human primate, and the animal is monitored for an effect of the agent. For example, a tissue of the animal, e.g., a brain tissue or ocular tissue, is examined for an effect of the agent on SNCA expression. The tissue can be examined for the presence of SNCA RNA and/or protein, for example. In one embodiment, the animal is observed to monitor an improvement or stabilization of a cognitive symptom. The agent can be administered to the animal by any method, e.g., orally, or by intrathecal or parenchymal injection, such as by stereoscopic injection into the brain.

In a particularly preferred embodiment, the invention features a method of evaluating an iRNA agent, e.g., an iRNA agent described herein, that targets an SNCA nucleic acid. The method includes providing an iRNA agent that targets an SNCA nucleic acid (e.g., an SNCA RNA); contacting the iRNA agent with a cell containing, and capable of expressing, an SNCA gene; and evaluating the effect of the iRNA agent on SNCA expression, e.g., by comparing SNCA gene expression with a control, e.g., in the cell. SNCA gene expression can be compared, e.g., before and after contacting the iRNA agent with the cell. The method allows determining whether the iRNA agent is useful for inhibiting SNCA gene expression. For example, the iRNA agent can be determined to be useful for inhibiting SNCA gene expression if the iRNA agent reduces expression by a predetermined amount, e.g., by 10, 25, 50, 75, or 90%, e.g., as compared with a predetermined reference value, e.g., as compared with the amount of SNCA RNA or protein prior to contacting the iRNA agent with the cell. The SNCA gene can be endogenously or exogenously expressed.

The methods and compositions featured in the invention, e.g., the methods and iRNA compositions to treat the neurodegenerative disorders described herein, can be used with any dosage and/or formulation described herein, as well as with any route of administration described herein.

In addition to their presence in the brain, alpha-synuclein polypeptides have been found in ocular tissues, including the retina and optic nerve. Accordingly, the compositions and methods described herein are suitable for treating synucleinopathies of the eye or ocular tissues, including but not limited to retinopathies.

Thus, in another aspect, the invention features a method of treating a subject by administering an agent which inhibits the expression of SNCA in the eye or in ocular tissue. In a preferred embodiment, the subject is a mammal, such as a human, e.g., a subject diagnosed as having, or at risk for developing a synucleinopathy of the eye, e.g., a retinopathy. The inhibition can be effected at any level, e.g., at the level of transcription, the level of translation, or post-translationally. Agents which inhibit SNCA expression include iRNA agents and antisense molecules which target SNCA RNA, as well as antibodies or naturally occurring or synthetic polypeptides, or small molecules, which, in preferred embodiments, bind to and inhibit the SNCA protein.

In a particularly preferred embodiment the inhibitory agent is an iRNA agent that targets an SNCA nucleic acid, e.g., an SNCA RNA. The iRNA agent has an antisense strand complementary to a nucleotide sequence of an SNCA RNA, and a sense strand sufficiently complementary to hybridize to the antisense strand. In one embodiment, the iRNA agent includes a modification that stabilizes the iRNA agent in a biological sample. For example, the modified iRNA agent is less susceptible to degradation, e.g., less susceptible to cleavage by an exo- or endonuclease. The iRNA agent can include, for example, at least one 5'-uridine-adenine-3' (5'-UA-3') dinucleotide wherein the uridine is a 2'-modified nucleotide, or at least one 5'-uridine-guanine-3' (5'-UG-3') dinucleotide, wherein the 5'-uridine is a 2'-modified nucleotide, or at least one 5'-cytidine-adenine-3' (5'-CA-3') dinucleotide, wherein the 5'-cytidine is a 2'-modified nucleotide, or at least one 5'-uridine-uridine-3' (5'-UU-3') dinucleotide, wherein the 5'-uridine is a 2'-modified nucleotide, or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of the dinucleotides. In one embodiment, the 2'-modified nucleotide is a 2'-O-methylated nucleotide. In another embodiment the iRNA agent includes a phosphorothioate.

In another embodiment, the antisense strand of the iRNA agent includes the nucleotide sequence of SEQ ID NOs:6, 16, 18, 20, 22, or 24. In another embodiment, the sense strand of the iRNA agent includes the nucleotide sequence of SEQ ID NOs:5, 15, 17, 19, 21, or 23. In yet another embodiment, the antisense strand of the iRNA agent overlaps the nucleotide sequence of SEQ ID NOs:6, 16, 18, 20, 22, or 24, e.g., by at least 1, 5, 10, 11, 12, 13, 14, 15, 16, 17, 18, 19, 20, 21, 22, 23, or 24 nucleotides. Likewise, the sense strand of the iRNA agent can overlap the nucleotide sequence of SEQ ID NOs:5, 15, 17, 19, 21, or 23, e.g., by at least 1, 5, 10, 11, 12, 13, 14, 15, 16, 17, 18, 19, 20, 21, 22, 23, or 24 nucleotides.

In another embodiment, the iRNA agent targets a wildtype SNCA nucleic acid, and in yet another embodiment, the iRNA agent targets a polymorphism or mutation of SNCA. For example, the iRNA agent can target a mutation in a codon of the SNCA open reading frame that corresponds to an A53T, A30P, or E46K mutation. In some embodiments, the iRNA agent targets the 3'UTR or the 5'UTR of SNCA. In some embodiment, the iRNA agent targets a spliced isoform of SNCA. For example, the iRNA agent can target the splice junction between exons 2 and 4 to downregulate expression of the 128 amino acid isoform, or the iRNA agent can target the splice junction between exons 4 and 6 to target the 112 amino acid isoform.

In some embodiments, the subject (e.g., the human) carries a multiplication (e.g., a duplication or triplication) of the SNCA gene, or a genetic variation in the Parkin or ubiquitin carboxy-terminal hydrolase L1 (UCHL1) gene. In another embodiment, the subject is diagnosed with a synucleinopathy. The synucleinopathy is characterized by the aggregation of alpha-synuclein monomers. An iRNA agent can be administered to a human diagnosed as having, e.g., Parkinson's disease (PD), Alzheimer's disease, multiple system atrophy, Lewy body dementia, or a retinal disorder, e.g., a retinopathy.

In another embodiment, the iRNA agent is at least 21 nucleotides long and includes a sense RNA strand and an antisense RNA strand, wherein the antisense RNA strand is 25 or fewer nucleotides in length, and the duplex region of the iRNA agent is 18-25 nucleotides in length. The iRNA agent may further include a nucleotide overhang having 1 to 4 unpaired nucleotides, and the unpaired nucleotides may have at least one phosphorothioate dinucleotide linkage. The nucleotide overhang can be, e.g., at the 3' end of the antisense strand of the iRNA agent.

A "substantially identical" sequence includes a region of sufficient homology to the target gene, and is of sufficient length in terms of nucleotides, that the iRNA agent, or a fragment thereof, can mediate down regulation of the target gene. Thus, the iRNA agent is or includes a region which is at least partially, and in some embodiments fully, complementary to a target RNA transcript, e.g, the SNCA transcript. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA. Complementarity, or degree of homology with the target strand, is most critical in the antisense strand. While perfect complementarity, particularly in the antisense strand, is often desired some embodiments can include, particularly in the antisense strand, one or more but preferably 6, 5, 4, 3, 2, or fewer mismatches (with respect to the target RNA). The mismatches, particularly in the antisense strand, are most tolerated in the terminal regions and if present are preferably in a terminal region or regions, e.g., within 6, 5, 4, or 3 nucleotides of the 5' and/or 3' terminus. The sense strand need only be sufficiently complementary with the antisense strand to maintain the overall double strand character of the molecule.

An "RNA agent" as used herein, is an unmodified RNA, modified RNA, or nucleoside surrogates, all of which are described herein or are well known in the RNA synthetic art. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can down-regulate the expression of a target gene, e.g., an SNCA gene. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded (ds) iRNA agent. If the iRNA agent is a single strand it is particularly preferred that it include a 5' modification which includes one or more phosphate groups or one or more analogs of a phosphate group.

An iRNA agent that targets an SNCA nucleic acid can be referred to as an anti-SNCA iRNA agent.

The details of one or more embodiments of the invention are set forth in the accompanying drawings and the description below. Other features, objects, and advantages of the invention will be apparent from this description, and from the claims. This application incorporates all cited references, patents, and patent applications by references in their entirety for all purposes.

BRIEF DESCRIPTION OF DRAWINGS

FIG. 1A is the sequence of the full length mRNA of human SNCA (transcript variant NACP140; GenBank Access. No. NM_000345; SEQ ID NO:1). The start and stop codons of the open reading frame are denoted in bold and italics. Sequences targeted by the siRNAs SNCA1, 3, 4, 5, 6, and 9 are underlined. Sequences of the siRNAs SNCA2, 7 and 8 are shaded in gray. SNCA1 targets nucleotides 197-217; SNCA2 targets nucleotides 205-225; SNCA3 targets nucleotides 308-330; SNCA4 targets nucleotides 231-251; SNCA5 targets nucleotides 356-376; SNCA6 targets nucleotides 261-279; SNCA7 targets nucleotides 403-421; SNCA8 targets nucleotides 451-469; SNCA9 targets nucleotides 1311-1329. Brackets flank the two alternative internal exons (exons 3 and 5).

FIG. 1B is the sequence of the full length protein of human SNCA (transcript variant NACP140; GenBankAccess. No. NM_000345; SEQ ID NO:2).

FIG. 8A is a polyacrylamide gel depicting a T1 mapping experiment of cleavage sites in Mayo7 (also called AL-DUP-1477) and Mayo8 (also called AL-DUP-1478) siRNAs. Lanes 1 are controls and represent siRNA incubated in T1 buffer; lanes 2 represent siRNA incubated in 1×T1 RNAse; lanes 3 represent siRNA incubated in 0.1×T1 RNAse; lanes 4 are an alkaline ladder; lanes 5 are Mayo7 and Mayo8, respectively, incubated in human serum for four hours; lanes 6 are Mayo7 and Mayo8, respectively, prior to incubation in human serum. *s indicates that the siRNA was 5' $^{32}$P-labeled on the sense strand by incubating with T4 Polynucleotide kinase and gamma-$^{32}$P-ATP.

FIG. 8B is an illustration of the sites of siRNA cleavage following the T1 RNAse assay. The cleavage sites include sites of T1 cleavage (3' of G) and cleavage from nucleases in the human serum.

FIG. 12A is a graph demonstrating the effect of siRNA on SNCA RNA expression in mouse brain tissue. E1, E2, and E3 represent results from three different mice injected with 2 uL of 200 uM Mayo-8s2m siRNA. C1, C2, and C3 represent results from three different mice injected with 2 uL phosphate buffered saline. Avg-E is the average α-synuclein/18S rRNA ratio of E1, E2, and E3. Avg-C is the average α-synuclein/18S rRNA ratio of the three control samples. The 18S rRNA control was amplified in an RT-PCR reaction performed in a separate tube from the α-synuclein RT-PCR reaction.

FIG. 12B is a graph demonstrating the effect of siRNA on SNCA RNA expression in the same mouse brain tissue described in FIG. 2A. In these RT-PCR reactions, the 18S rRNA control was amplified in an RT-PCR reaction performed in the same tube as the α-synuclein RT-PCR reaction.

DETAILED DESCRIPTION

Figure 2:
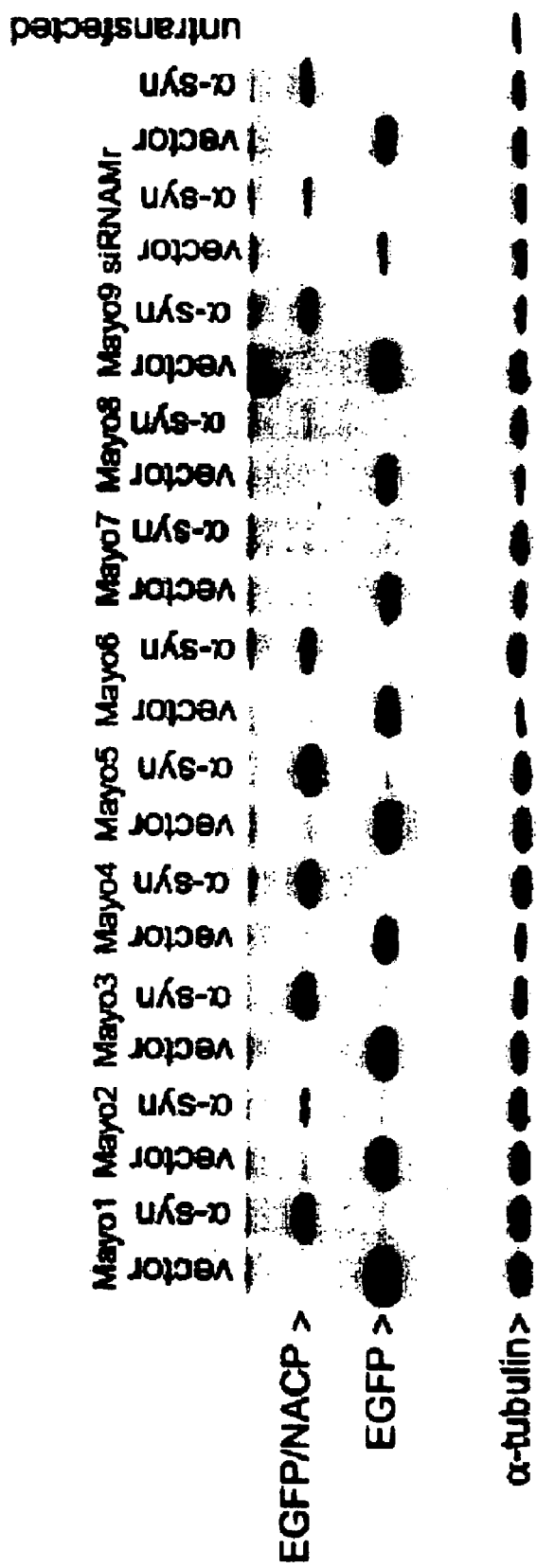
FIG. 2 is a Western blot of EGFP or EGFP/NACP fusion proteins expressed in BE(2)-M17 human neuroblastoma cells. The cells were cotransfected with a vector expressing EGFP or EGFP/NACP fusion protein and an siRNA listed in Table 1. In the figure, siRNAs Mayo1, Mayo2, Mayo3, Mayo4, Mayo5, Mayo6, Mayo7, Mayo8, and Mayo9, are equivalent to the siRNAs of Table 1 (SNCA1, SNCA2, SNCA3, SNCA4, SNCA5, SNCA6, SNCA7, SNCA8, and SNCA9, respectively). Control experiments included cotransfection of the EGFP and EGFP/NACP vectors with the siRNA Mr control dsRNA (vector and α-syn lanes labeled "siRNA Mr"), transfection of EGFP and EGFP/NACP vectors without dsRNA, and untransfected cells. The sequence of siRNA Mr is provided in Table 1.

Double-stranded (dsRNA) directs the sequence-specific silencing of mRNA through a process known as RNA interference (RNAi). The process occurs in a wide variety of organisms, including mammals and other vertebrates.

It has been demonstrated that 21-23 nt fragments of dsRNA are sequence-specific mediators of RNA silencing, e.g., by causing RNA degradation. While not wishing to be bound by theory, it may be that a molecular signal, which may be merely the specific length of the fragments, present in these 21-23 nt fragments, recruits cellular factors that mediate RNAi. Described herein are methods for preparing and administering these 21-23 nt fragments, and other iRNA agents, and their use for specifically inactivating gene function, and the function of the SNCA gene in particular. The use of iRNA agents (or recombinantly produced or chemically synthesized oligonucleotides of the same or similar nature) enables the targeting of specific mRNAs for silencing in mammalian cells. In addition, longer dsRNA agent fragments can also be used, e.g., as described below.

Although, in mammalian cells, long dsRNAs can induce the interferon response which is frequently deleterious, short dsRNAs (sRNAs) do not trigger the interferon response, at least not to an extent that is deleterious to the cell and host. In particular, the length of the iRNA agent strands in an sRNA agent can be less than 31, 30, 28, 25, or 23 nt, e.g., sufficiently short to avoid inducing a deleterious interferon response. Thus, the administration of a composition of sRNA agent (e.g., formulated as described herein) to a mammalian cell can be used to silence expression of a target gene while circumventing the interferon response. Further, use of a discrete species of iRNA agent can be used to selectively target one allele of a target gene, e.g., in a subject heterozygous for the allele.

Moreover, in one embodiment, a mammalian cell is treated with an iRNA agent that disrupts a component of the interferon response, e.g., dsRNA-activated protein kinase PKR. Such a cell can be treated with a second iRNA agent that includes a sequence complementary to a target RNA and that has a length that might otherwise trigger the interferon response.

As used herein, a "subject" refers to a mammalian organism undergoing treatment for a disorder mediated by SNCA expression. The subject can be a mammal such as a cow, horse, mouse, rat, dog, pig, goat, or a primate. In a preferred embodiment, the subject is a human.

As used herein, disorders associated with SNCA expression refers to any biological or pathological state that (1) is mediated in part by the presence of SNCA protein and (2) whose outcome can be affected by reducing the level of SNCA protein present. Specific disorders associated with SNCA expression are noted below.

Because iRNA agent mediated silencing can persist for several days after administering the iRNA agent composition, in many instances, it is possible to administer the composition with a frequency of less than once per day, or, for some instances, only once for the entire therapeutic regimen.

Alpha-synuclein

Alpha-synuclein protein is primarily found in the cytoplasm, but has also been localized to the nucleus. In dopaminergic neurons, alpha-synuclein is membrane bound. The protein is a soluble monomer normally localized at the presynaptic region of axons. The protein can form filamentous aggregates that are the major component of intracellular inclusions in neurodegenerative synucleinopathies.

Alpha-synuclein protein is associated with a number of diseases characterized by synucleinopathies. Three point mutations (A53T, A30P and E46K), and SNCA duplication and triplication events are linked to autosomal dominant Parkinson's disease (familial PD, also called FPD). The A53T and A30P mutations cause configuration changes in the SNCA protein that promote in vitro protofibril formation. The triplication event results in a two-fold overexpression of SNCA protein. Alpha-synuclein is a major fibrillar component of Lewy bodies, the cytoplasmic inclusions that are characteristic of FPD and idiopathic PD, and the substantia nigra of a Parkinson's disease brain is characterized by fibrillar alpha-synuclein. In Alzheimer's patients, SNCA peptides are a major component of amyloid plaques in the brains of patients with Alzheimer's disease.

Aggregation of alpha-synuclein in the cytoplasm of cells can be caused by a number of mechanisms, including overexpression of the protein, inhibition of protein degradation, or a mutation that affects the structure of the protein, resulting in an increased tendency of the protein to self-associate.

An SNCA gene product can be a target for treatment methods of neurodegenerative diseases such as PD. The treatment methods can include targeting of an SNCA nucleic acid with an iRNA agent. Alternatively, or additionally, an antisense RNA can be used to inhibit gene expression, or an antibody or small molecule can be used to target an SNCA nucleic acid. In general, an antisense RNA, anti-SNCA antibody, or small molecule can be used in place of an iRNA agent, e.g., by any of the methods or compositions described herein. A combination of therapies to downregulate SNCA expression and activity can also be used.

Sequencing of the SNCA gene has revealed common variants including a dinucleotide repeat sequence (REP1) within the promoter. REP1 varies in length across populations, and certain allelic variants are associated with an increased risk for PD (Krüger et al., Ann Neurol. 45:611-7, 1999). The SNCA gene REP1 locus is necessary for normal gene expression (Touchman et al., Genome Res. 11:78-86, 2001). SNCA gene expression levels among the different REP1 alleles varied significantly over a 3-fold range, suggesting that the association of specific genotypes with an increased risk for PD may be a consequence of SNCA gene over-expression (Chiba-Falek and Nussbaum, Hum Mol Genet. 10:3101-9, 2001). Functional analysis of intra-allelic variation at the SNCA gene REP1 locus implied that overall length of the allele plays the main role in transcriptional regulation; sequence heterogeneity is unlikely to confound genetic association studies based on alleles defined by length (Chiba-Falek et al., Hum Genet. 113:426-31, 2003). The recent discovery of SNCA gene triplication as a rare cause of PD is consistent with the observation that polymorphism within the gene promoter confers susceptibility via the same mechanism of gene over-expression (Singleton et al., Science 302:841, 2003).

Three splice variants of SNCA have been identified (see FIG. 1A). The full-length 140 amino acid protein is the most abundant form. A 128 amino acid form lacks exon 3, and a 112 amino acid form lacks exon 5. An iRNA of the invention can target any isoform of SNCA. An iRNA can target a common exon (e.g., exon 2, 4, 6, or 7) to effectively target all known isoforms. An iRNA agent can target a splice junction or an alternatively spliced exon to target specific isoforms. For example, to target the 112 amino acid isoform, an iRNA agent can target an mRNA sequence that overlaps the exon 4/exon 6 splice junction. To target the 128 amino acid protein isoform, an iRNA agent can target an mRNA sequence that overlaps the exon 2/exon 4 junction.

Treatment of Parkinson's Disease

Any patient having PD (or any other alpha-synuclein related disorder), is a candidate for treatment with a method or composition described herein. Preferably the patient is not terminally ill (e.g., the patient has life expectancy of two years or more), and preferably the patient has not reached end-stage Parkinson's disease (i.e., Hoehn and Yahr stage 5).

Presymptomatic subjects can also be candidates for treatment with an anti-SNCA agent, e.g., an anti-SNCA iRNA agent, antisense oligonucleotide, ribozyme, zinc finger protein, antibody, or small molecule. In one embodiment, a presymptomatic candidate is identified by either or both of risk-factor profiling and functional neuroimaging (e.g., by fluorodopa and positron emission tomography). For example, the candidate can be identified by risk-factor profiling followed by functional neuroimaging.

Individuals having any genotype are candidates for treatment. In some embodiments the patient will carry a particular genetic mutation that places the patient at increased risk for developing PD. For example, an individual carrying an SNCA gene multiplication, e.g., an SNCA gene duplication or triplication is at increased risk for developing PD and is a candidate for treatment with the iRNA agent. In addition, a gain-of-function mutation in SNCA can increase an individual's risk for developing PD. An individual carrying an SNCA REP1 genotype (e.g., a REP1 "+1 allele" heterozygous or homozygous genotype) can be a candidate for such treatment. An individual homozygous for the REP1 +1 allele overexpresses SNCA. An individual carrying a mutation in the UCHL-1, parkin, or SNCA gene is at increased risk for PD and can be a candidate for treatment with an anti-SNCA iRNA agent. Particularly, a mutation in the UCHL-1 or parkin gene will cause a decrease in gene or protein activity. An individual carrying a Tau genotype (e.g., a mutation in the Tau gene) or a Tau haplotype, such as the H1 haplotype is also at risk for developing PD. Other genetic risk factors include mutations in the MAPT, DJ1, PINK1, and NURR1 genes, and polymorphism in several genes including the SNCA, parkin, MAPT, and NAT2 genes.

Non-genetic (e.g., environmental) risk factors for PD include age (e.g., over age 30, 35, 40, 45, or 50 years), gender (men are generally have a higher risk than women), pesticide exposure, heavy metal exposure, and head trauma. In general, exogenous and endogenous factors that disrupt the ubiquitin proteasomal pathway or more specifically inhibit the proteasome, or which disrupt mitochondrial function, or which yield oxidative stress, or which promote the aggregation and fibrillization of alpha-synuclein, can increase the risk of an individual for developing PD, and can contribute to the pathogenesis of PD.

In one embodiment, an iRNA agent can be used to target wildtype SNCA in subjects with PD.

Treatment of Other Neurodegenerative Disorders

Any disease characterized by a synucleinopathy can be treated with an inhibitory agent described herein (e.g., an agent that targets SNCA), including Lewy body dementia, Multiple System Atrophy, and Alzheimer's Disease. Individuals having any genotype are candidates for treatment. In some embodiments, the patient will carry a particular genetic mutation that places them at increased risk for developing a synucleinopathy.

In one embodiment, an iRNA agent can be used to target wildtype SNCA in subjects with a neurodegenerative disorder.

An individual can develop a synucleinopathy as a result of certain environmental factors. For example, oxidative stress, certain pesticides (e.g., 24D and agent orange), bacterial infection, and head trauma have been linked to an increase in the risk of developing PD, and can be determining factors for determining the risk of an individual for synucleinopathies. These factors (and others disclosed herein) can be considered when evaluating the risk profile of a candidate subject for anti-SNCA therapy.

Design and Selection of iRNA Agents

Candidate iRNA agents can be designed by performing, for example, a gene walk analysis. Overlapping, adjacent, or closely spaced candidate agents corresponding to all or some of the transcribed region can be generated and tested. Each of the iRNA agents can be tested and evaluated for the ability to down regulate target gene expression (see below, "Evaluation of Candidate iRNA agents").

An iRNA agent can be rationally designed based on sequence information and desired characteristics. For example, an iRNA agent can be designed according to the relative melting temperature of the candidate duplex. Generally, the duplex will have a lower melting temperature at the 5' end of the antisense strand than at the 3' end of the antisense strand. This and other elements of rational design are discussed in greater detail below (see, e.g., sections labeled ""Palindromes," "Asymmetry," and "Z-X-Y," and "Differential Modification of Terminal Duplex Stability" and "Other-than-Watson-Crick Pairing."

An iRNA agent targeting an SNCA RNA can have the sequences of any of the siRNAs of Table 1. In particular, the iRNA agent can have the sequence of SNCA2, 7 (or 7s), or 8 (or 8s1 or 8s2), which were found to be the most effective for silencing the SNCA gene in vivo and in vitro.

Evaluation of Candidate iRNA Agents

A candidate anti-SNCA iRNA agent can be evaluated for its ability to down-regulate SNCA gene expression. For example, a candidate iRNA agent can be provided, and contacting with a cell that expresses the SNCA gene. The level of SNCA gene expression prior to and following contact with the candidate iRNA agent can be compared. The SNCA target gene can be an endogenous or exogenous gene within the cell. If it is determined that the amount of RNA or protein expressed from the SNCA gene is lower following contact with the iRNA agent, then it can be concluded that the iRNA agent downregulates SNCA gene expression. The level of SNCA RNA or protein in the cell can be determined by any method desired. For example, the level of SNCA RNA can be determined by Northern blot analysis, reverse transcription coupled with polymerase chain reaction (RT-PCR), or RNAse protection assay. The level of protein an be determined by, for example, Western blot analysis.

The iRNA agent can be tested in an in vitro or/and in an in vivo system. For example, the target gene or a fragment thereof can be fused to a reporter gene on a plasmid. The plasmid can be transfected into a cell with a candidate iRNA agent. The efficacy of the iRNA agent can be evaluated by monitoring expression of the reporter gene. The reporter gene can be monitored in vivo, such as by fluorescence or in situ hybridization. Exemplary fluorescent reporter genes include but are not limited to green fluorescent protein and luciferase. Expression of the reporter gene can also be monitored by Northern blot, RT-PCR, RNAse-protection assay, or Western blot analysis as described above.

Efficacy of an anti-SNCA iRNA agent can be tested in a mammalian cell line (e.g., a mammalian neural cell line), such as a human neuroblastoma cell line. For example, a cell line useful for testing efficacy of an anti-SNCA iRNA agent are those with a neuronal phenotype (neuroblastomas, neuronally differentiated phaeochromocytomas and primary neuronal cultures) or non neuronal cell lines (e.g. kidney, muscle or ovarian cells). Neuroblastoma cell lines include BE(2)-M17, SH-SY5Y (both human) and N2a (mouse). BE(2)-M17 cells biochemically mimic dopaminergic neurons of the human brain affected by alpha-synucleinopathies.

Controls include (1) testing the efficacy and specificity of an iRNA by assaying for a decrease in expression of the target gene by, for example, comparison to expression of an endogenous or exogenous off-target RNA or protein; and (2) testing specificity of the effect on target gene expression by administering a "nonfunctional" iRNA agent.

Nonfunctional control iRNA agents can (a) target a gene not expressed in the cell;

(b) be of nonsensical sequence (e.g., a scrambled version of the test iRNA); or (c) have a sequence complementary to the target gene, but be known by previous experiments to lack an ability to silence gene expression.

Assays include time course experiments to monitor stability and duration of silencing effect by an iRNA agent and monitoring in dividing versus nondividing cells. Presumably in dividing cells, the dsRNA is diluted out over time, thus decreasing the duration of the silencing effect. The implication is that dosage will have to be adjusted in vivo, and/or an iRNA agent will have to be administered more frequently to maintain the silencing effect. To monitor nondividing cells, cells can be arrested by serum withdrawal. Neurons are postmitotic cells, and thus neural cells are aptly suited for assaying the stability of iRNA agents, such as an anti-SNCA iRNA agent, for use in therapeutic compositions for the treatment of disorders of the nervous system, e.g., neurodegenerative disorders.

A candidate iRNA agent can also be evaluated for cross-species reactivity. For example, cell lines derived from different species (e.g., mouse vs. human) or in biological samples (e.g., serum or tissue extracts) isolated from different species can be transfected with a target iRNA agent and a candidate iRNA agent. The efficacy of the iRNA agent can be determined for the cell from the different species.

Stability Testing, Modification, and Retesting of iRNA Agents

A candidate iRNA agent can be evaluated with respect to its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject. The component (e.g., an exonuclease or endonuclease) can be specific for a particular area of the body, such as a particular tissue, organ, or bodily fluid (e.g., blood, plasma, or serum). Sites in an iRNA agent that are susceptible to cleavage, either by endonucleolytic or exonucleolytic cleavage, in certain areas of the body, may be resistant to cleavage in other areas of the body. An exemplary method includes:

(1) determining the point or points at which a substance present in the body of a subject, and preferably a component present in a compartment of the body into which a therapeutic dsRNA is to be introduced (this includes compartments into which the therapeutic is directly introduced, e.g., the circulation, as well as in compartments to which the therapeutic is eventually targeted; in some cases, e.g, the eye or the brain the two are the same), cleaves a dsRNA, e.g., an iRNA agent, and (2) identifying one or more points of cleavage, e.g., endonucleolytic, exonucleolytic, or both, in the dsRNA. Optionally, the method further includes providing an RNA modified to inhibit cleavage at such sites.

These steps can be accomplished by using one or more of the following assays:
  (i) (a) contacting a candidate dsRNA, e.g., an iRNA agent, with a test agent (e.g., a biological agent),
      (b) using a size-based assay, e.g., gel electrophoresis to determine if the iRNA agent is cleaved. In a preferred embodiment a time course is taken and a number of samples incubated for different times are applied to the size-based assay. In preferred embodiments, the candidate dsRNA is not labeled. The method can be a "stains all" method.
  (ii) (a) supplying a candidate dsRNA, e.g., an iRNA agent, which is radiolabeled;
       (b) contacting the candidate dsRNA with a test agent,
       (c) using a size-based assay, e.g., gel electrophoresis to determine if the iRNA agent is cleaved. In a preferred embodiment a time course is taken where a number of samples are incubated for different times and applied to the size-based assay. In preferred embodiments, the determination is made under conditions that allow determination of the number of nucleotides present in a fragment. E.g., an incubated sample is run on a gel having markers that allow assignment of the length of cleavage products. The gel can include a standard that is a "ladder" digestion. Either the sense or antisense strand can be labeled. Preferably only one strand is labeled in a particular experiment. The label can be incorporated at the 5' end, 3' end, or at an internal position. Length of a fragment (and thus the point of cleavage) can be determined from the size of the fragment based on the ladder and mapping using a site-specific endonuclease such as RNAse T1.
  (iii) fragments produced by any method, e.g., one of those above, can be analyzed by mass spectrometry. Following contacting the iRNA with the test agent, the iRNA can be purified (e.g., partially purified), such as by phenol-chloroform extraction followed by precipitation. Liquid chromatography can then be used to separate the fragments and mass spectrometry can be used to determine the mass of each fragment. This allows determination of the mechanism of cleavage, e.g., if by direct phosphate cleavage, such as be 5' or 3' exonuclease cleavage, or mediated by the 2'OH via formation of a cyclic phosphate.

More than one dsRNA, e.g., anti-SNCA iRNA agent, can be evaluated. The evaluation can be used to select a sequence for use in a therapeutic iRNA agent. For example, it allows the selection of a sequence having an optimal (usually minimized) number of sites that are cleaved by a substance(s), e.g., an enzyme, present in the relevant compartments of a subject's body. Two or more dsRNA candidates can be evaluated to select a sequence that is optimized. For example, two or more candidates can be evaluated and the one with optimum properties, e.g., fewer cleavage sites, selected.

The information relating to a site of cleavage can be used to select a backbone atom, a sugar or a base, for modification, e.g., a modification to decrease cleavage.

Exemplary modifications include modifications that inhibit endonucleolytic degradation, including the modifications described herein. Particularly favored modifications include: 2' modification, e.g., provision of a 2' OMe moiety on a U in a sense or antisense strand, but especially on a sense strand; modification of the backbone, e.g., with the replacement of an O with an S, in the phosphate backbone, e.g., the provision of a phosphorothioate modification, on the U or the A or both, especially on an antisense strand; replacement of the U with a C5 amino linker; replacement of an A with a G (sequence changes are preferred to be located on the sense strand and not the antisense strand); and modification of the at the 2', 6', 7', or 8' position. Preferred embodiments are those in which one or more of these modifications are present on the sense but not the antisense strand, or embodiments where the antisense strand has fewer of such modifications.

Exemplary modifications also include those that inhibit degradation by exonucleases. Examples of modifications that inhibit exonucleolytic degradation can be found herein. Particularly favored modifications include: 2' modification, e.g., provision of a 2' OMe moiety in a 3' overhang, e.g., at the 3' terminus (3' terminus means at the 3' atom of the molecule or at the most 3' moiety, e.g., the most 3' P or 2' position, as indicated by the context); modification of the backbone, e.g., with the replacement of a P with an S, e.g., the provision of a phosphorothioate modification, or the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidine in a 3' overhang, e.g., at the 3' terminus; modification with naproxen, ibuprofen, or other moieties which inhibit degradation at the 3' terminus.

These methods can be used to select and or optimize a therapeutic anti-SNCA iRNA agent.

The method can be used to evaluate a candidate dsRNA, e.g., a candidate iRNA agent, which is unmodified or which includes a modification, e.g., a modification that inhibits degradation, targets the dsRNA molecule, or modulates hybridization. Such modifications are described herein. A cleavage assay can be combined with an assay to determine the ability of a modified or non-modified candidate to silence the target. E.g., one might (optionally) test a candidate to evaluate its ability to silence a target (or off-target sequence), evaluate its susceptibility to cleavage, modify it (e.g., as described herein, e.g., to inhibit degradation) to produce a modified candidate, and test the modified candidate for one or both of the ability to silence and the ability to resist degradation. The procedure can be repeated. Modifications can be introduced one at a time or in groups. A cell-based method can be used to monitor the ability of the iRNA agent to silence. This can be followed by a different method, e.g, a whole animal method, to confirm activity.

A test agent refers to a biological agent, e.g., biological sample, tissue extract or prep, serum, a known enzyme or other molecule known to modify, e.g., cleave, a dsRNA, e.g., an endonuclease. The test agent can be in a compartment of the body in which the RNAi agent will be exposed. For example; for an iRNA agent that is administered directly in to neural tissue (e.g., into the brain or into the spinal cord) the test agent could be brain tissue extract or spinal fluid. An iRNA agent that is to be supplied directly to the eye can be incubated with an extract of the eye.

In Vivo Testing

An iRNA agent identified as being capable of inhibiting SNCA gene expression can be tested for functionality in vivo in an animal model (e.g., in a mammal, such as in mouse or rat). For example, the iRNA agent can be administered to an animal, and the iRNA agent evaluated with respect to its biodistribution, stability, and its ability to inhibit SNCA gene expression.

The iRNA agent can be administered directly to the target tissue, such as by injection, or the iRNA agent can be administered to the animal model in the same manner that it would be administered to a human. For example, the iRNA agent can be injected directly into a target region of the brain (e.g., into the cortex, the substantia nigra, the globus pallidus, or the hippocampus), and after a period of time, the brain can be harvested and tissue slices examined for distribution of the agent.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{32}P$, $^{33}P$, or $^3H$; gold particles; or antigen particles for immunohistochemistry).

An iRNA agent useful for monitoring biodistribution can lack gene silencing activity in vivo. For example, the iRNA agent can target a gene not present in the animal (e.g., an iRNA agent injected into mouse can target luciferase), or an iRNA agent can have a non-sense sequence, which does not target any gene, e.g., any endogenous gene). Localization/biodistribution of the iRNA can be monitored by a traceable label attached to the iRNA agent, such as a traceable agent described above The iRNA agent can be evaluated with respect to its ability to down regulate SNCA expression. Levels of SNCA expression in vivo can be measured, for example, by in situ hybridization, or by the isolation of RNA from tissue prior to and following exposure to the iRNA agent. SNCA RNA can be detected by any desired method, including but not limited to RT-PCR, Northern blot, or RNAase protection assay. Alternatively, or additionally, SNCA gene expression can be monitored by performing Western blot analysis on tissue extracts treated with the anti-SNCA iRNA agent.

An anti-SNCA iRNA agent can be tested in a mouse model for PD, such as a mouse carrying a wildtype copy of the human SNCA gene (Masliah et al., *Science* 287: 1265-1269, 2000) or in mouse carrying a mutant human SNCA (Richfield et al., *Exp. Neurol.* 175: 35-48, 2002; Giasson et al., *Neuron* 34: 521-533, 2002; Lee et al., *Proc Natl Acad. Sci.* 99: 8968-8973, 2002). The mutant mouse can carry a human SNCA gene that expresses an A53T, A30P, or E46K mutation. A treated mouse model can be observed for a decrease in symptoms associated with PD.

iRNA Chemistry

Described herein are isolated iRNA agents, e.g., RNA molecules, (double-stranded; single-stranded) that mediate RNAi. The iRNA agents preferably mediate RNAi with respect to an endogenous SNCA gene of a subject Generally, the iRNA agents of the instant invention include a region of sufficient complementarity to an SNCA RNA, and are of sufficient length in terms of nucleotides, such that the iRNA agent, or a fragment thereof, can mediate down regulation of the SNCA gene. It is not necessary that there be perfect complementarity between the iRNA agent and the target, but the correspondence must be sufficient to enable the iRNA agent, or a cleavage product thereof, to direct sequence specific silencing, e.g., by RNAi cleavage of an SNCA RNA.

Therefore, the iRNA agents featured in the instant invention include agents comprising a sense strand and antisense strand each comprising a sequence of at least 16, 17 or 18 nucleotides which is essentially identical, as defined below, to a sequence included in FIG. 1, including an SNCA sequence of Table 1, except that not more than 1, 2 or 3 nucleotides per strand, respectively, have been substituted by other nucleotides (e.g., adenosine replaced by uracil), while essentially retaining the ability to inhibit SNCA expression in a mammalian cell. These agents will therefore possess at least 15 nucleotides identical to a sequence of FIG. 1, but 1, 2 or 3 base mismatches with respect to either the target SNCA mRNA sequence or between the sense and antisense strand are introduced. Mismatches to the target SNCA mRNA sequence, particularly in the antisense strand, are most tolerated in the terminal regions and if present are preferably in a terminal region or regions, e.g., within 6, 5, 4, or 3 nucleotides of the 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the over all double strand character of the molecule.

Single stranded regions of an iRNA agent will often be modified or include nucleoside surrogates, e.g., the unpaired region or regions of a hairpin structure, e.g., a region which links two complementary regions, can have modifications or nucleoside surrogates. Modifications to stabilize one or both of the 3'- or 5'-terminus of an iRNA agent, e.g., against exonucleases, or to favor the antisense sRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. As discussed elsewhere herein, an iRNA agent will often be modified or include a ribose replacement monomer subunit (RRMS) in addition to the nucleotide surrogate. An RRMS replaces a ribose sugar on a ribonucleotide with another moiety, e.g., a non-carbohydrate (preferably cyclic) carrier. RRMS' are described in greater detail below.

Although, in mammalian cells, long ds iRNA agents can induce the interferon response which is frequently deleterious, short ds iRNA agents do not trigger the interferon response, at least not to an extent that is deleterious to the cell and host. The iRNA agents of the present invention include molecules which are sufficiently short that they do not trigger the interferon response in mammalian cells. Thus, the administration of a composition of an iRNA agent (e.g., formulated as described herein) to a mammalian cell can be used to silence expression of the SNCA gene while circumventing the interferon response. Molecules that are short enough that they do not trigger an interferon response are termed sRNA agents or shorter iRNA agents herein. "sRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60 but preferably less than 50, 40, or 30 nucleotide pairs.

In addition to homology to target RNA and the ability to down regulate a target gene, an iRNA agent will preferably have one or more of the following properties:

(1) it will be of the Formula 1, 2, 3, or 4 set out in the RNA Agent section below;

(2) if single stranded it will have a 5' modification which includes one or more phosphate groups or one or more analogs of a phosphate group;

(3) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;

(4) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an iRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into H-bonding which is more characteristic of the OH moiety of a ribonucleotide than the H moiety of a deoxyribonucleotide. A preferred iRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure. These limitations are particularly preferably in the antisense strand;

(5) regardless of the nature of the modification, and even though the RNA agent can contain deoxynucleotides or modified deoxynucleotides, particularly in overhang or other single strand regions, it is preferred that DNA molecules, or any molecule in which more than 50, 60, or 70% of the nucleotides in the molecule, or more than 50, 60, or 70% of the nucleotides in a duplexed region are deoxyribonucleotides, or modified deoxyribonucleotides which are deoxy at the 2' position, are excluded from the definition of RNA agent.

A "single strand iRNA agent" as used herein, is an iRNA agent which is made up of a single molecule. It may include a duplexed region, formed by intra-strand pairing, e.g., it may be, or include, a hairpin or panhandle structure. Single strand iRNA agents are preferably antisense with regard to the target molecule. In preferred embodiments single strand iRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-). (These modifications can also be used with the antisense strand of a double stranded iRNA.)

A "ds iRNA agent" (abbreviation for "double stranded iRNA agent") as used herein, is an iRNA agent which includes more than one, and preferably two, strands in which interchain hybridization can form a region of duplex structure.

The antisense strand of a double stranded iRNA agent should be equal to or at least, 14, 15, 16 17, 18, 19, 25, 29, 40, or 50 nucleotides in length. It should be equal to or less than 60, 50, 40, or 30, nucleotides in length. Preferred ranges are 15 to 30, 17 to 25, 19 to 23, and 19 to 21 nucleotides in length.

The sense strand of a double stranded iRNA agent should be equal to or at least 14, 15, 16, 17, 18, 19, 25, 29, 40, or 50 nucleotides in length. It should be equal to or less than 60, 50, 40, or 30, nucleotides in length. Preferred ranges are 15 to 30, 17 to 25, 19 to 23, and 19 to 21 nucleotides in length.

The double strand portion of a double stranded iRNA agent should be equal to or at least, 15, 16, 17, 18, 19, 20, 21, 22, 23, 24, 25, 29, 40, or 50 nucleotide pairs in length. It should be equal to or less than 60, 50, 40, or 30, nucleotides pairs in length. Preferred ranges are 15 to 30, 17 to 25, 19 to 23, and 19 to 21 nucleotides pairs in length.

It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active sRNA/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional sRNA 5'-end. Antisense strand modifications include 5' phosphorylation as well as any of the other 5' modifications discussed herein, particularly the 5' modifications discussed above in the section on single stranded iRNA molecules.

It is preferred that the sense and antisense strands be chosen such that the ds iRNA agent includes a single strand or unpaired region at one or both ends of the molecule. Thus, a ds iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred iRNA agents will have single-stranded overhangs, preferably 3' overhangs, of 1 to 4, or preferably 2 or 3 nucleotides in length at each end. The overhangs can be the result of one strand being longer than the other, or the result of two strands of the same length being staggered. 5' ends are preferably phosphorylated.

Preferred lengths for the duplexed region is between 15 and 30, most preferably 18, 19, 20, 21, 22, and 23 nucleotides in length, e.g., in the iRNA agent range discussed above. iRNA agents can resemble in length and structure the natural Dicer processed products from long dsRNAs. Embodiments in which the two strands of the sRNA agent are linked, e.g., covalently linked are also included. Hairpin, or other single strand structures which provide the required double stranded region, and preferably a 3' overhang are also within the invention.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element. While not wishing to be bound by theory, it is believed that silencing by the agents described herein uses the RNAi machinery or process and a guide RNA, e.g., an iRNA agent of 15 to 30 nucleotide pairs.

As used herein, the term "complementary" is used to indicate a sufficient degree of complementarity such that stable and specific binding occurs between a compound of the invention and a target RNA molecule, e.g., an SNCA mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target SCNA mRNA) if the iRNA agent reduces the production of a protein encoded by the target RNA in a cell. The iRNA agent may also be "exactly complementary" (excluding the RRMS containing subunit(s)) to the target RNA, e.g., the target RNA and the iRNA agent anneal, preferably to form a hybrid made exclusively of Watson-Crick basepairs in the region of exact complementarity. A "sufficiently complementary" target RNA can include an internal region (e.g., of at least 10 nucleotides) that is exactly complementary to a target SNCA RNA. Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference. Preferred iRNA agents will be based on or consist of or comprise the SNCA sense and antisense sequences provided in Table 1 and/or sequences illustrated in FIG. 1.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because the are typically the result of a post transcriptionally modification) are within the term unmodified RNA, as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Much of the discussion below refers to single strand molecules. In many embodiments of the invention a ds iRNA agent, e.g., a partially double stranded iRNA agent, is required or preferred. Thus, it is understood that double stranded structures (e.g. where two separate molecules are contacted to form the double stranded region or where the double stranded region is formed by intramolecular pairing (e.g., a hairpin structure)) made of the single stranded structures described below are within the invention. Preferred lengths are described elsewhere herein.

As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand. In some embodiments it is particularly preferred, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications and nucleotide surrogates are discussed below.

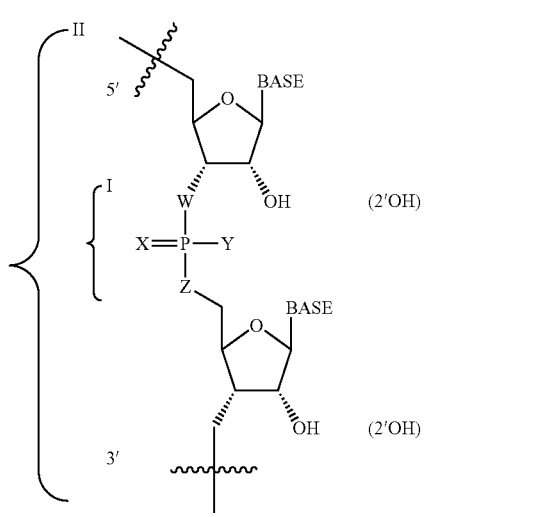

FORMULA 1

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases. Unmodified oligoribonucleotides may also be less than optimal in terms of offering tethering points for attaching ligands or other moieties to an iRNA agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g. a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., $-(CH_2)_n-$, $-(CH_2)_nN-$, $-(CH_2)_nO-$, $-(CH_2)_nS-$, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)litho-cholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in preferred embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Evaluation of iRNA Agents

One can evaluate a candidate iRNA agent, e.g., a modified iRNA agent. A general approach is described below, but methods more specific to SNCA iRNA agents are discussed elsewhere herein. In general, one can test for a selected property by exposing the agent or modified molecule and a control molecule to the appropriate conditions and evaluating for the presence of the selected property. For example, resistance to a degradent can be evaluated as follows. A candidate modified RNA (and preferably a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified siRNA homologous to the GFP mRNA can be assayed for the ability to inhibit GFP expression by monitoring for a decrease in cell fluorescence, as compared to a control cell, in which the transfection did not include the candidate siRNA, e.g., controls with no agent added and/or controls with a non-modified RNA added. Efficacy of the candidate agent on gene expression can be assessed by comparing cell fluorescence in the presence of the modified and unmodified iRNA agents.

The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added and/or cells in which a non-modified RNA is added.

Preferred iRNA Agents

Preferred RNA agents have the following structure (see Formula 2 below):

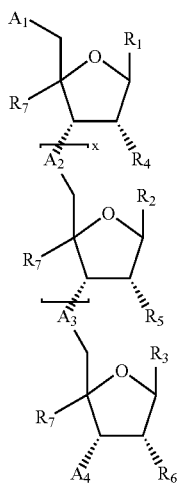

FORMULA 2

Referring to Formula 2 above, $R^1$, $R^2$, and $R^3$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl) uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N-6-isopentyladenine, N-methylguanines, or O-alkylated bases.

$R^4$, $R^5$, and $R^6$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_m$ $CH_2CH_2NHR^9$; $NHC(O)R^8$; cyano; mercapto, $SR^8$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; or $R^4$, $R^5$, or $R^6$ together combine with $R^7$ to form an [—O—$CH_2$—] covalently bound bridge between the sugar 2' and 4' carbons.

$A^1$ is:

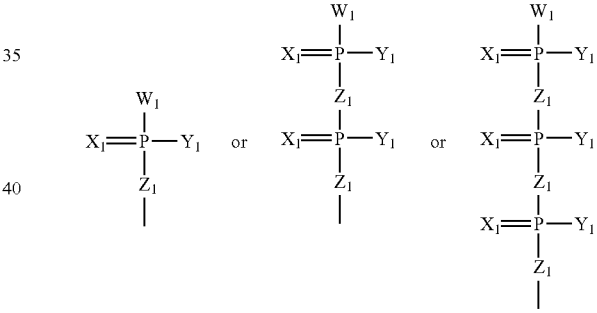

; H; OH; $OCH_3$; $W^1$; an abasic nucleotide; or absent;

(a preferred A1, especially with regard to anti-sense strands, is chosen from 5'-monophosphate $((HO)_2(O)P$—O—5')$, 5'-diphosphate $((HO)_2(O)P$—O—$P(HO)(O)$—O-5')$, 5'-triphosphate $((HO)_2(O)P$—O—$(HO)(O)P$—O—$P(HO)(O)$—O-5')$, 5'-guanosine cap (7-methylated or non-methylated) (7m-G-O-5'-$(HO)(O)P$—O—$(HO)(O)P$—O—$P(HO)(O)$—O-5')$, 5'-adenosine cap (Appp), and any modified or unmodified nucleotide cap structure (N—O-5'-$(HO)(O)P$—O—$(HO)(O)P$—O—$P(HO)(O)$—O-5')$, 5'-monothiophosphate (phosphorothioate; $(HO)_2(S)P$—O-5')$, 5'-monodithiophosphate (phosphorodithioate; $(HO)(HS)(S)P$—O-5')$, 5'-phosphorothiolate $((HO)_2(O)P$—S-5')$; any additional combination of oxygen/sulfur replaced monophosphate, diphosphate and triphosphates (e.g. 5'-alpha-thiotriphosphate, 5'-gamma-thiotriphosphate, etc.), 5'-phosphoramidates $((HO)_2(O)P$—NH-5', $(HO)(NH_2)(O)P$—O-5')$, 5'-alkylphosphonates (R=alkyl=methyl, ethyl, isopropyl, propyl, etc., e.g. $RP(OH)(O)$—O-5'-, $(OH)_2(O)P$-5'-$CH_2$—), 5'-alkyletherphosphonates (R=alkylether-methoxymethyl ($MeOCH_2$—), ethoxymethyl, etc., e.g. $RP(OH)(O)$—O-5'-)).

$A^2$ is:

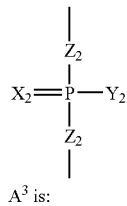

$A^3$ is:

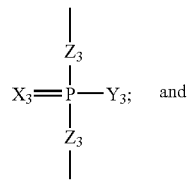 and $A^4$ is:

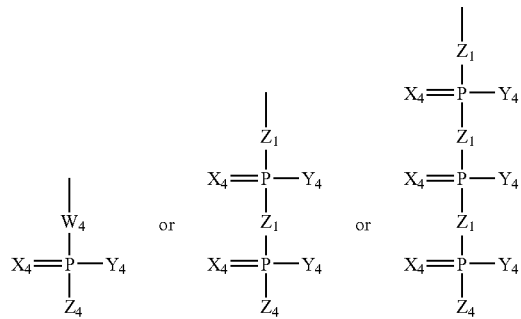

; H; $Z^4$; an inverted nucleotide; an abasic nucleotide; or absent.

$W^1$ is OH, $(CH_2)_n R^{10}$, $(CH_2)_n NHR^{10}$, $(CH_2)_n OR^{10}$, $(CH_2)_n SR^{10}$; $O(CH_2)_n R^{10}$; $O(CH_2)_n OR^{10}$, $O(CH_2)_n NR^{10}$, $O(CH_2)_n SR^{10}$; $O(CH_2)_n SS(CH_2)_n OR^{10}$, $O(CH_2)_n C(O) OR^{10}$, $NH(CH_2)_n R^{10}$; $NH(CH_2)_n NR^{10}$; $NH(CH_2)_n OR^{10}$, $NH(CH_2)_n SR^{10}$; $S(CH_2)_n R^{10}$, $S(CH_2)_n NR^{10}$, $S(CH_2)_n OR^{10}$, $S(CH_2)_n SR^{10}$ $O(CH_2CH_2O)_m CH_2CH_2OR^{10}$; $O(CH_2CH_2O)_m CH_2CH_2NHR^{10}$, $NH(CH_2CH_2NH)_m CH_2CH_2NHR^{10}$; $Q-R^{10}$, $O-Q-R^{10}$ $N-Q-R^{10}$, $S-Q-R^{10}$ or —O—. $W^4$ is O, $CH_2$, NH, or S.

$X^1$, $X^2$, $X^3$, and $X^4$ are each, independently, O or S.

$Y^1$, $Y^2$, $Y^3$, and $Y^4$ are each, independently, OH, O$^-$, OR$^8$, S, Se, BH$_3^-$, H, NHR$^9$, N(R$^9$)$_2$ alkyl, cycloalkyl, aralkyl, aryl, or heteroaryl, each of which may be optionally substituted.

$Z^1$, $Z^2$, and $Z^3$ are each independently O, $CH_2$, NH, or S. $Z^4$ is OH, $(CH_2)_n R^{10}$, $(CH_2)_n NHR^{10}$, $(CH_2)_n OR^{10}$, $(CH_2)_n SR^{10}$; $O(CH_2)_n R^{10}$; $O(CH_2)_n OR^{10}$, $O(CH_2)_n NR^{10}$, $O(CH_2)_n SR^{10}$, $O(CH_2)_n SS(CH_2)_n OR^{10}$, $O(CH_2)_n C(O)OR^{10}$; $NH(CH_2)_n R^{10}$; $NH(CH_2)_n NR^{10}$; $NH(CH_2)_n OR^{10}$, $NH(CH_2)_n SR^{10}$; $S(CH_2)_n R^{10}$, $S(CH_2)_n NR^{10}$, $S(CH_2)_n OR^{10}$, $S(CH_2)_n SR^{10}$ $O(CH_2CH_2O)_m CH_2CH_2OR^{10}$, $O(CH_2CH_2O)_m CH_2CH_2NHR^{10}$, $NH(CH_2CH_2NH)_m CH_2CH_2NHR^{10}$; $Q-R^{10}$, $O-Q-R^{10}$ $N-Q-R^{10}$, $S-Q-R^{10}$.

x is 5-100, chosen to comply with a length for an RNA agent described herein.

$R^7$ is H; or is together combined with $R^4$, $R^5$, or $R^6$ to form an [—O—CH$_2$—] covalently bound bridge between the sugar 2' and 4' carbons.

$R^8$ is alkyl, cycloalkyl, aryl, aralkyl, heterocyclyl, heteroaryl, amino acid, or sugar; $R^9$ is NH$_2$, alkylamino, dialkylamino, heterocyclyl, arylamino, diaryl amino, heteroaryl amino, diheteroaryl amino, or amino acid; and $R^{10}$ is H; fluorophore (pyrene, TAMRA, fluorescein, Cy3 or Cy5 dyes); sulfur, silicon, boron or ester protecting group; intercalating agents (e.g. acridines), cross-linkers (e.g. psoralene, mitomycin C), porphyrins (TPPC4,texaphyrin, Sapphyrin), polycyclic aromatic hydrocarbons (e.g., phenazine, dihydrophenazine), artificial endonucleases (e.g. EDTA), lipophilic carriers (cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino; alkyl, cycloalkyl, aryl, aralkyl, heteroaryl; radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles); or an RNA agent. m is 0-1,000,000, and n is 0-20. Q is a spacer selected from the group consisting of abasic sugar, amide, carboxy, oxyamine, oxyimine, thioether, disulfide, thiourea, sulfonamide, or morpholino, biotin or fluorescein reagents.

Preferred RNA agents in which the entire phosphate group has been replaced have the following structure (see Formula 3 below):

FORMULA 3

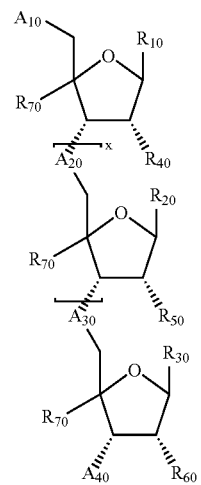

Referring to Formula 3, $A^{10}$-$A^{40}$ is L-G-L; $A^{10}$ and/or $A^{40}$ may be absent, in which L is a linker, wherein one or both L may be present or absent and is selected from the group consisting of $CH_2(CH_2)_g$; $N(CH_2)_g$; $O(CH_2)_g$; $S(CH_2)_g$. G is a functional group selected from the group consisting of siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

$R^{10}$, $R^{20}$, and $R^{30}$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N-6-isopentenyladenine, N-methylguanines, or O-alkylated bases.

$R^{40}$, $R^{50}$, and $R^{60}$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2R^9$; $NHC(O)R^8$; cyano; mercapto, $SR^7$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, and ureido groups; or $R^{40}$, $R^{50}$, or $R^{60}$ together combine with $R^{70}$ to form an [—O—$CH_2$—] covalently bound bridge between the sugar 2' and 4' carbons.

x is 5-100 or chosen to comply with a length for an RNA agent described herein.

$R^{70}$ is H; or is together combined with $R^{40}$, $R^{50}$, or $R^{60}$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; and $R^9$ is $NH_2$, alkylamino, dialkylamino, heterocyclyl, arylamino, diaryl amino, heteroaryl amino, diheteroaryl amino, or amino acid. m is 0-1,000,000, n is 0-20, and g is 0-2.

Preferred nucleoside surrogates have the following structure (see Formula 4 below):

FORMULA 4

S is a nucleoside surrogate selected from the group consisting of mophilino, cyclobutyl, pyrrolidine and peptide nucleic acid. L is a linker and is selected from the group consisting of $CH_2(CH_2)_g$; $N(CH_2)_g$; $O(CH_2)_g$; $S(CH_2)_g$; —$C(O)(CH_2)_n$— or may be absent. M is an amide bond; sulfonamide; sulfinate; phosphate group; modified phosphate group as described herein; or may be absent.

$R^{100}$, $R^{200}$, and $R^{300}$ are each, independently, H (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1,2,4,-triazoles, 2-pyridinones, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N-6-isopentenyladenine, N-methylguanines, or O-alkylated bases.

x is 5-100, or chosen to comply with a length for an RNA agent described herein; and g is 0-2.

Nuclease Resistant Monomers

An RNA, e.g., an iRNA agent, can incorporate a nuclease resistant monomer (NRM). For example, the invention includes an iRNA agent described herein, e.g., a palindromic iRNA agent, an iRNA agent having a non canonical pairing, an iRNA agent which targets a gene described herein, e.g., an SNCA gene, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates an NRM.

An iRNA agent can include monomers which have been modified so as to inhibit degradation, e.g., by nucleases, e.g., endonucleases or exonucleases, found in the body of a subject. These monomers are referred to herein as NRMs, or nuclease resistance promoting monomers or modifications. In many cases these modifications will modulate other properties of the iRNA agent as well, e.g., the ability to interact with a protein, e.g., a transport protein, e.g., serum albumin, or a member of the RISC(RNA-induced Silencing Complex), or the ability of the first and second sequences to form a duplex with one another or to form a duplex with another sequence, e.g., a target molecule.

While not wishing to be bound by theory, it is believed that modifications of the sugar, base, and/or phosphate backbone in an iRNA agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the iRNA agent prior to interaction with the RISC complex, but at the same time do not render the iRNA agent resistant to endonuclease activity in the RISC complex. Again, while not wishing to be bound by any theory, it is believed that placement of the modifications at or near the 3' and/or 5' end of antisense strands can result in iRNA agents that meet the preferred nuclease resistance criteria delineated above. Again, still while not wishing to be bound by any theory, it is believed that placement of the modifications at e.g., the middle of a sense strand can result in iRNA agents that are relatively less likely to undergo off-targeting.

Modifications described herein can be incorporated into any double-stranded RNA and RNA-like molecule described herein, e.g., an iRNA agent. An iRNA agent may include a duplex comprising a hybridized sense and antisense strand, in which the antisense strand and/or the sense strand may include one or more of the modifications described herein. The antisense strand may include modifications at the 3' end and/or the 5' end and/or at one or more positions that occur 1-6 (e.g., 1-5, 1-4, 1-3, 1-2) nucleotides from either end of the strand. The sense strand may include modifications at the 3' end and/or the 5' end and/or at any one of the intervening positions between the two ends of the strand. The iRNA agent may also include a duplex comprising two hybridized antisense strands. The first and/or the second antisense strand may include one or more of the modifications described herein. Thus, one and/or both antisense strands may include modifications at the 3' end and/or the 5' end and/or at one or more positions that occur 1-6 (e.g., 1-5, 1-4, 1-3, 1-2) nucleotides from either end of the strand. Particular configurations are discussed below.

Modifications that can be useful for producing iRNA agents that meet the preferred nuclease resistance criteria delineated above can include one or more of the following chemical and/or stereochemical modifications of the sugar, base, and/or phosphate backbone:

(i) chiral (Sp) thioates. Thus, preferred NRMs include nucleotide dimers with an enriched or pure for a particular chiral form of a modified phosphate group containing a heteroatom at the nonbridging position, e.g., Sp or Rp, at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include monomers at the terminal position derivatized at a cationic group. As the 5' end of an antisense sequence should have a terminal —OH or phosphate group this NRM is preferably not used at the 5' end of an anti-sense sequence. The group should be attached at a position on the base which minimizes interference with H bond formation and hybridization, e.g., away form the face which interacts with the complementary base on the other strand, e.g, at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' $CH_2$-$NCH_3$—O—$CH_2$-5' and 3' $CH_2$—NH—(O=)—$CH_2$-5';

(iv) 3'-bridging thiophosphates and 5'-bridging thiophosphates. Thus, preferred NRM's can includd these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(vi) conjugate groups. Thus, preferred NRM's can include, e.g., a targeting moiety or a conjugated ligand described herein conjugated with the monomer, e.g., through the sugar, base, or backbone;

(vi) abasic linkages. Thus, preferred NRM's can include an abasic monomer, e.g., an abasic monomer as described herein (e.g., a nucleobaseless monomer); an aromatic or heterocyclic or polyheterocyclic aromatic monomer as described herein; and (vii) 5'-phosphonates and 5'-phosphate prodrugs. Thus, preferred NRM's include monomers, preferably at the terminal position, e.g., the 5' position, in which one or more atoms of the phosphate group is derivatized with a protecting group, which protecting group or groups, are removed as a result of the action of a component in the subject's body, e.g, a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent. As some NRMs interfere with hybridization the total number incorporated, should be such that acceptable levels of iRNA agent duplex formation are maintained.

In some embodiments NRM modifications are introduced into the terminal cleavage site or in the cleavage region of a sequence (a sense strand or sequence) which does not target a desired sequence or gene in the subject. This can reduce off-target silencing.

Chiral $S_P$ Thioates

A modification can include the alteration, e.g., replacement, of one or both of the non-linking (X and Y) phosphate oxygens- and/or of one or more of the linking (W and Z) phosphate oxygens. Formula X below depicts a phosphate moiety linking two sugar/sugar surrogate-base moieties, $SB_1$ and $SB_2$.

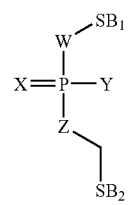

FORMULA X

In certain embodiments, one of the non-linking phosphate oxygens in the phosphate backbone moiety (X and Y) can be replaced by any one of the following: S, Se, $BR_3$ (R is hydrogen, alkyl, aryl, etc.), C (i.e., an alkyl group, an aryl group, etc.), H, $NR_2$ (R is hydrogen, alkyl, aryl, etc.), or OR (R is alkyl or aryl). The phosphorus atom in an unmodified phosphate group is achiral. However, replacement of one of the non-linking oxygens with one of the above atoms or groups of atoms renders the phosphorus atom chiral; in other words a phosphorus atom in a phosphate group modified in this way is a stereogenic center. The stereogenic phosphorus atom can possess either the "R" configuration (herein $R_P$) or the "S" configuration (herein Sp). Thus if 60% of a population of stereogenic phosphorus atoms have the $R_P$ configuration, then the remaining 40% of the population of stereogenic phosphorus atoms have the $S_P$ configuration.

In some embodiments, iRNA agents, having phosphate groups in which a phosphate non-linking oxygen has been replaced by another atom or group of atoms, may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the $S_P$ configuration. Alternatively, iRNA agents having phosphate groups in which a phosphate non-linking oxygen has been replaced by another atom or group of atoms may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the $R_P$ configuration. In other embodiments, the population of stereogenic phosphorus atoms may have the $S_P$ configuration and may be substantially free of stereogenic phosphorus atoms having the $R_P$ configuration. In still other embodiments, the population of stereogenic phosphorus atoms may have the $R_P$ configuration and may be substantially free of stereogenic phosphorus atoms having the $S_P$ configuration. As used herein, the phrase "substantially free of stereogenic phosphorus atoms having the $R_P$ configuration" means that moieties containing stereogenic phosphorus atoms having the $R_P$ configuration cannot be detected by conventional methods known in the art (chiral HPLC, $^1$H NMR analysis using chiral shift reagents, etc.). As used herein, the phrase "substantially free of stereogenic phosphorus atoms having the $S_P$ configuration" means that moieties containing stereogenic phosphorus atoms having the $S_P$ configuration cannot be detected by conventional methods known in the art (chiral HPLC, $^1$H NMR analysis using chiral shift reagents, etc.).

In a preferred embodiment, modified iRNA agents contain a phosphorothioate group, i.e., a phosphate groups in which a phosphate non-linking oxygen has been replaced by a sulfur atom. In an especially preferred embodiment, the population of phosphorothioate stereogenic phosphorus atoms may have the $S_P$ configuration and be substantially free of stereogenic phosphorus atoms having the $R_P$ configuration.

Phosphorothioates may be incorporated into iRNA agents using dimers e.g., formulas X-1 and X-2. The former can be used to introduce phosphorothioate

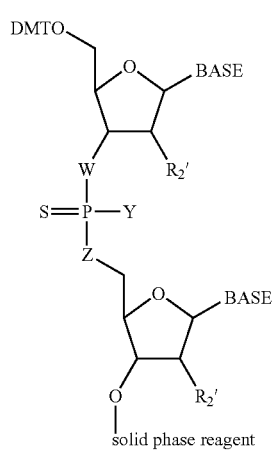

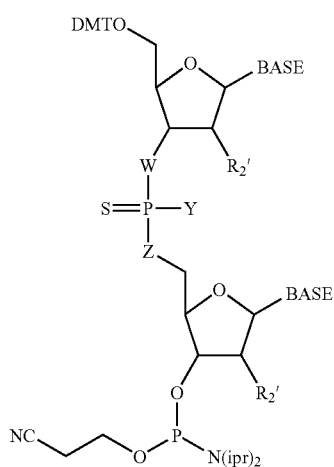

at the 3' end of a strand, while the latter can be used to introduce this modification at the 5' end or at a position that occurs e.g., 1, 2, 3, 4, 5, or 6 nucleotides from either end of the strand. In the above formulas, Y can be 2-cyanoethoxy, W and Z can be O, $R_{2'}$ can be, e.g., a substituent that can impart the C-3 endo configuration to the sugar (e.g., OH, F, $OCH_3$), DMT is dimethoxytrityl, and "BASE" can be a natural, unusual, or a universal base.

X-1 and X-2 can be prepared using chiral reagents or directing groups that can result in phosphorothioate-containing dimers having a population of stereogenic phosphorus atoms having essentially only the $R_P$ configuration (i.e., being substantially free of the $S_P$ configuration) or only the $S_P$ configuration (i.e., being substantially free of the $R_P$ configuration). Alternatively, dimers can be prepared having a population of stereogenic phosphorus atoms in which about 50% of the atoms have the $R_P$ configuration and about 50% of the atoms have the $S_P$ configuration. Dimers having stereogenic phosphorus atoms with the $R_P$ configuration can be identified and separated from dimers having stereogenic phosphorus atoms with the $S_P$ configuration using e.g., enzymatic degradation and/or conventional chromatography techniques.

Cationic Groups

Modifications can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino).

Nonphosphate Linkages

Modifications can also include the incorporation of nonphosphate linkages at the 5' and/or 3' end of a strand. Examples of nonphosphate linkages which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methyl phosphonate and hydroxylamino groups.

3'-bridging Thiophosphates and 5'-bridging Thiophosphates; Locked-RNA, 2'-5' Linkages, Inverted Linkages, α-nucleosides; Conjugate Groups; Abasic Linkages; and 5'-phosphonates and 5'-phosphate Prodrugs Referring to formula X above, modifications can include replacement of one of the bridging or linking phosphate oxygens in the phosphate backbone moiety (W and Z). Unlike the situation where only one of X or Y is altered, the phosphorus center in the phosphorodithioates is achiral which precludes the formation of iRNA agents containing a stereogenic phosphorus atom.

Modifications can also include linking two sugars via a phosphate or modified phosphate group through the 2' position of a first sugar and the 5' position of a second sugar. Also contemplated are inverted linkages in which both a first and second sugar are each linked through the respective 3' positions. Modified RNA's can also include "abasic" sugars, which lack a nucleobase at C-1'. The sugar group can also contain one or more carbons that possess the opposite stereochemical configuration than that of the corresponding carbon in ribose. Thus, a modified iRNA agent can include nucleotides containing e.g., arabinose, as the sugar. In another subset of this modification, the natural, unusual, or universal base may have the α-configuration. Modifications can also include L-RNA.

Modifications can also include 5'-phosphonates, e.g., P(O)(O$^-$)$_2$—X—C$^{5'}$-sugar (X=CH2, CF2, CHF and 5'-phosphate prodrugs, e.g., P(O)[OCH2CH2SC(O)R]$_2$CH$_2$C$^{5'}$-sugar. In the latter case, the prodrug groups may be decomposed via reaction first with carboxy esterases. The remaining ethyl thiolate group via intramolecular S$_N$2 displacement can depart as episulfide to afford the underivatized phosphate group.

Modification can also include the addition of conjugating groups described elsewhere herein, which are preferably attached to an iRNA agent through any amino group available for conjugation.

Nuclease resistant modifications include some which can be placed only at the terminus and others which can go at any position. Generally the modifications that can inhibit hybridization so it is preferably to use them only in terminal regions, and preferable to not use them at the cleavage site or in the cleavage region of an sequence which targets a subject sequence or gene. The can be used anywhere in a sense sequence, provided that sufficient hybridization between the two sequences of the iRNA agent is maintained. In some embodiments it is desirable to put the NRM at the cleavage site or in the cleavage region of a sequence which does not target a subject sequence or gene, as it can minimize off-target silencing.

In addition, an iRNA agent described herein can have an overhang which does not form a duplex structure with the other sequence of the iRNA agent—it is an overhang, but it does hybridize, either with itself, or with another nucleic acid, other than the other sequence of the iRNA agent.

In most cases, the nuclease-resistance promoting modifications will be distributed differently depending on whether the sequence will target a sequence in the subject (often referred to as an anti-sense sequence) or will not target a sequence in the subject (often referred to as a sense sequence). If a sequence is to target a sequence in the subject, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt guide RNA, or about 10 or 11 nucleotides upstream of the first nucleotide which is complementary to the guide sequence. As used herein cleavage site refers to the nucleotide on either side of the cleavage site, on the target or on the iRNA agent strand which hybridizes to it. Cleavage region means an nucleotide with 1, 2, or 3 nucleotides of the cleave site, in either direction.)

Such modifications can be introduced into the terminal regions, e.g., at the terminal position or with 2, 3, 4, or 5 positions of the terminus, of a sequence which targets or a sequence which does not target a sequence in the subject.

An iRNA agent can have a first and a second strand chosen from the following:

a first strand which does not target a sequence and which has an NRM modification at or within 1, 2, 3, 4, 5, or 6 positions from the 3' end;

a first strand which does not target a sequence and which has an NRM modification at or within 1, 2, 3, 4, 5, or 6 positions from the 5' end;

a first strand which does not target a sequence and which has an NRM modification at or within 1, 2, 3, 4, 5, or 6 positions from the 3' end and which has a NRM modification at or within 1, 2, 3, 4, 5, or 6 positions from the 5' end;

a first strand which does not target a sequence and which has an NRM modification at the cleavage site or in the cleavage region;

a first strand which does not target a sequence and which has an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end; and a second strand which targets a sequence and which has an NRM modification at or within 1, 2, 3, 4, 5, or 6 positions from the 3' end;

a second strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a second strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a second strand which targets a sequence and which preferably does not have an NRM modification at the cleavage site or in the cleavage region;

a second strand which targets a sequence and which does not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand).

An iRNA agent can also target two sequences and can have a first and second strand chosen from:

a first strand which targets a sequence and which has an NRM modification at or within 1, 2, 3, 4, 5, or 6 positions from the 3' end;

a first strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a first strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a first strand which targets a sequence and which preferably does not have an NRM modification at the cleavage site or in the cleavage region;

a first strand which targets a sequence and which dose not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand) and a second strand which targets a sequence and which has an NRM modification at or within 1, 2, 3, 4, 5, or 6 positions from the 3' end;

a second strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a second strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a second strand which targets a sequence and which preferably does not have an NRM modification at the cleavage site or in the cleavage region;

a second strand which targets a sequence and which dose not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1,2, 3, 4, 5, or 6 away from the 5' terminus of an antisense strand).

Ribose Mimics

An RNA, e.g., an iRNA agent, can incorporate a ribose mimic. In addition, the invention includes iRNA agents having a ribose mimic and another element described herein. E.g., the invention includes an iRNA agent described herein, e.g., a palindromic iRNA agent, an iRNA agent having a non canonical pairing, an iRNA agent which targets a gene described herein, e.g., an SNCA gene, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates a ribose mimic.

Thus, an aspect of the invention features an iRNA agent that includes a secondary hydroxyl group, which can increase efficacy and/or confer nuclease resistance to the agent. Nucleases, e.g., cellular nucleases, can hydrolyze nucleic acid phosphodiester bonds, resulting in partial or complete degradation of the nucleic acid. The secondary hydroxy group confers nuclease resistance to an iRNA agent by rendering the iRNA agent less prone to nuclease degradation relative to an iRNA which lacks the modification. While not wishing to be bound by theory, it is believed that the presence of a secondary hydroxyl group on the iRNA agent can act as a structural mimic of a 3' ribose hydroxyl group, thereby causing it to be less susceptible to degradation.

The secondary hydroxyl group refers to an "OH" radical that is attached to a carbon atom substituted by two other carbons and a hydrogen. The secondary hydroxyl group that confers nuclease resistance as described above can be part of any acyclic carbon-containing group. The hydroxyl may also be part of any cyclic carbon-containing group, and preferably one or more of the following conditions is met (1) there is no ribose moiety between the hydroxyl group and the terminal phosphate group or (2) the hydroxyl group is not on a sugar moiety which is coupled to a base. The hydroxyl group is located at least two bonds (e.g., at least three bonds away, at least four bonds away, at least five bonds away, at least six bonds away, at least seven bonds away, at least eight bonds away, at least nine bonds away, at least ten bonds away, etc.) from the terminal phosphate group phosphorus of the iRNA agent. In preferred embodiments, there are five intervening bonds between the terminal phosphate group phosphorus and the secondary hydroxyl group.

Preferred iRNA agent delivery modules with five intervening bonds between the terminal phosphate group phosphorus and the secondary hydroxyl group have the following structure (see formula Y below):

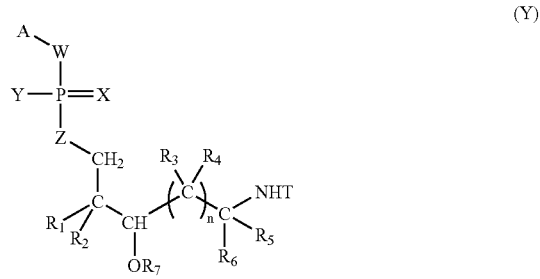

(Y)

Referring to formula Y, A is an iRNA agent, including any iRNA agent described herein. The iRNA agent may be connected directly or indirectly (e.g., through a spacer or linker) to "W" of the phosphate group. These spacers or linkers can include e.g., —$(CH_2)_n$—, —$(CH_2)_nN$—, —$(CH_2)_nO$—, —$(CH_2)_nS$—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents.

The iRNA agents can have a terminal phosphate group that is unmodified (e.g., W, X, Y, and Z are O) or modified. In a modified phosphate group, W and Z can be independently NH, O, or S; and X and Y can be independently S, Se, $BH_3^-$, $C_1$-$C_6$ alkyl, $C_6$-$C_{10}$ aryl, H, O, O$^-$, alkoxy or amino (including alkylamino, arylamino, etc.). Preferably, W, X and Z are O and Y is S.

$R_1$ and $R_3$ are each, independently, hydrogen; or $C_1$-$C_{100}$ alkyl, optionally substituted with hydroxyl, amino, halo, phosphate or sulfate and/or may be optionally inserted with N, O, S, alkenyl or alkynyl.

$R_2$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_2$ may be taken together with $R_4$ or $R_6$ to form a ring of 5-12 atoms.

$R_4$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_4$ may be taken together with $R_2$ or $R_5$ to form a ring of 5-12 atoms.

$R_5$ is hydrogen, $C_1$-$C_{100}$ alkyl optionally substituted with hydroxyl, amino, halo, phosphate or sulfate and/or may be optionally inserted with N, O, S, alkenyl or alkynyl; or, when n is 1, $R_5$ may be taken together with $R_4$ to form a ring of 5-12 atoms.

$R_6$ is hydrogen, $C_1$-$C_{100}$ alkyl, optionally substituted with hydroxyl, amino, halo, phosphate or sulfate and/or may be optionally inserted with N, O, S, alkenyl or alkynyl, or, when n is 1, $R_6$ may be taken together with $R_2$ to form a ring of 6-10 atoms;

$R_7$ is hydrogen, $C_1$-$C_{100}$ alkyl, or $C(O)(CH_2)_q C(O)NHR_9$; T is hydrogen or a functional group; n and q are each independently 1-100; $R_8$ is $C_1$-$C_{10}$ alkyl or $C_6$-$C_{10}$ aryl; and $R_9$ is hydrogen, C1-C10 alkyl, C6-C10 aryl or a solid support agent.

Preferred embodiments may include one of more of the following subsets of iRNA agent delivery modules.

In one subset of RNAi agent delivery modules, A can be connected directly or indirectly through a terminal 3' or 5' ribose sugar carbon of the RNA agent.

In another subset of RNAi agent delivery modules, X, W, and Z are O and Y is S.

In still yet another subset of RNAi agent delivery modules, n is 1, and $R_2$ and $R_6$ are taken together to form a ring containing six atoms and $R_4$ and $R_5$ are taken together to form a ring containing six atoms. Preferably, the ring system is a trans-decalin. For example, the RNAi agent delivery module of this subset can include a compound of Formula (Y-1):

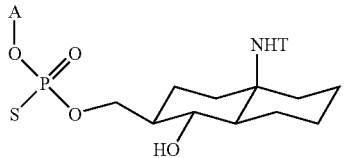

The functional group can be, for example, a targeting group (e.g., a steroid or a carbohydrate), a reporter group (e.g., a fluorophore), or a label (an isotopically labeled moiety). The targeting group can further include protein binding agents, endothelial cell targeting groups (e.g., RGD peptides and mimetics), cancer cell targeting groups (e.g., folate Vitamin B12, Biotin), bone cell targeting groups (e.g., bisphosphonates, polyglutamates, polyaspartates), multivalent mannose (for e.g., macrophage testing), lactose, galactose, N-acetyl-galactosamine, monoclonal antibodies, glycoproteins, lectins, melanotropin, or thyrotropin.

As can be appreciated by the skilled artisan, methods of synthesizing the compounds of the formulae herein will be evident to those of ordinary skill in the art. The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Ribose Replacement Monomer Subunits iRNA agents can be modified in a number of ways which can optimize one or more characteristics of the iRNA agent. An RNA agent, e.g., an iRNA agent can include a ribose replacement monomer subunit (RRMS), such as those described herein In addition, an iRNA agent can have an RRMS and another element described herein. E.g., the invention includes an iRNA agent described herein, e.g., a palindromic iRNA agent, an iRNA agent having a non canonical pairing, an iRNA agent which targets a gene described herein, e.g., an SNCA gene, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates a RRMS.

The ribose sugar of one or more ribonucleotide subunits of an iRNA agent can be replaced with another moiety, e.g., a non-carbohydrate (preferably cyclic) carrier. A ribonucleotide subunit in which the ribose sugar of the subunit has been so replaced is referred to herein as an RRMS. A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The carriers further include (i) at least two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" as used herein refers to a constituent ring atom of the cyclic carrier, e.g., a carbon atom or a heteroatom (distinct from an atom which provides a backbone attachment point), that connects a selected moiety. The moiety can be, e.g., a ligand, e.g., a targeting or delivery moiety, or a moiety which alters a physical property, e.g., lipophilicity, of an iRNA agent. Optionally, the selected moiety is connected by an intervening tether to the cyclic carrier.

Thus, it will include a functional group, e.g., an amino group, or generally, provide a bond, that is suitable for incorporation or tethering of another chemical entity, e.g., a ligand to the constituent ring.

Incorporation of one or more RRMSs described herein into an RNA agent, e.g., an iRNA agent, particularly when tethered to an appropriate entity, can confer one or more new properties to the RNA agent and/or alter, enhance or modulate one or more existing properties in the RNA molecule. E.g., it can alter one or more of lipophilicity or nuclease resistance. Incorporation of one or more RRMSs described herein into an iRNA agent can, particularly when the RRMS is tethered to an appropriate entity, modulate, e.g., increase, binding affinity of an iRNA agent to a target mRNA, change the geometry of the duplex form of the iRNA agent, alter distribution or target the iRNA agent to a particular part of the body, or modify the interaction with nucleic acid binding proteins (e.g., during RISC formation and strand separation).

Accordingly, in one aspect, the invention features, an iRNA agent preferably comprising a first strand and a second strand, wherein at least one subunit having a formula (R-1) is incorporated into at least one of said strands.

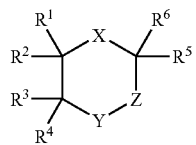

(R-1)

Referring to formula (R-1), X is $N(CO)R^7$, $NR^7$ or $CH_2$; Y is $NR^8$, O, S, $CR^9R^{10}$, or absent; and Z is $CR^{11}R^{12}$ or absent.

Each of $R^1$, $R^2$, $R^3$, $R^4$, $R^9$, and $R^{10}$ is, independently, H, $OR^a$, $OR^b$, $(CH_2)_nOR^a$, or $(CH_2)_nOR^b$, provided that at least one of $R^1$, $R^2$, $R^3$, $R^4$, $R^9$, and $R^{10}$ is $OR^a$ or $OR^b$ and that at least one of $R^1$, $R^2$, $R^3$, $R^4$, $R^9$, and $R^{10}$ is $(CH_2)_nOR^a$, or $(CH_2)_nOR^b$ (when the RRMS is terminal, one of $R^1$, $R^2$, $R^3$, $R^4$, $R^9$, and $R^{10}$ will include $R^a$ and one will include $R^b$; when the RRMS is internal, two of $R^1$, $R^2$, $R^3$, $R^4$, $R^9$, and $R^{10}$ will each include an R); further provided that preferably $OR^a$ may only be present with $(CH_2)_nOR^b$ and $(CH_2)_nOR^a$ may only be present with $OR^b$.

Each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$.

$R^7$ is $C_1$-$C_{20}$ alkyl substituted with $NR^cR^d$; $R^8$ is $C_1$-$C_6$ alkyl; $R^{13}$ is hydroxy, $C_1$-$C_4$ alkoxy, or halo; and $R^{14}$ is $NR^cR^7$.

$R^a$ is:

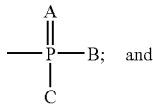 and $R^b$ is:

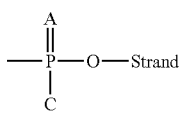

Each of A and C is, independently, O or S.

B is OH, $O^-$, or

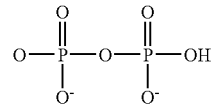

$R^c$ is H or C1-C6 alkyl; $R^d$ is H or a ligand; and n is 1-4.

In a preferred embodiment the ribose is replaced with a pyrroline scaffold, and X is $N(CO)R^7$ or $NR^7$, Y is $CR^9R^{10}$, and Z is absent.

In other preferred embodiments the ribose is replaced with a piperidine scaffold, and X is $N(CO)R^7$ or $NR^7$, Y is $CR^9R^{10}$, and Z is $CR^{11}R^{12}$.

In other preferred embodiments the ribose is replaced with a piperazine scaffold, and X is $N(CO)R^7$ or $NR^7$, Y is $NR^8$, and Z is $CR^{11}R^{12}$.

In other preferred embodiments the ribose is replaced with a morpholino scaffold, and X is $N(CO)R^7$ or $NR^7$, Y is O, and Z is $CR^{11}R^{12}$.

In other preferred embodiments the ribose is replaced with a decalin scaffold, and X is $CH_2$; Y is $CR^9R^{10}$; and Z is $CR^{11}R^{12}$; and $R^5$ and $R^{11}$ together are $C^6$ cycloalkyl.

In other preferred embodiments the ribose is replaced with a decalin/indane scaffold and, and X is $CH_2$; Y is $CR^9R^{10}$; and Z is $CR^{11}R^{12}$; and $R^5$ and $R^{11}$ together are $C^5$ cycloalkyl.

In other preferred embodiments, the ribose is replaced with a hydroxyproline scaffold.

RRMSs described herein may be incorporated into any double-stranded RNA-like molecule described herein, e.g., an iRNA agent. An iRNA agent may include a duplex comprising a hybridized sense and antisense strand, in which the antisense strand and/or the sense strand may include one or more of the RRMSs described herein. An RRMS can be introduced at one or more points in one or both strands of a double-stranded iRNA agent. An RRMS can be placed at or near (within 1, 2, or 3 positions) of the 3' or 5' end of the sense strand or at near (within 2 or 3 positions of) the 3' end of the antisense strand. In some embodiments it is preferred to not have an RRMS at or near (within 1, 2, or 3 positions of) the 5' end of the antisense strand. An RRMS can be internal, and will preferably be positioned in regions not critical for antisense binding to the target.

In an embodiment, an iRNA agent may have an RRMS at (or within 1, 2, or 3 positions of) the 3' end of the antisense strand. In an embodiment, an iRNA agent may have an RRMS at (or within 1, 2, or 3 positions of) the 3' end of the antisense strand and at (or within 1, 2, or 3 positions of) the 3' end of the sense strand. In an embodiment, an iRNA agent may have an RRMS at (or within 1, 2, or 3 positions of) the 3' end of the antisense strand and an RRMS at the 5' end of the sense strand, in which both ligands are located at the same end of the iRNA agent.

In certain embodiments, two ligands are tethered, preferably, one on each strand and are hydrophobic moieties. While not wishing to be bound by theory, it is believed that pairing of the hydrophobic ligands can stabilize the iRNA agent via intermolecular van der Waals interactions.

In an embodiment, an iRNA agent may have an RRMS at (or within 1, 2, or 3 positions of) the 3' end of the antisense strand and an RRMS at the 5' end of the sense strand, in which both RRMSs may share the same ligand (e.g., cholic acid) via connection of their individual tethers to separate positions on the ligand. A ligand shared between two proximal RRMSs is referred to herein as a "hairpin ligand."

In other embodiments, an iRNA agent may have an RRMS at the 3' end of the sense strand and an RRMS at an internal position of the sense strand. An iRNA agent may have an RRMS at an internal position of the sense strand; or may have an RRMS at an internal position of the antisense strand; or may have an RRMS at an internal position of the sense strand and an RRMS at an internal position of the antisense strand.

In preferred embodiments the iRNA agent includes a first and second sequence, which are preferably two separate molecules as opposed to two sequences located on the same strand, have sufficient complementarity to each other to hybridize (and thereby form a duplex region), e.g., under physiological conditions, e.g., under physiological conditions but not in contact with a helicase or other unwinding enzyme.

It is preferred that the first and second sequences be chosen such that the ds iRNA agent includes a single strand or unpaired region at one or both ends of the molecule. Thus, a ds iRNA agent contains first and second sequences, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Tethered Entities

A wide variety of entities can be tethered to an iRNA agent, e.g., to the carrier of an RRMS. Examples are described below in the context of an RRMS but that is only preferred, entities can be coupled at other points to an iRNA agent. Preferred entities are those which target to a neural cell, e.g., a neural cell expressing SNCA.

Preferred moieties are ligands, which are coupled, preferably covalently, either directly or indirectly via an intervening tether, to the RRMS carrier. In preferred embodiments, the ligand is attached to the carrier via an intervening tether. As discussed above, the ligand or tethered ligand may be present on the RRMS monomer when the RRMS monomer is incorporated into the growing strand. In some embodiments, the ligand may be incorporated into a "precursor" RRMS after a "precursor" RRMS monomer has been incorporated into the growing strand. For example, an RRMS monomer having, e.g., an amino-terminated tether (i.e., having no associated ligand), e.g., TAP-$(CH_2)_n NH_2$ may be incorporated into a growing sense or antisense strand. In a subsequent operation, i.e., after incorporation of the precursor monomer into the strand, a ligand having an electrophilic group, e.g., a pentafluorophenyl ester or aldehyde group, can subsequently be attached to the precursor RRMS by coupling the electrophilic group of the ligand with the terminal nucleophilic group of the precursor RRMS tether.

In preferred embodiments, a ligand alters the distribution, targeting or lifetime of an iRNA agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand. For example, in a preferred embodiment, a ligand will provide enhanced selectivity to a neural cell, such as in the brain. Preferred ligands will not take part in duplex pairing in a duplexed nucleic acid.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), or globulin); carbohydrate (e.g., a dextran, pullulan, chitin, chitosan, insulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a neural cell.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP. In one embodiment, a ligand can facilitate the movement of the iRNA agent across the blood-brain barrier.

Ligands can be proteins, e.g., glycoproteins, or peptides, e.g., molecules having a specific affinity for a co-ligand, or antibodies e.g., an antibody, that binds to a specified cell type such as a neural cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-liver target tissue of the body. Preferably, the target tissue is the brain. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the liver and therefore less likely to be cleared from the body.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 300, 35, 40, 45, or 50 amino acids long (see Table 3, for example).

TABLE 3

Exemplary Cell Permeation Peptides

| Cell Permeation Peptide | Amino acid Sequence | Reference |
|---|---|---|
| Penetratin | RQIKIWFQNRRMKWKK (SEQ ID NO:31) | Derossi et al., J. Biol. Chem. 269:10444, 1994 |
| Tat fragment (48-60) | GRKKRRQRRRPPQC (SEQ ID NO:32) | Vives et al., J. Biol. Chem., 272:16010, 1997 |
| Signal Sequence-based peptide | GALFLGWLGAAGSTMGAWS QPKKKRKV (SEQ ID NO:33) | Chaloin et al., Biochem. Biophys. Res. Commun., 243:601, 1998 |
| PVEC | LLIILRRRIRKQAHAHSK (SEQ ID NO:34) | Elmquist et al., Exp. Cell Res., 269:237, 2001 |
| Transportan | GWTLNSAGYLLKINLKALA ALAKKIL | Pooga et al., FASEB |

| | | |
|---|---|---|
| Amphiphilic model peptide | KLALKLALKALKAALKLA (SEQ ID NO:36) | J., 12:67, 1998 Oehlke et al., Mol. Ther., 2:339, 2000 |
| Arg9 | RRRRRRRRR (SEQ ID NO:37) | Mitchell et al., J. Pept. Res., 56:3 18, 2000 |
| Bacterial cell wall permeating | KFFKFFKFFK (SEQ ID NO:38) | |
| LL-37 | LLGDFFRKSKEKIGKEFKRIVQRIKDFLRN LVPRTES (SEQ ID NO:39) | |
| Cecropin P1 | SWLSKTAKKLENSAKKRISEGIAIAIQGGPR (SEQ ID NO:40) | |
| α-defensin | ACYCRIPACIAGERRYGTCIYQGRLWAFCC (SEQ ID NO:41) | |
| b-defensin | DHYNCVSSGGQCLYSACPIFTKIQGTCYR GKAKCCK (SEQ ID NO:42) | |
| Bactenecin | RKCRIVVIRVCR (SEQ ID NO:43) | |
| PR-39 | RRRPRPPYLPRPRPPPFFPPRLPPRIPPGFPP RFPPRFPGKR-NH2 (SEQ ID NO:44) | |
| Indolicidin | ILPWKWPWWPWRR-NH2 (SEQ ID NO:45) | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:46). An RFGF analogue (e.g., amino acid sequence AALLPVLLAAP (SEQ ID NO:47) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQR-RRPPQ (SEQ ID NO:48) and the Drosophila Antennapedia protein (RQIKIWFQNRRMKWKK (SEQ ID NO:49) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

A "cell permeation peptide" is capable of permeating a cell, e.g., a—mammalian cell, such as a human cell. A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide tethered to an RRMS can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

Methods for Making iRNA Agents iRNA agents can include modified or non-naturally occurring bases, e.g., bases described herein. In addition, iRNA agents can have a modified or non-naturally occurring base and another element described herein. E.g., the invention includes an iRNA agent described herein, e.g., a palindromic iRNA agent, an iRNA agent having a non canonical pairing, an iRNA agent which targets a gene described herein, e.g., an SNCA gene, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates a modified or non-naturally occurring base.

The synthesis and purification of oligonucleotide peptide conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001.

In one embodiment of the invention, a peptidomimetic can be modified to create a constrained peptide that adopts a distinct and specific preferred conformation, which can increase the potency and selectivity of the peptide. For example, the constrained peptide can be an azapeptide (Gante, *Synthesis* 405-413, 1989). An azapeptide is synthesized by replacing the α-carbon of an amino acid with a nitrogen atom without changing the structure of the amino acid side chain. For example, the azapeptide can be synthesized by using hydrazine in traditional peptide synthesis coupling methods, such as by reacting hydrazine with a "carbonyl donor," e.g., phenylchloroformate.

In one embodiment of the invention, a peptide or peptidomimetic (e.g., a peptide or peptidomimetic tethered to an RRMS) can be an N-methyl peptide. N-methyl peptides are composed of N-methyl amino acids, which provide an additional methyl group in the peptide backbone, thereby potentially providing additional means of resistance to proteolytic cleavage. N-methyl peptides can by synthesized by methods known in the art (see, for example, Lindgren et al., Trends Pharmacol. Sci. 21:99, 2000; *Cell Penetrating Peptides: Processes and Applications*, Langel, ed., CRC Press, Boca Raton, Fla., 2002; Fische et al., Bioconjugate. Chem. 12: 825, 2001; Wander et al., J. Am. Chem. Soc., 124:13382, 2002). For example, an Ant or Tat peptide can be an N-methyl peptide.

In one embodiment of the invention, a peptide or peptidomimetic (e.g., a peptide or peptidomimetic tethered to an RRMS) can be a β-peptide. β-peptides form stable secondary structures such as helices, pleated sheets, turns and hairpins in solutions. Their cyclic derivatives can fold into nanotubes in the solid state. β-peptides are resistant to degradation by proteolytic enzymes. β-peptides can be synthesized by methods known in the art. For example, an Ant or Tat peptide can be a β-peptide.

In one embodiment of the invention, a peptide or peptidomimetic (e.g., a peptide or peptidomimetic tethered to an RRMS) can be a oligocarbamate. Oligocarbamate peptides are internalized into a cell by a transport pathway facilitated by carbamate transporters. For example, an Ant or Tat peptide can be an oligocarbamate.

In one embodiment of the invention, a peptide or peptidomimetic (e.g., a peptide or peptidomimetic tethered to an RRMS) can be an oligourea conjugate (or an oligothiourea conjugate), in which the amide bond of a peptidomimetic is replaced with a urea moiety. Replacement of the amide bond provides increased resistance to degradation by proteolytic enzymes, e.g., proteolytic enzymes in the gastrointestinal tract. In one embodiment, an oligourea conjugate is tethered to an iRNA agent for use in oral delivery. The backbone in each repeating unit of an oligourea peptidomimetic can be extended by one carbon atom in comparison with the natural amino acid. The single carbon atom extension can increase peptide stability and lipophilicity, for example. An oligourea peptide can therefore be advantageous when an iRNA agent is directed for passage through a bacterial cell wall, or when an iRNA agent must traverse the blood-brain barrier, such as for the treatment of a neurological disorder. In one embodiment, a hydrogen bonding unit is conjugated to the oligourea peptide, such as to create an increased affinity with a receptor. For example, an Ant or Tat peptide can be an oligourea conjugate (or an oligothiourea conjugate).

The dsRNA peptide conjugates of the invention can be affiliated with, e.g., tethered to, RRMSs occurring at various positions on an iRNA agent. For example, a peptide can be terminally conjugated, on either the sense or the antisense strand, or a peptide can be bisconjugated (one peptide tethered to each end, one conjugated to the sense strand, and one conjugated to the antisense strand). In another option, the peptide can be internally conjugated, such as in the loop of a short hairpin iRNA agent. In yet another option, the peptide can be affiliated with a complex, such as a peptide-carrier complex.

A peptide-carrier complex consists of at least a carrier molecule, which can encapsulate one or more iRNA agents (such as for delivery to a biological system and/or a cell), and a peptide moiety tethered to the outside of the carrier molecule, such as for targeting the carrier complex to a particular tissue or cell type. A carrier complex can carry additional targeting molecules on the exterior of the complex, or fusogenic agents to aid in cell delivery. The one or more iRNA agents encapsulated within the carrier can be conjugated to lipophilic molecules, which can aid in the delivery of the agents to the interior of the carrier.

A carrier molecule or structure can be, for example, a micelle, a liposome (e.g., a cationic liposome), a nanoparticle, a microsphere, or a biodegradable polymer. A peptide moiety can be tethered to the carrier molecule by a variety of linkages, such as a disulfide linkage, an acid labile linkage, a peptide-based linkage, an oxyamino linkage or a hydrazine linkage. For example, a peptide-based linkage can be a GFLG peptide. Certain linkages will have particular advantages, and the advantages (or disadvantages) can be considered depending on the tissue target or intended use. For example, peptide based linkages are stable in the blood stream but are susceptible to enzymatic cleavage in the lysosomes.

Definitions

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^2$ carbons may optionally serve as the point of attachment of the alkenyl and alkynyl groups, respectively.

The term "alkoxy" refers to an —O-alkyl radical. The term "aminoalkyl" refers to an alkyl substituted with an amino. The term "mercapto" refers to an —SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxy" refers to a divalent species of the structure —O—R—O—, in which R represents an alkylene.

The term "aryl" refers to an aromatic monocyclic, bicyclic, or tricyclic hydrocarbon ring system, wherein any ring atom capable of substitution can be substituted by a substituent. Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons, wherein any ring atom capable of substitution can be substituted by a substituent. The cycloalkyl groups herein described may also contain fused rings. Fused rings are rings that share a common carbon-carbon bond. Examples of cycloalkyl moieties include, but are not limited to, cyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent. The heterocyclyl groups herein described may also contain fused rings. Fused rings are rings that share a common carbon-carbon bond. Examples of heterocyclyl include, but are not limited to tetrahydrofuranyl, tetrahydropyranyl, piperidinyl, morpholino, pyrrolinyl and pyrrolidinyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, SO$_3$H, sulfate, phosphate, perfluoroalkyl, perfluoroalkoxy, methylenedioxy, ethylenedioxy, carboxyl, oxo, thioxo, imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroalkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

As used herein, an "unusual" nucleobase can include any one of the following:

2-methyladeninyl,

N6-methyladeninyl, 2-methylthio-N-6-methyladeninyl,

N6-isopentenyladeninyl, 2-methylthio-N-6-isopentenyladeninyl,

N6-(cis-hydroxyisopentenyl)adeninyl, 2-methylthio-N-6-(cis-hydroxyisopentenyl)adeninyl, N6-glycinylcarbamoyladeninyl, N6-threonylcarbamoyladeninyl, 2-methylthio-N-6-threonyl carbamoyladeninyl, N6-methyl-N-6-threonylcarbamoyladeninyl, N6-hydroxynorvalylcarbamoyladeninyl, 2-methylthio-N-6-hydroxynorvalyl carbamoyladeninyl, N6,N6-dimethyladeninyl, 3-methylcytosinyl, 5-methylcytosinyl, 2-thiocytosinyl, 5-formylcytosinyl,

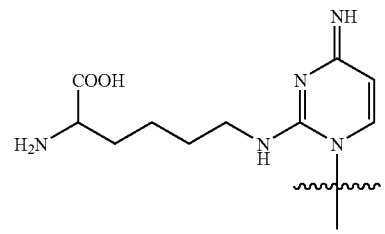

N4-methylcytosinyl, 5-hydroxymethylcytosinyl, 1-methylguaninyl,

N2-methylguaninyl, 7-methylguaninyl,

N2,N2-dimethylguaninyl,

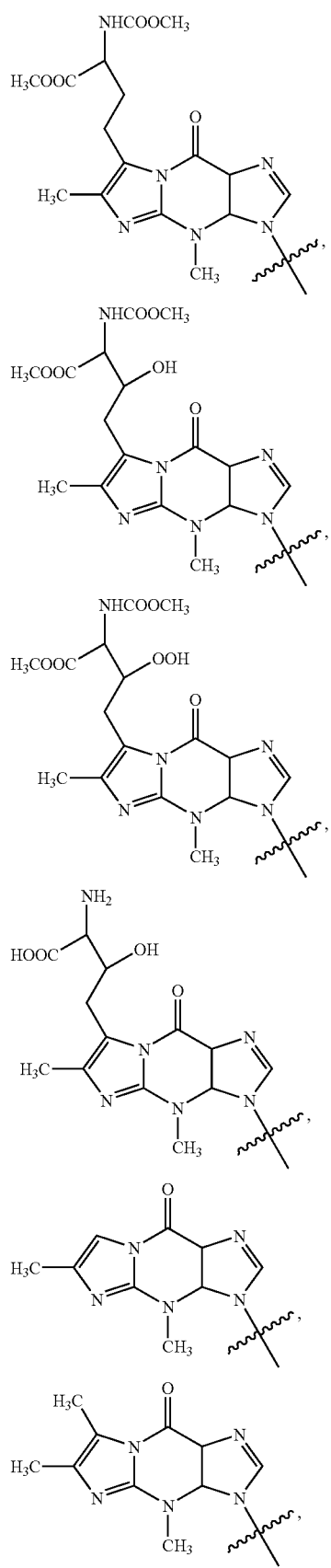
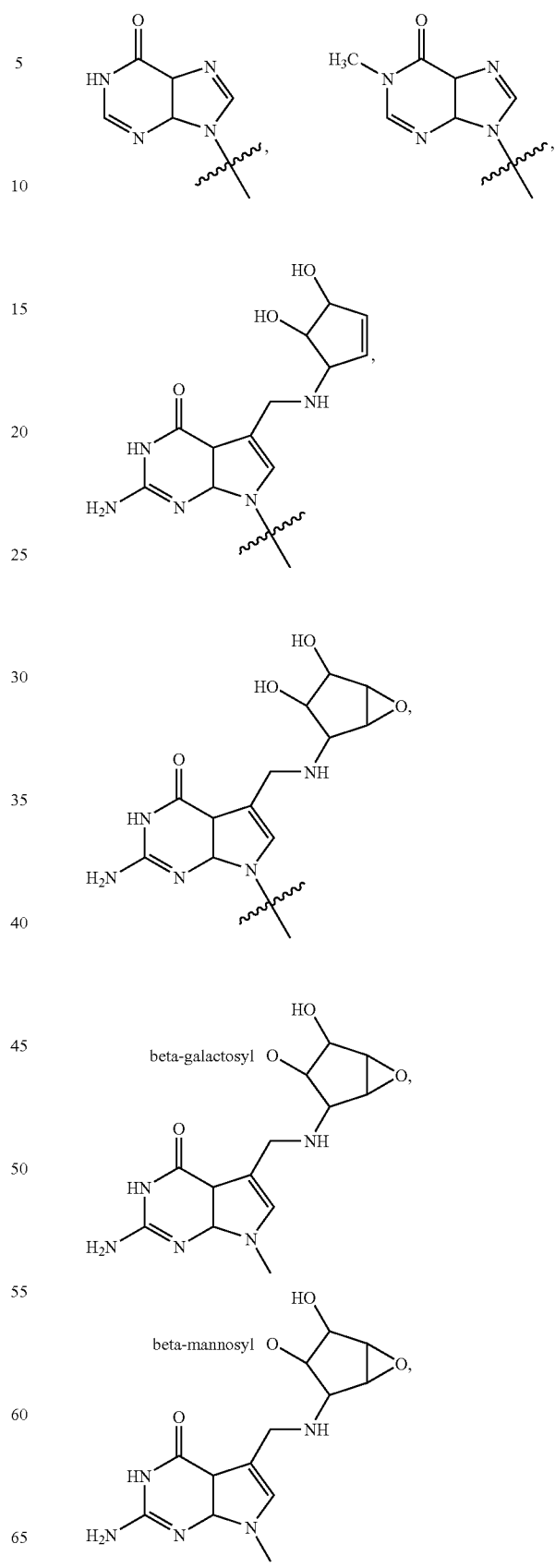
-continued

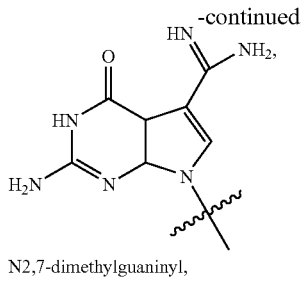

N2,7-dimethylguaninyl,

N2,N2,7-trimethylguaninyl,
1-methylguaninyl,
7-cyano-7-deazaguaninyl,
7-aminomethyl-7-deazaguaninyl,
pseudouracilyl,
dihydrouracilyl,
5-methyluracilyl,
1-methylpseudouracilyl,
2-thiouracilyl,
4-thiouracilyl,
2-thiothyminyl
5-methyl-2-thiouracilyl,
3-(3-amino-3-carboxypropyl)uracilyl,
5-hydroxyuracilyl,
5-methoxyuracilyl,
uracilyl 5-oxyacetic acid,
uracilyl 5-oxyacetic acid methyl ester,
5-(carboxyhydroxymethyl)uracilyl,
5-(carboxyhydroxymethyl)uracilyl methyl ester,
5-methoxycarbonylmethyluracilyl,
5-methoxycarbonylmethyl-2-thiouracilyl,
5-aminomethyl-2-thiouracilyl,
5-methylaminomethyluracilyl,
5-methylaminomethyl-2-thiouracilyl,
5-methylaminomethyl-2-selenouracilyl,
5-carbamoylmethyluracilyl,
5-carboxymethylaminomethyluracilyl,
5-carboxymethylaminomethyl-2-thiouracilyl,
3-methyluracilyl,
1-methyl-3-(3-amino-3-carboxypropyl)pseudouracilyl,
5-carboxymethyluracilyl,
5-methyldihydrouracilyl, or
3-methylpseudouracilyl.

Palindromes

An RNA, e.g., an iRNA agent, can have a palindrome structure as described herein. For example, the iRNA agents of the invention can target more than one RNA region. For example, an iRNA agent can include a first and second sequence that are sufficiently complementary to each other to hybridize. The first sequence can be complementary to a first target sequence of an SNCA RNA and the second sequence can be complementary to a second target sequence of an SNCA RNA. The first and second target sequences can differ by at least 1 nucleotide. The first and second sequences of the iRNA agent can be on different RNA strands, and the mismatch between the first and second sequences can be less than 50%, 40%, 30%, 20%, 10%, 5%, or 1%. The first and second sequences of the iRNA agent can be on the same RNA strand, and in a related embodiment more than 50%, 60%, 70%, 80%, 90%, 95%, or 1% of the iRNA agent can be in bimolecular form. The first and second sequences of the iRNA agent can be fully complementary to each other.

The first and second target RNA regions can be on transcripts encoded by first and second sequence variants, e.g., first and second alleles, of an SNCA gene. The sequence variants can be mutations, or polymorphisms, for example. The first target RNA region can include a nucleotide substitution, insertion, or deletion relative to the second target RNA region, or the second target RNA region can a mutant or variant of the first target region.

The compositions of the invention can include mixtures of iRNA agent molecules. For example, one iRNA agent can contain a first sequence and a second sequence sufficiently complementary to each other to hybridize, and in addition the first sequence is complementary to a first target RNA region and the second sequence is complementary to a second target RNA region. The mixture can also include at least one additional iRNA agent variety that includes a third sequence and a fourth sequence sufficiently complementary to each other to hybridize, and where the third sequence is complementary to a third target RNA region and the fourth sequence is complementary to a fourth target RNA region. In addition, the first or second sequence can be sufficiently complementary to the third or fourth sequence to be capable of hybridizing to each other. The first and second sequences can be on the same or different RNA strands, and the third and fourth sequences can be on the same or different RNA strands.

An iRNA agent can include a first sequence complementary to a first variant SNCA RNA target region and a second sequence complementary to a second variant SNCA RNA target region. The first and second variant target RNA regions can include allelic variants, mutations (e.g., point mutations), or polymorphisms of the SNCA target gene. Other than Canonical Watson-Crick Duplex Structures.

Other than Canonical Watson-Crick Duplex Structures

An RNA, e.g., an iRNA agent can include monomers that can form other than a canonical Watson-Crick pairing with another monomer, e.g., a monomer on another strand. The use of "other than canonical Watson-Crick pairing" between monomers of a duplex can be used to control, often to promote, melting of all or part of a duplex. The iRNA agent can include a monomer at a selected or constrained position that results in a first level of stability in the iRNA agent duplex (e.g., between the two separate molecules of a double stranded iRNA agent) and a second level of stability in a duplex between a sequence of an iRNA agent and another sequence molecule, e.g., a target or off-target sequence in a subject. In some cases the second duplex has a relatively greater level of stability, e.g., in a duplex between an antisense sequence of an iRNA agent and a target mRNA. In this case one or more of the monomers, the position of the monomers in the iRNA agent, and the target sequence (sometimes referred to herein as the selection or constraint parameters), are selected such that the iRNA agent duplex has a comparatively lower free energy of association (which while not wishing to be bound by mechanism or theory, is believed to contribute to efficacy by promoting disassociation of the duplex iRNA agent in the context of the RISC) while the duplex formed between an antisense targeting sequence and its target sequence, has a relatively higher free energy of association (which while not wishing to be bound by mechanism or theory, is believed to contribute to efficacy by promoting association of the antisense sequence and the target RNA).

In other cases the second duplex has a relatively lower level of stability, e.g., in a duplex between a sense sequence of an iRNA agent and an off-target mRNA. In this case one or more of the monomers, the position of the monomers in the iRNA agent, and an off-target sequence, are selected such that the iRNA agent duplex is has a comparatively higher free energy of association while the duplex formed between a sense targeting sequence and its off-target sequence, has a relatively lower free energy of association (which while not wishing to be bound by mechanism or theory, is believed to reduce the level of off-target silencing by promoting disassociation of the duplex formed by the sense strand and the off-target sequence).

Thus, inherent in the structure of the iRNA agent is the property of having a first stability for the intra-iRNA agent duplex and a second stability for a duplex formed between a sequence from the iRNA agent and another RNA, e.g., a target mRNA. As discussed above, this can be accomplished by judicious selection of one or more of the monomers at a selected or constrained position, the selection of the position in the duplex to place the selected or constrained position, and selection of the sequence of a target sequence (e.g., the particular region of a target gene which is to be targeted). The iRNA agent sequences which satisfy these requirements are sometimes referred to herein as constrained sequences. Exercise of the constraint or selection parameters can be, e.g., by inspection or by computer assisted methods. Exercise of the parameters can result in selection of a target sequence and of particular monomers to give a desired result in terms of the stability, or relative stability, of a duplex.

Thus, in another aspect, the invention features an iRNA agent which includes: a first sequence which targets a first target region and a second sequence which targets a second target region. The first and second sequences have sufficient complementarity to each other to hybridize, e.g., under physiological conditions, e.g., under physiological conditions but not in contact with a helicase or other unwinding enzyme. In a duplex region of the iRNA agent, at a selected or constrained position, the first target region has a first monomer, and the second target region has a second monomer. The first and second monomers occupy complementary or corresponding positions. One, and preferably both monomers are selected such that the stability of the pairing of the monomers contribute to a duplex between the first and second sequence will differ form the stability of the pairing between the first or second sequence with a target sequence.

Usually, the monomers will be selected (selection of the target sequence may be required as well) such that they form a pairing in the iRNA agent duplex which has a lower free energy of dissociation, and a lower Tm, than will be possessed by the paring of the monomer with its complementary monomer in a duplex between the iRNA agent sequence and a target RNA duplex.

The constraint placed upon the monomers can be applied at a selected site or at more than one selected site. By way of example, the constraint can be applied at more than 1, but less than 3, 4, 5, 6, or 7 sites in an iRNA agent duplex.

A constrained or selected site can be present at a number of positions in the iRNA agent duplex. E.g., a constrained or selected site can be present within 3, 4, 5, or 6 positions from either end, 3' or 5' of a duplexed sequence. A constrained or selected site can be present in the middle of the duplex region, e.g., it can be more than 3, 4, 5, or 6, positions from the end of a duplexed region.

In some embodiment the duplex region of the iRNA agent will have mismatches, in addition to the selected or constrained site or sites. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

The monomers can be selected such that: first and second monomers are naturally occurring ribonucleotides, or modified ribonucleotides having naturally occurring bases, and when occupying complemetary sites either do not pair and have no substantial level of H-bonding, or form a non canonical Watson-Crick pairing and form a non-canonical pattern of H bonding, which usually have a lower free energy of dissociation than seen in a canonical Watson-Crick pairing, or otherwise pair to give a free energy of association which is less than that of a preselected value or is less, e.g., than that of a canonical pairing. When one (or both) of the iRNA agent sequences duplexes with a target, the first (or second) monomer forms a canonical Watson-Crick pairing with the base in the complemetary position on the target, or forms a non-canonical Watson-Crick pairing having a higher free energy of dissociation and a higher Tm than seen in the pairing in the iRNA agent. The classical Watson-Crick parings are as follows: A-T, G-C, and A-U. Non-canonical Watson-Crick pairings are known in the art and can include, U-U, G-G, G-$A_{trans}$, G-$A_{cis}$, and GU.

The monomer in one or both of the sequences is selected such that, it does not pair, or forms a pair with its corresponding monomer in the other sequence which minimizes stability (e.g., the H bonding formed between the monomer at the selected site in the one sequence and its monomer at the corresponding site in the other sequence are less stable than the H bonds formed by the monomer one (or both) of the sequences with the respective target sequence. The monomer of one or both strands is also chosen to promote stability in one or both of the duplexes made by a strand and its target sequence. E.g., one or more of the monomers and the target sequences are selected such that at the selected or constrained position, there is are no H bonds formed, or a non canonical pairing is formed in the iRNA agent duplex, or they otherwise pair to give a free energy of association which is less than that of a preselected value or is less, e.g., than that of a canonical pairing, but when one (or both) sequences form a duplex with the respective target, the pairing at the selected or constrained site is a canonical Watson-Crick paring.

The inclusion of such a monomer will have one or more of the following effects: it will destabilize the iRNA agent duplex, it will destabilize interactions between the sense sequence and unintended target sequences, sometimes referred to as off-target sequences, and duplex interactions between the a sequence and the intended target will not be destabilized.

A non-naturally occurring or modified monomer or monomers can be chosen such that when a non-naturally occurring or modified monomer occupies a position at the selected or constrained position in an iRNA agent they exhibit a first free energy of dissociation and when one (or both) of them pairs with a naturally occurring monomer, the pair exhibits a second free energy of dissociation, which is usually higher than that of the pairing of the first and second monomers. E.g., when the first and second monomers occupy complementary positions they either do not pair and have no substantial level of H-bonding, or form a weaker bond than one of them would form with a naturally occurring monomer, and reduce the stability of that duplex, but when the duplex dissociates at least one of the strands will form a duplex with a target in which the selected monomer will promote stability, e.g., the monomer will form a more stable pair with a naturally occurring monomer in the target sequence than the pairing it formed in the iRNA agent.

An example of such a pairing is 2-amino A and either of a 2-thio pyrimidine analog of U or T.

When placed in complementary positions of the iRNA agent these monomers will pair very poorly and will minimize stability. However, a duplex is formed between 2 amino A and the U of a naturally occurring target, or a duplex is between 2-thio U and the A of a naturally occurring target or 2-thio T and the A of a naturally occurring target will have a relatively higher free energy of dissociation and be more stable.

The term "other than canonical Watson-Crick pairing" as used herein, refers to a pairing between a first monomer in a first sequence and a second monomer at the corresponding position in a second sequence of a duplex in which one or more of the following is true: (1) there is essentially no pairing between the two, e.g., there is no significant level of H bonding between the monomers or binding between the monomers does not contribute in any significant way to the stability of the duplex; (2) the monomers are a non-canonical paring of monomers having a naturally occurring bases, i.e., they are other than A-T, A-U, or G-C, and they form monomer-monomer H bonds, although generally the H bonding pattern formed is less strong than the bonds formed by a canonical pairing; or (3) at least one of the monomers includes a non-naturally occurring bases and the H bonds formed between the monomers is, preferably formed is less strong than the bonds formed by a canonical pairing, namely one or more of A-T, A-U, G-C.

The term "off-target" as used herein, refers to as a sequence other than the sequence to be silenced.

Universal Bases: "wild-cards"; shape-based complementarity

Bi-stranded, multisite replication of a base pair between difluorotoluene and adenine: confirmation by 'inverse' sequencing. Liu, D.; Moran, S.; Kool, E. T. *Chem. Biol.,* 1997, 4, 919-926)

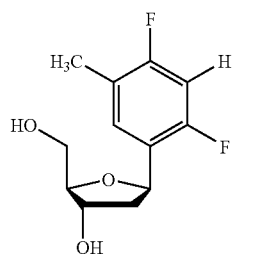

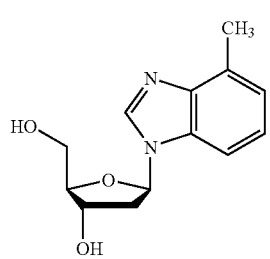

(Importance of terminal base pair hydrogen-bonding in 3'-end proofreading by the Klenow fragment of DNA polymerase I. Morales, J. C.; Kool, E. T. *Biochemistry,* 2000, 39, 2626-2632)

(Selective and stable DNA base pairing without hydrogen bonds. Matray, T, J.; Kool, E. T. *J. Am. Chem. Soc.,* 1998, 120, 6191-6192)

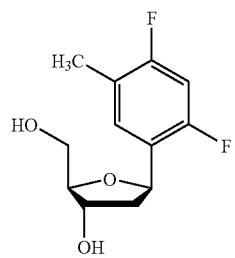

(Difluorotoluene, a nonpolar isostere for thymine, codes specifically and efficiently for adenine in DNA replication. Moran, S. Ren, R. X.-F.; Rumney IV, S.; Kool, E. T. *J. Am. Chem. Soc.,* 1997, 119, 2056-2057)

(Structure and base pairing properties of a replicable nonpolar isostere for deoxyadenosine. Guckian, K. M.; Morales, J. C.; Kool, E. T. *J. Org. Chem.,* 1998, 63, 9652-9656)

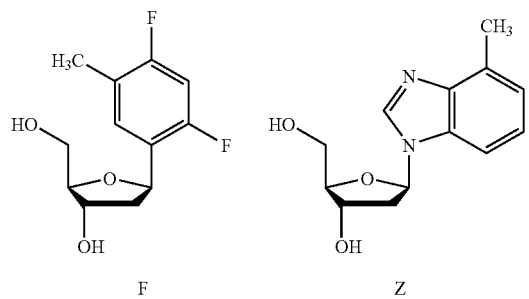

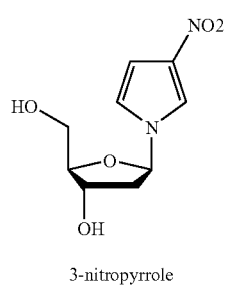

3-nitropyrrole

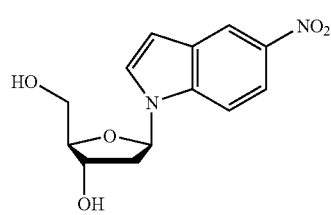

5-nitroindole

-continued

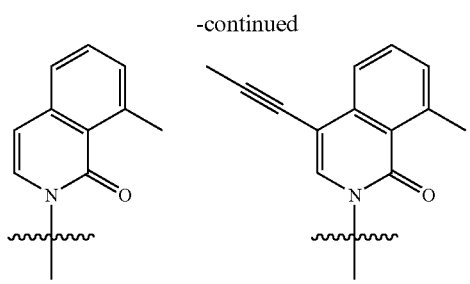

MICS  PIM

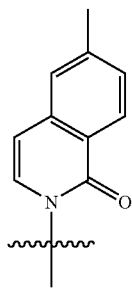

5MICS (Universal bases for hybridization, replication and chain termination. Berger, M.; Wu. Y.; Ogawa, A. K.; McMinn, D. L.; Schultz, P. G.; Romesberg, F. E. *Nucleic Acids Res.*, 2000, 28, 2911-2914)

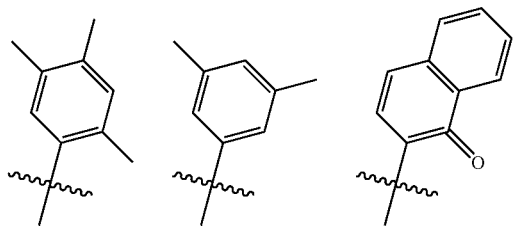

TM  DM  ICS

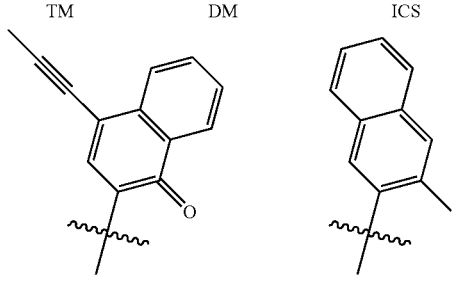

PICS  2MN

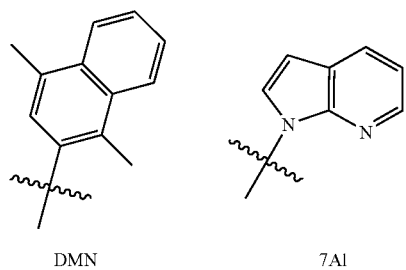

DMN  7AI

-continued

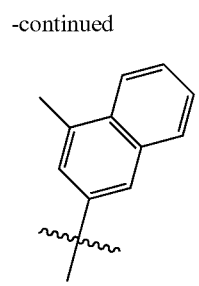

2Np  3MN (1. Efforts toward the expansion of the genetic alphabet: Information storage and replication with unnatural hydrophobic base pairs. Ogawa, A. K.; Wu, Y.; McMinn, D. L.; Liu, J.; Schultz, P. G.; Romesberg, F. E. *J. Am. Chem. Soc.*, 2000, 122, 3274-3287. 2. Rational design of an unnatural base pair with increased kinetic selectivity. Ogawa, A. K.; Wu. Y.; Berger, M.; Schultz, P. G.; Romesberg, F. E. *J. Am. Chem. Soc.*, 2000, 122, 8803-8804)

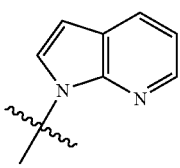

7AI (Efforts toward expansion of the genetic alphabet: replication of DNA with three base pairs. Tae, E. L.; Wu, Y.; Xia, G.; Schultz, P. G.; Romesberg, F. E. *J. Am. Chem. Soc.*, 2001, 123, 7439-7440)

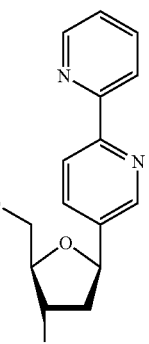

(1. Efforts toward expansion of the genetic alphabet: Optimization of interbase hydrophobic interactions. Wu, Y.; Ogawa, A. K.; Berger, M.; McMinn, D. L.; Schultz, P. G.; Romesberg, F. E. *J. Am. Chem. Soc.*, 2000, 122, 7621-7632. 2. Efforts toward expansion of genetic alphabet: DNA polymerase recognition of a highly stable, self-pairing hydrophobic base. McMinn, D. L.; Ogawa A. K.; Wu, Y.; Liu, J.; Schultz, P. G.; Romesberg, F. E. *J. Am. Chem. Soc.*, 1999, 121, 11585-11586)

(A stable DNA duplex containing a non-hydrogen-bonding and non-shape complementary base couple: Interstrand stacking as the stability determining factor. Brotschi, C.; Haberli, A.; Leumann, C, *J. Angew. Chem. Int. Ed.,* 2001, 40, 3012-3014)

(2,2'-Bipyridine Ligandoside: A novel building block for modifying DNA with intra-duplex metal complexes. Weizman, H.; Tor, Y. *J. Am. Chem. Soc.,* 2001, 123, 3375-3376)

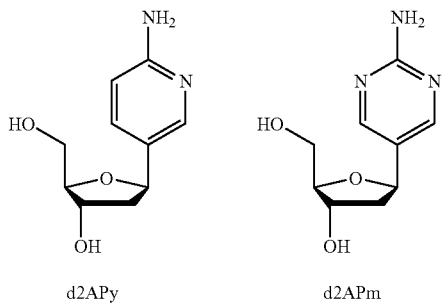

d2APy        d2APm (Minor groove hydration is critical to the stability of DNA duplexes. Lan, T.; McLaughlin, L. W. *J. Am. Chem. Soc.,* 2000, 122, 6512-13)

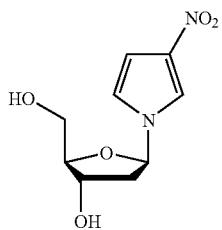

(Effect of the Universal base 3-nitropyrrole on the selectivity of neighboring natural bases. Oliver, J. S.; Parker, K. A.; Suggs, J. W. *Organic Lett.,* 2001, 3, 1977-1980. 2. Effect of the 1-(2'-deoxy-β-D-ribofuranosyl)-3-nitropyrrol residue on the stability of DNA duplexes and triplexes. Amosova, O.; George J.; Fresco, J. R. *Nucleic Acids Res.,* 1997, 25, 1930-1934. 3. Synthesis, structure and deoxyribonucleic acid sequencing with a universal nucleosides: 1-(2'-deoxy-β-D-ribofuranosyl)-3-nitropyrrole. Bergstrom, D. E.; Zhang, P.; Toma, P. H.; Andrews, P. C.; Nichols, R. *J. Am. Chem. Soc.,* 1995, 117, 1201-1209)

(

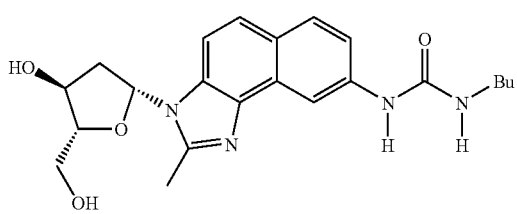

-continued

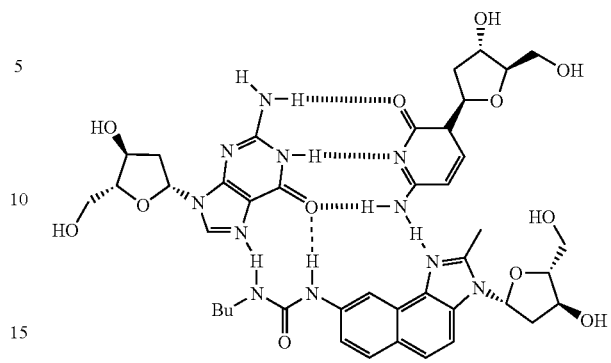

(Model studies directed toward a general triplex DNA recognition scheme: a novel DNA base that binds a CG base-pair in an organic solvent. Zimmerman, S. C.; Schmitt, P. *J. Am. Chem. Soc.,* 1995, 117, 10769-10770)

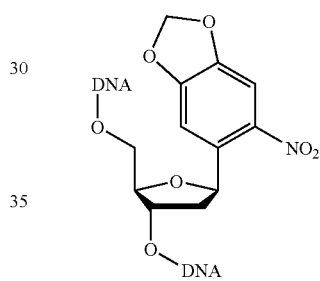

(A universal, photocleavable DNA base: nitropiperonyl 2'-deoxyriboside. *J. Org. Chem.,* 2001, 66, 2067-2071)

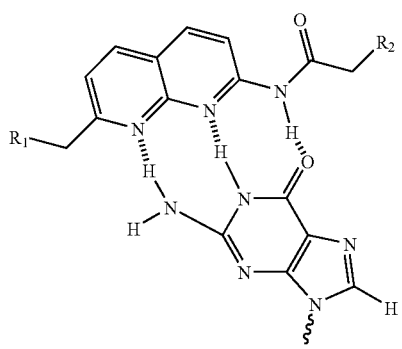

(Recognition of a single guanine bulge by 2-acylamino-1, 8-naphthyridine. Nakatani, K.; Sando, S.; Saito, I. *J. Am. Chem. Soc.,* 2000, 122, 2172-2177. b. Specific binding of 2-amino-1,8-naphthyridine into single guanine bulge as evidenced by photooxidation of GC doublet, Nakatani, K.; Sando, S.; Yoshida, K.; Saito, I. *Bioorg. Med. Chem. Lett.,* 2001, 11, 335-337)

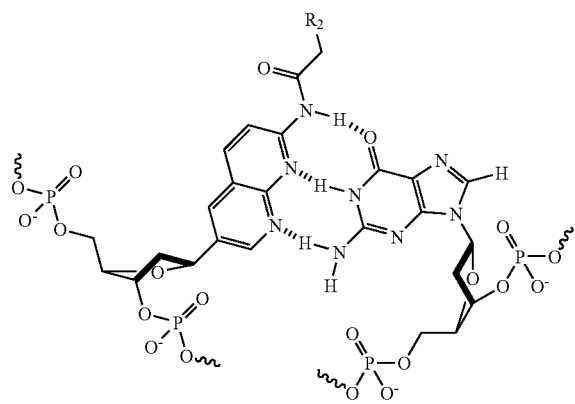

Other universal bases can have the following formulas:

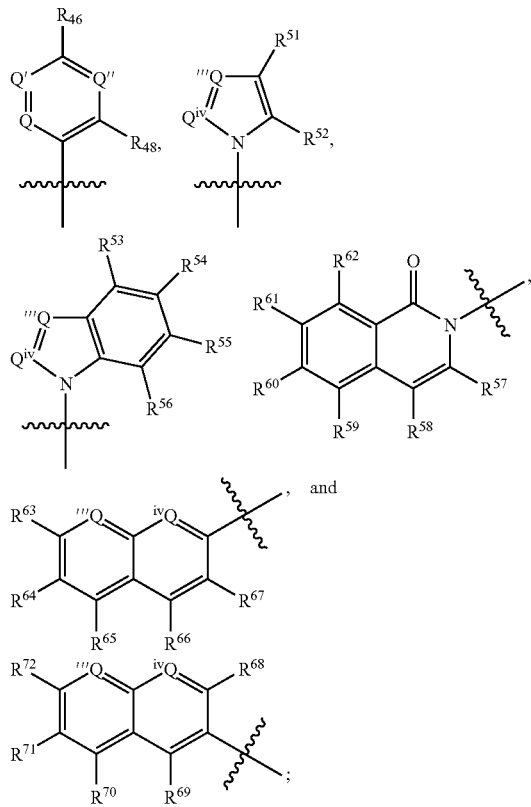

wherein:

Q is N or $CR^{44}$;
Q' is N or $CR^{45}$;
Q'' is N or $CR^{47}$;
Q''' is N or $CR^{49}$;
$Q^{iv}$ is N or $CR^{50}$;

$R^{44}$ is hydrogen, halo, hydroxy, nitro, protected hydroxy, $NH_2$, $NHR^b$, or $NR^bR^c$, $C_1$-$C_6$ alkyl, $C_6$-$C_{10}$ aryl, $C_6$-$C_{10}$ heteroaryl, $C_3$-$C_8$ heterocyclyl, or when taken together with $R^{45}$ forms —$OCH_2O$—;

$R^{45}$ is hydrogen, halo, hydroxy, nitro, protected hydroxy, $NH_2$, $NHR^b$, or $NR^bR^c$, $C_1$-$C_6$ alkyl, $C_6$-$C_{10}$ aryl, $C_6$-$C_{10}$ heteroaryl, $C_3$-$C_8$ heterocyclyl, or when taken together with $R^{44}$ or $R^{46}$ forms —$OCH_2O$—;

$R^{46}$ is hydrogen, halo, hydroxy, nitro, protected hydroxy, $NH_2$, $NHR^b$, or $NR^bR^c$, $C_1$-$C_6$ alkyl, $C_6$-$C_{10}$ aryl, $C_6$-$C_{10}$ heteroaryl, $C_3$-$C_8$ heterocyclyl, or when taken together with $R^{45}$ or $R^{47}$ forms —$OCH_2O$—;

$R^{47}$ is hydrogen, halo, hydroxy, nitro, protected hydroxy, $NH_2$, $NHR^b$, or $NR^bR^c$, $C_1$-$C_6$ alkyl, $C_6$-$C_{10}$ aryl, $C_6$-$C_{10}$ heteroaryl, $C_3$-$C_8$ heterocyclyl, or when taken together with $R^{46}$ or $R^{48}$ forms —$OCH_2O$—;

$R^{48}$ is hydrogen, halo, hydroxy, nitro, protected hydroxy, $NH_2$, $NHR^b$, or $NR^bR^c$, $C_1$-$C_6$ alkyl, $C_6$-$C_{10}$ aryl, $C_6$-$C_{10}$ heteroaryl, $C_3$-$C_8$ heterocyclyl, or when taken together with $R^{47}$ forms —$OCH2O$—;

$R^{49}$ $R^{50}$, $R^{51}$, $R^{52}$, $R^{53}$, $R^{54}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, and $R^{72}$ are each independently selected from hydrogen, halo, hydroxy, nitro, protected hydroxy, $NH_2$, $NHR^b$, or $NR^bR^c$, $C_1$-$C_6$ alkyl, $C_2$-$C_6$ alkynyl, $C_6$-$C_{10}$ aryl, $C_6$-$C_{10}$ heteroaryl, $C_3$-$C_8$ heterocyclyl, $NC(O)R^{17}$, or $NC(O)R^o$;

$R^{55}$ is hydrogen, halo, hydroxy, nitro, protected hydroxy, $NH_2$, $NHR^b$, or $NR^bR^c$, $C_1$-$C_6$ alkyl, $C_2$-$C_6$ alkynyl, $C_6$-$C_{10}$ aryl, $C_6$-$C_{10}$ heteroaryl, $C_3$-$C_8$ heterocyclyl, $NC(O)R^{17}$, or $NC(O)R^o$, or when taken together with $R^{56}$ forms a fused aromatic ring which may be optionally substituted;

$R^{56}$ is hydrogen, halo, hydroxy, nitro, protected hydroxy, $NH_2$, $NHR^b$, or $NR^bR^c$, $C_1$-$C_6$ alkyl, $C_2$-$C_6$ alkynyl, $C_6$-$C_{10}$ aryl, $C_6$-$C_{10}$ heteroaryl, $C_3$-$C_8$ heterocyclyl, $NC(O)R^{17}$, or $NC(O)R^o$, or when taken together with $R^{55}$ forms a fused aromatic ring which may be optionally substituted;

$R^{17}$ is halo, $NH_2$, $NHR^b$, or $NR^bR^c$;

$R^b$ is $C_1$-$C_6$ alkyl or a nitrogen protecting group;

$R^c$ is $C_1$-$C_6$ alkyl; and $R^o$ is alkyl optionally substituted with halo, hydroxy, nitro, protected hydroxy, $NH_2$, $NHR^b$, or $NR^bR^c$, $C_1$-$C_6$ alkyl, $C_2$-$C_6$ alkynyl, $C_6$-$C_{10}$ aryl, $C_6$-$C_{10}$ heteroaryl, $C_3$-$C_8$ heterocyclyl, $NC(O)R^{17}$, or $NC(O)R^o$.

Examples of universal bases include:

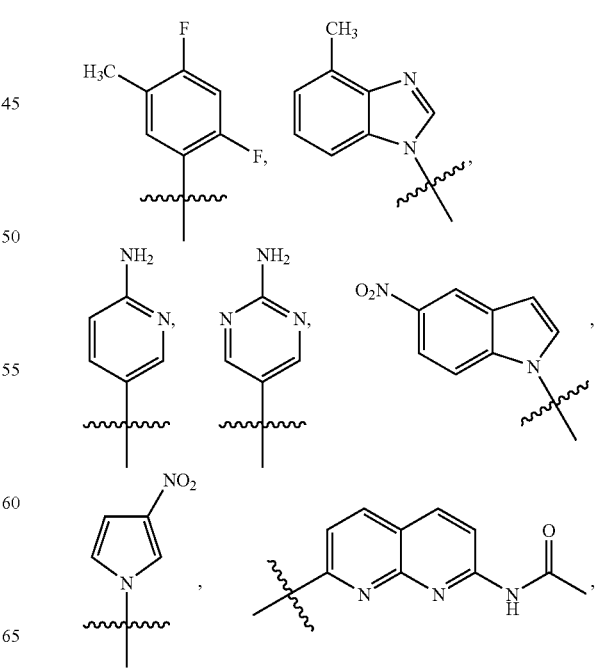

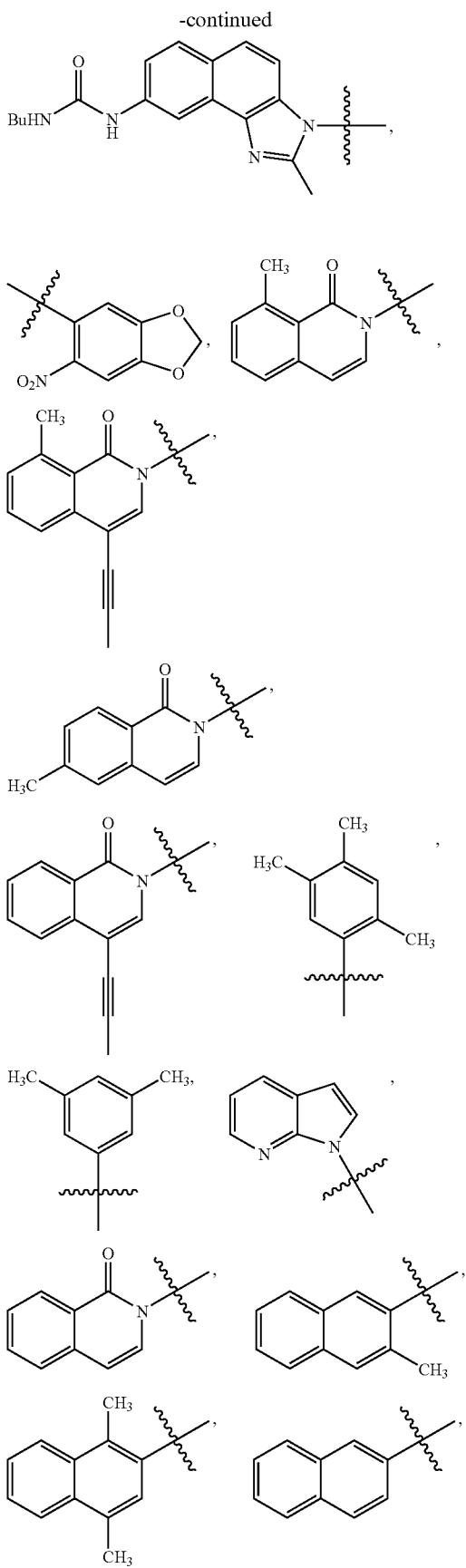

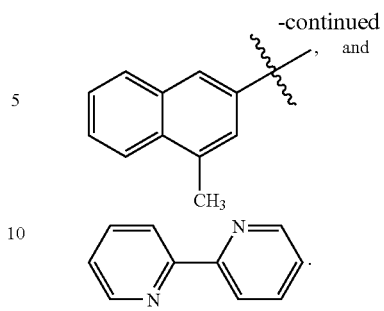

Asymmetrical Modifications

An RNA, e.g., an iRNA agent, can be asymmetrically modified as described herein, and as described in International Application Serial No. PCT/US04/07070, filed Mar. 8, 2004, which is hereby incorporated by reference.

In addition, the invention includes iRNA agents having asymmetrical modifications and another element described herein. E.g., the invention includes an iRNA agent described herein, e.g., a palindromic iRNA agent, an iRNA agent having a non canonical pairing, an iRNA agent which targets a gene described herein, e.g., an SNCA gene, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates an asymmetrical modification.

An asymmetrically modified iRNA agent is one in which a strand has a modification which is not present on the other strand. An asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. E.g., an asymmetrical modification can: confer resistance to degradation, an alteration in half life; target the iRNA agent to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting.

While not wishing to be bound by theory or any particular mechanistic model, it is believed that asymmetrical modification allows an iRNA agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., targeting moieties, can add large bulky groups that, e.g., can interfere with the cleavage activity of the RISC complex, such modifications are preferably placed on the sense strand. Thus, targeting moieties, especially bulky ones (e.g. cholesterol), are preferentially added to the sense strand. In one embodiment, an asymmetrical modification in which a phosphate of the backbone is substituted with S, e.g., a phosphorothioate modification, is present in the antisense strand, and a 2' modification, e.g., 2' OMe is present in the sense strand. A targeting moiety can be present at either (or both) the 5' or 3' end of the sense strand of the iRNA agent. In a preferred example, a P of the backbone is replaced with S in the antisense strand, 2'OMe is present in the sense strand, and a targeting moiety is added to either the 5' or 3' end of the sense strand of the iRNA agent.

In a preferred embodiment an asymmetrically modified iRNA agent has a modification on the sense strand which modification is not found on the antisense strand and the antisense strand has a modification which is not found on the sense strand.

Each strand can include one or more asymmetrical modifications. By way of example: one strand can include a first asymmetrical modification which confers a first property on the iRNA agent and the other strand can have a second asymmetrical modification which confers a second property on the iRNA. E.g., one strand, e.g., the sense strand can have a modification which targets the iRNA agent to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, e.g., because the modifications affect other properties as well. E.g., since some changes can affect RISC activity these modifications are chosen for the sense strand.

In one embodiment, one strand has an asymmetrical 2' modification, e.g., a 2' OMe modification, and the other strand has an asymmetrical modification of the phosphate backbone, e.g., a phosphorothioate modification. So, in one embodiment the antisense strand has an asymmetrical 2' OMe modification and the sense strand has an asymmetrical phosphorothioate modification (or vice versa). In a particularly preferred embodiment, the RNAi agent will have asymmetrical 2'-O alkyl, preferably, 2'-OMe modifications on the sense strand and asymmetrical backbone P modification, preferably a phosphorothioate modification in the antisense strand. There can be one or multiple 2'-OMe modifications, e.g., at least 2, 3, 4, 5, or 6, of the subunits of the sense strand can be so modified. There can be one or multiple phosphorothioate modifications, e.g., at least 2, 3, 4, 5, or 6, of the subunits of the antisense strand can be so modified. It is preferable to have an iRNA agent wherein there are multiple 2'-OMe modifications on the sense strand and multiple phophorothioate modifications on the antisense strand. All of the subunits on one or both strands can be so modified. A particularly preferred embodiment of multiple asymmetric modifications on both strands has a duplex region about 20-21, and preferably 19, subunits in length and one or two 3' overhangs of about 2 subunits in length.

Asymmetrical modifications are useful for promoting resistance to degradation by nucleases, e.g., endonucleases. iRNA agents can include one or more asymmetrical modifications which promote resistance to degradation. In preferred embodiments the modification on the antisense strand is one which will not interfere with silencing of the target, e.g., one which will not interfere with cleavage of the target. Most if not all sites on a strand are vulnerable, to some degree, to degradation by endonucleases. One can determine sites which are relatively vulnerable and insert asymmetrical modifications which inhibit degradation. It is often desirable to provide asymmetrical modification of a UA site in an iRNA agent, and in some cases it is desirable to provide the UA sequence on both strands with asymmetrical modification. Examples of modifications which inhibit endonucleolytic degradation can be found herein. Particularly favored modifications include: 2' modification, e.g., provision of a 2' OMe moiety on the U, especially on a sense strand; modification of the backbone, e.g., with the replacement of an O with an S, in the phosphate backbone, e.g., the provision of a phosphorothioate modification, on the U or the A or both, especially on an antisense strand; replacement of the U with a C5 amino linker; replacement of the A with a G (sequence changes are preferred to be located on the sense strand and not the antisense strand); and modification of the at the 2', 6', 7', or 8' position. Preferred embodiments are those in which one or more of these modifications are present on the sense but not the antisense strand, or embodiments where the antisense strand has fewer of such modifications.

Asymmetrical modification can be used to inhibit degradation by exonucleases. Asymmetrical modifications can include those in which only one strand is modified as well as those in which both are modified. In preferred embodiments the modification on the antisense strand is one which will not interfere with silencing of the target, e.g., one which will not interfere with cleavage of the target. Some embodiments will have an asymmetrical modification on the sense strand, e.g., in a 3' overhang, e.g., at the 3' terminus, and on the antisense strand, e.g., in a 3' overhang, e.g., at the 3' terminus. If the modifications introduce moieties of different size it is preferable that the larger be on the sense strand. If the modifications introduce moieties of different charge it is preferable that the one with greater charge be on the sense strand.

Examples of modifications which inhibit exonucleolytic degradation can be found herein. Particularly favored modifications include: 2' modification, e.g., provision of a 2' OMe moiety in a 3' overhang, e.g., at the 3' terminus (3' terminus means at the 3' atom of the molecule or at the most 3' moiety, e.g., the most 3' P or 2' position, as indicated by the context); modification of the backbone, e.g., with the replacement of a P with an S, e.g., the provision of a phosphorothioate modification, or the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrolidine in a 3' overhang, e.g., at the 3' terminus; modification with naproxene, ibuprofen, or other moieties which inhibit degradation at the 3' terminus. Preferred embodiments are those in which one or more of these modifications are present on the sense but not the antisense strand, or embodiments where the antisense strand has fewer of such modifications.

Modifications, e.g., those described herein, which affect targeting can be provided as asymmetrical modifications. Targeting modifications which can inhibit silencing, e.g., by inhibiting cleavage of a target, can be provided as asymmetrical modifications of the sense strand. A biodistribution altering moiety, e.g., cholesterol, can be provided in one or more, e.g., two, asymmetrical modifications of the sense strand. Targeting modifications which introduce moieties having a relatively large molecular weight, e.g., a molecular weight of more than 400, 500, or 1000 daltons, or which introduce a charged moiety (e.g., having more than one positive charge or one negative charge) can be placed on the sense strand.

Modifications, e.g., those described herein, which modulate, e.g., increase or decrease, the affinity of a strand for its compliment or target, can be provided as asymmetrical modifications. These include: 5 methyl U; 5 methyl C; pseudouridine, Locked nucleic acids include: 2 thio U and 2-amino-A. In some embodiments one or more of these is provided on the antisense strand.

iRNA agents have a defined structure, with a sense strand and an antisense strand, and in many cases short single strand overhangs, e.g., of 2 or 3 nucleotides are present at one or both 3' ends. Asymmetrical modification can be used to optimize the activity of such a structure, e.g., by being placed selectively within the iRNA. E.g., the end region of the iRNA agent defined by the 5' end of the sense strand and the 3' end of the antisense strand is important for function. This region can include the terminal 2, 3, or 4 paired nucleotides and any 3' overhang. In preferred embodiments asymmetrical modifications which result in one or more of the following are used: modifications of the 5' end of the sense strand which inhibit kinase activation of the sense strand, including, e.g., attachments of conjugates which target the molecule or the use modifications which protect against 5' exonucleolytic degradation; or modifications of either strand, but preferably the sense strand, which enhance binding between the sense and antisense strand and thereby promote a "tight" structure at this end of the molecule.

The end region of the iRNA agent defined by the 3' end of the sense strand and the 5'end of the antisense strand is also important for function. This region can include the terminal 2, 3, or 4 paired nucleotides and any 3' overhang. Preferred embodiments include asymmetrical modifications of either strand, but preferably the sense strand, which decrease binding between the sense and antisense strand and thereby promote an "open" structure at this end of the molecule. Such modifications include placing conjugates which target the molecule or modifications which promote nuclease resistance on the sense strand in this region. Modification of the antisense strand which inhibit kinase activation are avoided in preferred embodiments.

Exemplary modifications for asymmetrical placement in the sense strand include the following:

(a) backbone modifications, e.g., modification of a backbone P, including replacement of P with S, or P substituted with alkyl or allyl, e.g., Me, and dithioates (S—P=S); these modifications can be used to promote nuclease resistance;

(b) 2'-O alkyl, e.g., 2'-OMe, 3'-O alkyl, e.g., 3'-OMe (at terminal and/or internal positions); these modifications can be used to promote nuclease resistance or to enhance binding of the sense to the antisense strand, the 3' modifications can be used at the 5' end of the sense strand to avoid sense strand activation by RISC;

(c) 2'-5' linkages (with 2'-H, 2'-OH and 2'-OMe and with P=O or P=S) these modifications can be used to promote nuclease resistance or to inhibit binding of the sense to the antisense strand, or can be used at the 5' end of the sense strand to avoid sense strand activation by RISC;

(d) L sugars (e.g., L ribose, L-arabinose with 2'-H, 2'-OH and 2'-OMe); these modifications can be used to promote nuclease resistance or to inhibit binding of the sense to the antisense strand, or can be used at the 5' end of the sense strand to avoid sense strand activation by RISC;

(e) modified sugars (e.g., locked nucleic acids (LNA's), hexose nucleic acids (HNA's) and cyclohexene nucleic acids (CeNA's)); these modifications can be used to promote nuclease resistance or to inhibit binding of the sense to the antisense strand, or can be used at the 5' end of the sense strand to avoid sense strand activation by RISC;

(f) nucleobase modifications (e.g., C-5 modified pyrimidines, N-2 modified purines, N-7 modified purines, N-6 modified purines), these modifications can be used to promote nuclease resistance or to enhance binding of the sense to the antisense strand;

(g) cationic groups and Zwitterionic groups (preferably at a terminus), these modifications can be used to promote nuclease resistance;

(h) conjugate groups (preferably at terminal positions), e.g., naproxen, biotin, cholesterol, ibuprofen, folic acid, peptides, and carbohydrates; these modifications can be used to promote nuclease resistance or to target the molecule, or can be used at the 5' end of the sense strand to avoid sense strand activation by RISC.

Exemplary modifications for asymmetrical placement in the antisense strand include the following:

(a) backbone modifications, e.g., modification of a backbone P, including replacement of P with S, or P substituted with alkyl or allyl, e.g., Me, and dithioates (S—P=S);

(b) 2'-O alkyl, e.g., 2'-OMe, (at terminal positions);

(c) 2'-5' linkages (with 2'-H, 2'-OH and 2'-OMe) e.g., terminal at the 3' end); e.g., with P=O or P=S preferably at the 3'-end, these modifications are preferably excluded from the 5' end region as they may interfere with RISC enzyme activity such as kinase activity;

(d) L sugars (e.g, L ribose, L-arabinose with 2'-H, 2'-OH and 2'-OMe); e.g., terminal at the 3' end; e.g., with P=O or P=S preferably at the 3'-end, these modifications are preferably excluded from the 5' end region as they may interfere with kinase activity;

(e) modified sugars (e.g., LNA's, HNA's and CeNA's); these modifications are preferably excluded from the 5' end region as they may contribute to unwanted enhancements of paring between the sense and antisense strands, it is often preferred to have a "loose" structure in the 5' region, additionally, they may interfere with kinase activity;

(f) nucleobase modifications (e.g., C-5 modified pyrimidines, N-2 modified purines, N-7 modified purines, N-6 modified purines);

(g) cationic groups and Zwitterionic groups (preferably at a terminus);

cationic groups and Zwitterionic groups at 2'-position of sugar; 3'-position of the sugar; as nucleobase modifications (e.g., C-5 modified pyrimidines, N-2 modified purines, N-7 modified purines, N-6 modified purines);

conjugate groups (preferably at terminal positions), e.g., naproxen, biotin, cholesterol, ibuprofen, folic acid, peptides, and carbohydrates, but bulky groups or generally groups which inhibit RISC activity should are less preferred.

The 5'-OH of the antisense strand should be kept free to promote activity. In some preferred embodiments modifications that promote nuclease resistance should be included at the 3' end, particularly in the 3' overhang.

In another aspect, the invention features a method of optimizing, e.g., stabilizing, an iRNA agent. The method includes selecting a sequence having activity, introducing one or more asymmetric modifications into the sequence, wherein the introduction of the asymmetric modification optimizes a property of the iRNA agent but does not result in a decrease in activity.

The decrease in activity can be less than a preselected level of decrease. In preferred embodiments decrease in activity means a decrease of less than 5, 10, 20, 40, or 50% activity, as compared with an otherwise similar iRNA lacking the introduced modification. Activity can, e.g., be measured in vivo, or in vitro, with a result in either being sufficient to demonstrate the required maintenance of activity.

The optimized property can be any property described herein and in particular the properties discussed in the section on asymmetrical modifications provided herein. The modification can be any asymmetrical modification, e.g., an asymmetric modification described in the section on asymmetrical modifications described herein. Particularly preferred asymmetric modifications are 2'-O alkyl modifications, e.g., 2'-OMe modifications, particularly in the sense sequence, and modifications of a backbone O, particularly phosphorothioate modifications, in the antisense sequence.

In a preferred embodiment a sense sequence is selected and provided with an asymmetrical modification, while in other embodiments an antisense sequence is selected and provided with an asymmetrical modification. In some embodiments both sense and antisense sequences are selected and each provided with one or more asymmetrical modifications.

Multiple asymmetric modifications can be introduced into either or both of the sense and antisense sequence. A sequence can have at least 2, 4, 6, 8, or more modifications and all or substantially all of the monomers of a sequence can be modified.

Z-X-Y Architecture

An RNA, e.g., an iRNA agent, can have a Z-X-Y architecture or structure such as those described herein. In addition, an iRNA agent can have a Z-X-Y structure and another element described herein. E.g., the invention includes an iRNA agent described herein, e.g., a palindromic iRNA agent, an iRNA agent having a non canonical pairing, an iRNA agent which targets a gene described herein, e.g., an SNCA gene, an iRNA associated with an amphipathic delivery agent described herein, an iRNA associated with a drug delivery module described herein, an iRNA agent administered as described herein, or an iRNA agent formulated as described herein, which also incorporates a Z-X-Y architecture.

Thus, an iRNA agent can have a first segment, the Z region, a second segment, the X region, and optionally a third region, the Y region:

Z-X-Y.

It may be desirable to modify subunits in one or both of Z and/or Y on one hand and X on the other hand. In some cases they will have the same modification or the same class of modification but it will more often be the case that the modifications made in Z and/or Y will differ from those made in X.

The Z region typically includes a terminus of an iRNA agent. The length of the Z region can vary, but will typically be from 2-14, more preferably 2-10, subunits in length. It typically is single stranded, i.e., it will not base pair with bases of another strand, though it may in some embodiments self associate, e.g., to form a loop structure. Such structures can be formed by the end of a strand looping back and forming an intrastrand duplex. E.g., 2, 3, 4, 5 or more intra-strand bases pairs can form, having a looped out or connecting region, typically of 2 or more subunits which do not pair. This can occur at one or both ends of a strand. A typical embodiment of a Z region is a single strand overhang, e.g., an overhang of the length described elsewhere herein. The Z region can thus be or include a 3' or 5' terminal single strand. It can be sense or antisense strand but if it is antisense it is preferred that it is a 3-overhang. Typical inter-subunit bonds in the Z region include: P=O; P=S; S—P=S; P—NR$_2$; and P—BR$_2$. Chiral P=X, where X is S, N, or B) inter-subunit bonds can also be present. Other preferred Z region subunit modifications (also discussed elsewhere herein) can include: 3'-OR, 3'SR, 2'-OMe, 3'-OMe, and 2'OH modifications and moieties; alpha configuration bases; and 2' arabino modifications.

The X region will in most cases be duplexed, in the case of a single strand iRNA agent, with a corresponding region of the single strand, or in the case of a double stranded iRNA agent, with the corresponding region of the other strand. The length of the X region can vary but will typically be between 10-45 and more preferably between 15 and 35 subunits. Particularly preferred region X's will include 17, 18, 19, 29, 21, 22, 23, 24, or 25 nucleotide pairs, though other suitable lengths are described elsewhere herein and can be used. Typical X region subunits include 2'-OH subunits. In typical embodiments phosphate inter-subunit bonds are preferred while phophorothioate or non-phosphate bonds are absent. Other modifications preferred in the X region include: modifications to improve binding, e.g., nucleobase modifications; cationic nucleobase modifications; and C-5 modified pyrimidines, e.g., allylamines. Some embodiments have 4 or more consecutive 2'OH subunits. While the use of phosphorothioate is sometimes non preferred they can be used if they connect less than 4 consecutive 2'OH subunits.

The Y region will generally conform to the parameters set out for the Z regions. However, the X and Z regions need not be the same, different types and numbers of modifications can be present, and in fact, one will usually be a 3' overhang and one will usually be a 5' overhang.

In a preferred embodiment the iRNA agent will have a Y and/or Z region each having ribonucleosides in which the 2'-OH is substituted, e.g., with 2'-OMe or other alkyl; and an X region that includes at least four consecutive ribonucleoside subunits in which the 2'-OH remains unsubstituted.

The subunit linkages (the linkages between subunits) of an iRNA agent can be modified, e.g., to promote resistance to degradation. Numerous examples of such modifications are disclosed herein, one example of which is the phosphorothioate linkage. These modifications can be provided between the subunits of any of the regions, Y, X, and Z. However, it is preferred that their occurrence is minimized and in particular it is preferred that consecutive modified linkages be avoided.

In a preferred embodiment the iRNA agent will have a Y and Z region each having ribonucleosides in which the 2'-OH is substituted, e.g., with 2'-OMe; and an X region that includes at least four consecutive subunits, e.g., ribonucleoside subunits in which the 2'-OH remains unsubstituted.

As mentioned above, the subunit linkages of an iRNA agent can be modified, e.g., to promote resistance to degradation. These modifications can be provided between the subunits of any of the regions, Y, X, and Z. However, it is preferred that they are minimized and in particular it is preferred that consecutive modified linkages be avoided.

Thus, in a preferred embodiment, not all of the subunit linkages of the iRNA agent are modified and more preferably the maximum number of consecutive subunits linked by other than a phosphodiester bond will be 2, 3, or 4. Particularly preferred iRNA agents will not have four or more consecutive subunits, e.g., 2'-hydroxyl ribonucleoside subunits, in which each subunit is joined by modified linkages—i.e. linkages that have been modified to stabilize them from degradation as compared to the phosphodiester linkages that naturally occur in RNA and DNA.

It is particularly preferred to minimize the occurrence in region X. Thus, in preferred embodiments each of the nucleoside subunit linkages in X will be phosphodiester linkages, or if subunit linkages in region X are modified, such modifications will be minimized. E.g., although the Y and/or Z regions can include inter subunit linkages which have been stabilized against degradation, such modifications will be minimized in the X region, and in particular consecutive modifications will be minimized. Thus, in preferred embodiments the maximum number of consecutive subunits linked by other than a phosphodiester bond will be 2, 3, or 4. Particularly preferred X regions will not have four or more consecutive subunits, e.g., 2'-hydroxyl ribonucleoside subunits, in which each subunits is joined by modified linkages—i.e., linkages that have been modified to stabilize them from degradation as compared to the phosphodiester linkages that naturally occur in RNA and DNA.

In a preferred embodiment Y and/or Z will be free of phosphorothioate linkages, though either or both may contain other modifications, e.g., other modifications of the subunit linkages.

In a preferred embodiment, region X, or in some cases, the entire iRNA agent, has no more than 3 or no more than 4 subunits having identical 2' moieties.

In a preferred embodiment, region X, or in some cases, the entire iRNA agent, has no more than 3 or no more than 4 subunits having identical subunit linkages.

In a preferred embodiment, one or more phosphorothioate linkages (or other modifications of the subunit linkage) are present in Y and/or Z, but such modified linkages do not connect two adjacent subunits, e.g., nucleosides, having a 2' modification, e.g., a 2'-O-alkyl moiety. E.g., any adjacent 2'-O-alkyl moieties in the Y and/or Z, are connected by a linkage other than a phosphorothioate linkage.

In a preferred embodiment, each of Y and/or Z independently has only one phosphorothioate linkage between adjacent subunits, e.g., nucleosides, having a 2' modification, e.g., 2'-O-alkyl nucleosides. If there is a second set of adjacent subunits, e.g., nucleosides, having a 2' modification, e.g., 2'-O-alkyl nucleosides, in Y and/or Z that second set is connected by a linkage other than a phosphorothioate linkage, e.g., a modified linkage other than a phosphorothioate linkage.

In a preferred embodiment, each of Y and/or Z independently has more than one phosphorothioate linkage connecting adjacent pairs of subunits, e.g., nucleosides, having a 2' modification, e.g., 2'-O-alkyl nucleosides, but at least one pair of adjacent subunits, e.g., nucleosides, having a 2' modification, e.g., 2'-O-alkyl nucleosides, are be connected by a linkage other than a phosphorothioate linkage, e.g., a modified linkage other than a phosphorothioate linkage.

In a preferred embodiment one of the above recited limitation on adjacent subunits in Y and or Z is combined with a limitation on the subunits in X. E.g., one or more phosphorothioate linkages (or other modifications of the subunit linkage) are present in Y and/or Z, but such modified linkages do not connect two adjacent subunits, e.g., nucleosides, having a 2' modification, e.g., a 2'-O-alkyl moiety. E.g., any adjacent 2'-O-alkyl moieties in the Y and/or Z, are connected by a linkage other than a phosphorothioate linkage. In addition, the X region has no more than 3 or no more than 4 identical subunits, e.g., subunits having identical 2' moieties or the X region has no more than 3 or no more than 4 subunits having identical subunit linkages.

A Y and/or Z region can include at least one, and preferably 2, 3 or 4 of a modification disclosed herein. Such modifications can be chosen, independently, from any modification described herein, e.g., from nuclease resistant subunits, subunits with modified bases, subunits with modified intersubunit linkages, subunits with modified sugars, and subunits linked to another moiety, e.g., a targeting moiety. In a preferred embodiment more than 1 of such subunit can be present but in some embodiments it is preferred that no more than 1, 2, 3, or 4 of such modifications occur, or occur consecutively. In a preferred embodiment the frequency of the modification will differ between Y and/or Z and X, e.g., the modification will be present one of Y and/or Z or X and absent in the other.

An X region can include at least one, and preferably 2, 3 or 4 of a modification disclosed herein. Such modifications can be chosen, independently, from any modification described herein, e.g., from nuclease resistant subunits, subunits with modified bases, subunits with modified intersubunit linkages, subunits with modified sugars, and subunits linked to another moiety, e.g., a targeting moiety. In a preferred embodiment more than 1 of such subunits can b present but in some embodiments it is preferred that no more than 1, 2, 3, or 4 of such modifications occur, or occur consecutively.

An RRMS (described elsewhere herein) can be introduced at one or more points in one or both strands of a double-stranded iRNA agent. An RRMS can be placed in a Y and/or Z region, at or near (within 1, 2, or 3 positions) of the 3' or 5' end of the sense strand or at near (within 2 or 3 positions of) the 3' end of the antisense strand. In some embodiments it is preferred to not have an RRMS at or near (within 1, 2, or 3 positions of) the 5' end of the antisense strand. An RRMS can be positioned in the X region, and will preferably be positioned in the sense strand or in an area of the antisense strand not critical for antisense binding to the target.

Differential Modification of Terminal Duplex Stability

In one aspect, the invention features an iRNA agent which can have differential modification of terminal duplex stability (DMTDS).

In addition, the invention includes iRNA agents having DMT/DS and another element described herein. E.g., the invention includes an iRNA agent described herein, e.g., a palindromic iRNA agent, an iRNA agent having a non canonical pairing, an iRNA agent which targets a gene described herein, e.g., an SNCA gene, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates DMTDS.

iRNA agents can be optimized by increasing the propensity of the duplex to disassociate or melt (decreasing the free energy of duplex association), in the region of the 5' end of the antisense strand duplex. This can be accomplished, e.g., by the inclusion of subunits, which increase the propensity of the duplex to disassociate or melt in the region of the 5' end of the antisense strand. This can also be accomplished by the attachment of a ligand that increases the propensity of the duplex to disassociate of melt in the region of the 5'end. While not wishing to be bound by theory, the effect may be due to promoting the effect of an enzyme such as a helicase, for example, promoting the effect of the enzyme in the proximity of the 5' end of the antisense strand.

The inventors have also discovered that iRNA agents can be optimized by decreasing the propensity of the duplex to disassociate or melt (increasing the free energy of duplex association), in the region of the 3' end of the antisense strand duplex. This can be accomplished, e.g., by the inclusion of subunits which decrease the propensity of the duplex to disassociate or melt in the region of the 3' end of the antisense strand. It can also be accomplished by the attachment of ligand that decreases the propensity of the duplex to disassociate or melt in the region of the 5'end.

Modifications which increase the tendency of the 5' end of the duplex to dissociate can be used alone or in combination with other modifications described herein, e.g., with modifications which decrease the tendency of the 3' end of the duplex to dissociate. Likewise, modifications which decrease the tendency of the 3' end of the duplex to dissociate can be used alone or in combination with other modifications described herein, e.g., with modifications which increase the tendency of the 5' end of the duplex to dissociate.

Decreasing the Stability of the AS 5' End of the Duplex

Subunit pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation:

| A:U | is preferred over | G:C; |
|---|---|---|
| G:U | is preferred over | G:C; |
| I:C | is preferred over | G:C (I = inosine); | mismatches, e.g., non-canonical or other than canonical pairings (as described elsewhere herein) are preferred over canonical (A:T, A:U, G:C) pairings;

pairings which include a universal base are preferred over canonical pairings.

A typical ds iRNA agent can be diagrammed as follows:

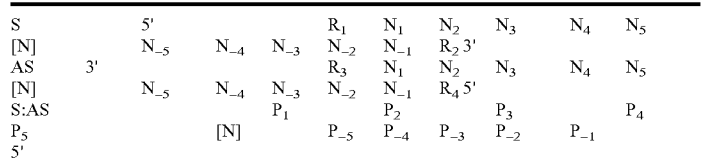

S indicates the sense strand; AS indicates antisense strand; $R_1$ indicates an optional (and nonpreferred) 5' sense strand overhang; $R_2$ indicates an optional (though preferred) 3' sense overhang; $R_3$ indicates an optional (though preferred) 3' antisense sense overhang; $R_4$ indicates an optional (and nonpreferred) 5' antisense overhang; N indicates subunits; [N] indicates that additional subunit pairs may be present; and $P_x$, indicates a paring of sense $N_x$ and antisense $N_x$. Overhangs are not shown in the P diagram. In some embodiments a 3' AS overhang corresponds to region Z, the duplex region corresponds to region X, and the 3' S strand overhang corresponds to region Y, as described elsewhere herein. (The diagram is not meant to imply maximum or minimum lengths, on which guidance is provided elsewhere herein.)

It is preferred that pairings which decrease the propensity to form a duplex are used at 1 or more of the positions in the duplex at the 5' end of the AS strand. The terminal pair (the most 5' pair in terms of the AS strand) is designated as $P_{-1}$, and the subsequent pairing positions (going in the 3' direction in terms of the AS strand) in the duplex are designated, $P_{-2}$, $P_{-3}$, $P_{-4}$, $P_{-5}$, and so on. The preferred region in which to modify or modulate duplex formation is at $P_{-5}$ through $P_{-1}$, more preferably $P_{-4}$ through $P_{-1}$, more preferably $P_{-3}$ through $P_{-1}$ Modification at $P_{-1}$, is particularly preferred, alone or with modification(s) other position(s), e.g., any of the positions just identified. It is preferred that at least 1, and more preferably 2, 3, 4, or 5 of the pairs of one of the recited regions be chosen independently from the group of:

A:U
G:U
I:C
mismatched pairs, e.g., non-canonical or other than canonical pairings or pairings which include a universal base.

In preferred embodiments the change in subunit needed to achieve a pairing which promotes dissociation will be made in the sense strand, though in some embodiments the change will be made in the antisense strand.

In a preferred embodiment the at least 2, or 3, of the pairs in $P_{-1}$, through $P_{-4}$, are pairs which promote dissociation.

In a preferred embodiment the at least 2, or 3, of the pairs in $P_{-1}$, through $P_{-4}$, are A:U.

In a preferred embodiment the at least 2, or 3, of the pairs in $P_{-1}$, through $P_{-4}$, are G:U.

In a preferred embodiment the at least 2, or 3, of the pairs in $P_{-1}$, through $P_{-4}$, are I:C.

In a preferred embodiment the at least 2, or 3, of the pairs in $P_{-1}$, through $P_{-4}$, are mismatched pairs, e.g., non-canonical or other than canonical pairings.

In a preferred embodiment the at least 2, or 3, of the pairs in $P_{-1}$, through $P_{-4}$, are pairings which include a universal base.

Increasing the Stability of the AS 3' End of the Duplex

Subunit pairs can be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability:

| G:C | is preferred over | A:U |
|---|---|---|

Watson-Crick matches (A:T, A:U, G:C) are preferred over non-canonical or other than canonical pairings analogs that increase stability are preferred over Watson-Crick matches (A:T, A:U, G:C)

| 2-amino-A:U | is preferred over | A:U |
|---|---|---|
| 2-thio U or 5 Me-thio-U:A | are preferred over U:A | |
| G-clamp (an analog of C having 4 hydrogen bonds):G | is preferred over C:G | |
| guanadinium-G-clamp:G | is preferred over C:G | |
| pseudo uridine:A | is preferred over U:A | | sugar modifications, e.g., 2' modifications, e.g., 2'F, ENA, or LNA, which enhance binding are preferred over non-modified moieties and can be present on one or both strands to enhance stability of the duplex. It is preferred that pairings which increase the propensity to form a duplex are used at 1 or more of the positions in the duplex at the 3' end of the AS strand. The terminal pair (the most 3' pair in terms of the AS strand) is designated as $P_1$, and the subsequent pairing positions (going in the 5' direction in terms of the AS strand) in the duplex are designated, $P_2$, $P_3$, $P_4$, $P_5$, and so on. The preferred region in which to modify to modulate duplex formation is at $P_5$ through $P_1$, more preferably $P_4$ through $P_1$, more preferably $P_3$ through $P_1$. Modification at $P_1$, is particularly preferred, alone or with modification(s) at other position(s), e.g., any of the positions just identified. It is preferred that at least 1, and more preferably 2, 3, 4, or 5 of the pairs of the recited regions be chosen independently from the group of:

G:C a pair having an analog that increases stability over Watson-Crick matches (A:T, A:U, G:C)

2-amino-A:U 2-thio U or 5 Me-thio-U:A

G-clamp (an analog of C having 4 hydrogen bonds):G guanadinium-G-clamp:G pseudo uridine:A a pair in which one or both subunits has a sugar modification, e.g., a 2' modification, e.g., 2'F, ENA, or LNA, which enhance binding.

In a preferred embodiment the at least 2, or 3, of the pairs in $P_{-1}$, through $P_{-4}$, are pairs which promote duplex stability.

In a preferred embodiment the at least 2, or 3, of the pairs in $P_1$, through $P_4$, are G:C.

In a preferred embodiment the at least 2, or 3, of the pairs in $P_1$, through $P_4$, are a pair having an analog that increases stability over Watson-Crick matches.

In a preferred embodiment the at least 2, or 3, of the pairs in $P_1$, through $P_4$, are 2-amino-A:U.

In a preferred embodiment the at least 2, or 3, of the pairs in $P_1$, through $P_4$, are 2-thio U or 5 Me-thio-U:A.

In a preferred embodiment the at least 2, or 3, of the pairs in $P_1$, through $P_4$, are G-clamp:G.

In a preferred embodiment the at least 2, or 3, of the pairs in $P_1$, through $P_4$, are guanidinium-G-clamp:G.

In a preferred embodiment the at least 2, or 3, of the pairs in $P_1$, through $P_4$, are pseudo uridine:A.

In a preferred embodiment the at least 2, or 3, of the pairs in $P_1$, through $P_4$, are a pair in which one or both subunits has a sugar modification, e.g., a 2' modification, e.g., 2'F, ENA, or LNA, which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

Simultaneously Decreasing the Stability of the AS 5'End of the Duplex and Increasing the Stability of the AS 3' End of the Duplex As is discussed above, an iRNA agent can be modified to both decrease the stability of the AS 5'end of the duplex and increase the stability of the AS 3' end of the duplex. This can be effected by combining one or more of the stability decreasing modifications in the AS 5' end of the duplex with one or more of the stability increasing modifications in the AS 3' end of the duplex. Accordingly a preferred embodiment includes modification in $P_{-5}$ through $P_{-1}$, more preferably $P_{-4}$ through $P_{-1}$ and more preferably $P_{-3}$ through $P_{-1}$. Modification at $P_{-1}$, is particularly preferred, alone or with other position, e.g., the positions just identified. It is preferred that at least 1, and more preferably 2, 3, 4, or 5 of the pairs of one of the recited regions of the AS 5' end of the duplex region be chosen independently from the group of:

A:U

G:U

I:C mismatched pairs, e.g., non-canonical or other than canonical pairings which include a universal base; and a modification in $P_5$ through $P_1$, more preferably $P_4$ through $P_1$ and more preferably $P_3$ through $P_1$. Modification at $P_1$, is particularly preferred, alone or with other position, e.g., the positions just identified. It is preferred that at least 1, and more preferably 2, 3, 4, or 5 of the pairs of one of the recited regions of the AS 3' end of the duplex region be chosen independently from the group of:

G:C a pair having an analog that increases stability over Watson-Crick matches (A:T, A:U, G:C)

2-amino-A:U 2-thio U or 5 Me-thio-U:A

G-clamp (an analog of C having 4 hydrogen bonds):G guanadinium-G-clamp:G pseudo uridine:A a pair in which one or both subunits has a sugar modification, e.g., a 2' modification, e.g., 2'F, ENA, or LNA, which enhance binding.

The invention also includes methods of selecting and making iRNA agents having DMTDS. E.g., when screening a target sequence for candidate sequences for use as iRNA agents one can select sequences having a DMTDS property described herein or one which can be modified, preferably with as few changes as possible, especially to the AS strand, to provide a desired level of DMTDS.

The invention also includes, providing a candidate iRNA agent sequence, and modifying at least one P in $P_{-5}$ through $P_{-1}$ and/or at least one P in $P_5$ through $P_1$ to provide a DMTDS iRNA agent.

DMTDS iRNA agents can be used in any method described herein, e.g., to silence an SNCA RNA, to treat any disorder described herein, e.g., a neurodegenerative disorder, in any formulation described herein, and generally in and/or with the methods and compositions described elsewhere herein. DMTDS iRNA agents can incorporate other modifications described herein, e.g., the attachment of targeting agents or the inclusion of modifications which enhance stability, e.g., the inclusion of nuclease resistant monomers or the inclusion of single strand overhangs (e.g., 3' AS overhangs and/or 3' S strand overhangs) which self associate to form intrastrand duplex structure.

Preferably these iRNA agents will have an architecture described herein.

OTHER EMBODIMENTS

An RNA, e.g., an iRNA agent, can be produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of an iRNA agent and one that produces a transcript that includes the bottom strand of an iRNA agent. When the templates are transcribed, the iRNA agent is produced, and processed into sRNA agent fragments that mediate gene silencing.

In vivo Delivery

An iRNA agent can be linked, e.g., noncovalently linked to a polymer for the efficient delivery of the iRNA agent to a subject, e.g., a mammal, such as a human. The iRNA agent can, for example, be complexed with cyclodextrin. Cyclodextrins have been used as delivery vehicles of therapeutic compounds. Cyclodextrins can form inclusion complexes with drugs that are able to fit into the hydrophobic cavity of the cyclodextrin. In other examples, cyclodextrins form non-covalent associations with other biologically active molecules such as oligonucleotides and derivatives thereof. The use of cyclodextrins creates a water-soluble drug delivery complex, that can be modified with targeting or other functional groups. Cyclodextrin cellular delivery system for oligonucleotides described in U.S. Pat. No. 5,691,316, which is hereby incorporated by reference, are suitable for use in methods of the invention. In this system, an oligonucleotide is noncovalently complexed with a cyclodextrin, or the oligonucleotide is covalently bound to adamantine which in turn is non-covalently associated with a cyclodextrin.

The delivery molecule can include a linear cyclodextrin copolymer or a linear oxidized cyclodextrin copolymer having at least one ligand bound to the cyclodextrin copolymer. Delivery systems, as described in U.S. Pat. No. 6,509,323, herein incorporated by reference, are suitable for use in methods of the invention. An iRNA agent can be bound to the linear cyclodextrin copolymer and/or a linear oxidized cyclodextrin copolymer. Either or both of the cyclodextrin or oxidized cyclodextrin copolymers can be crosslinked to another polymer and/or bound to a ligand.

A composition for iRNA delivery can employ an "inclusion complex," a molecular compound having the characteristic structure of an adduct. In this structure, the "host molecule" spatially encloses at least part of another compound in the delivery vehicle. The enclosed compound (the "guest molecule") is situated in the cavity of the host molecule without affecting the framework structure of the host. A "host" is preferably cyclodextrin, but can be any of the molecules suggested in U.S. Patent Publ. 2003/0008818, herein incorporated by reference.

Cyclodextrins can interact with a variety of ionic and molecular species, and the resulting inclusion compounds belong to the class of "host-guest" complexes. Within the host-guest relationship, the binding sites of the host and guest molecules should be complementary in the stereoelectronic sense. A composition of the invention can contain at least one polymer and at least one therapeutic agent, generally in the form of a particulate composite of the polymer and therapeutic agent, e.g., the iRNA agent. The iRNA agent can contain one or more complexing agents. At least one polymer of the particulate composite can interact with the complexing agent in a host-guest or a guest-host interaction to form an inclusion complex between the polymer and the complexing agent. The polymer and, more particularly, the complexing agent can be used to introduce functionality into the composition. For example, at least one polymer of the particulate composite has host functionality and forms an inclusion complex with a complexing agent having guest functionality. Alternatively, at least one polymer of the particulate composite has guest functionality and forms an inclusion complex with a complexing agent having host functionality. A polymer of the particulate composite can also contain both host and guest functionalities and form inclusion complexes with guest complexing agents and host complexing agents. A polymer with functionality can, for example, facilitate cell targeting and/or cell contact (e.g., targeting or contact to a neural cell), intercellular trafficking, and/or cell entry and release.

Upon forming the particulate composite, the iRNA agent may or may not retain its biological or therapeutic activity. Upon release from the therapeutic composition, specifically, from the polymer of the particulate composite, the activity of the iRNA agent is restored. Accordingly, the particulate composite advantageously affords the iRNA agent protection against loss of activity due to, for example, degradation and offers enhanced bioavailability. Thus, a composition may be used to provide stability, particularly storage or solution stability, to an iRNA agent or any active chemical compound. The iRNA agent may be further modified with a ligand prior to or after particulate composite or therapeutic composition formation. The ligand can provide further functionality. For example, the ligand can be a targeting moiety.

Physiological Effects

The iRNA agents described herein can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, Pan paniscus, Pan troglodytes, Macaca mulatto, or Cynomolgus monkey. The sequence of the iRNA agent could be complementary to sequences within homologous genes, e.g., oncogenes or tumor suppressor genes, of the non-human mammal and the human. By determining the toxicity of the iRNA agent in the non-human mammal, one can extrapolate the toxicity of the iRNA agent in a human. For a more strenuous toxicity test, the iRNA agent can be complementary to a human and more than one, e.g., two or three or more, non-human animals.

The methods described herein can be used to correlate any physiological effect of an iRNA agent on a human, e.g., any unwanted effect, such as a toxic effect, or any positive, or desired effect.

Delivery Module

An RNA, e.g., an iRNA agent described herein, can be used with a drug delivery conjugate or module, such as those described herein. In addition, an iRNA agent described herein, e.g., a palindromic iRNA agent, an iRNA agent having a non canonical pairing, an iRNA agent which targets a gene described herein, e.g., an SNCA gene, an iRNA agent having a chemical modification described herein, e.g., a modification which enhances resistance to degradation, an iRNA agent having an architecture or structure described herein, an iRNA agent administered as described herein, or an iRNA agent formulated as described herein, combined with, associated with, and delivered by such a drug delivery conjugate or module.

The iRNA agents can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane, e.g., an endosome membrane); and (c) a targeting group, e.g., a cell or tissue targeting agent, e.g., a lectin, glycoprotein, lipid or protein, e.g., an antibody, that binds to a specified cell type such as a neural cell in the brain.

An iRNA agent, e.g., iRNA agent or sRNA agent described herein, can be linked, e.g., coupled or bound, to the modular complex. The iRNA agent can interact with the condensing agent of the complex, and the complex can be used to deliver an iRNA agent to a cell, e.g., in vitro or in vivo. For example, the complex can be used to deliver an iRNA agent to a subject in need thereof, e.g., to deliver an iRNA agent to a subject having a disorder, e.g., a disorder described herein, such as a neurodegenerative disease or disorder.

The fusogenic agent and the condensing agent can be different agents or the one and the same agent. For example, a polyamino chain, e.g., polyethyleneimine (PEI), can be the fusogenic and/or the condensing agent.

The delivery agent can be a modular complex. For example, the complex can include a carrier agent linked to one or more of (preferably two or more, more preferably all three of):

(a) a condensing agent (e.g., an agent capable of attracting, e.g., binding, a nucleic acid, e.g., through ionic interaction), (b) a fusogenic agent (e.g., an agent capable of fusing and/or being transported through a cell membrane, e.g., an endosome membrane), and (c) a targeting group, e.g., a cell or tissue targeting agent, e.g., a lectin, glycoprotein, lipid or protein, e.g., an antibody, that binds to a specified cell type such as a neural cell (e.g., a neural cell in the brain). A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyamino acids, multivalent galactose, transferrin, bisphosphonate, polyglutamate, polyaspartate, a lipid, cholesterol, a steroid, bile acid, folate, vitamin B12, biotin, Neproxin, or an RGD peptide or RGD peptide mimetic.

Carrier agents. The carrier agent of a modular complex described herein can be a substrate for attachment of one or more of: a condensing agent, a fusogenic agent, and a targeting group. The carrier agent would preferably lack an endogenous enzymatic activity. The agent would preferably be a biological molecule, preferably a macromolecule. Polymeric biological carriers are preferred. It would also be preferred that the carrier molecule be biodegradable.

The carrier agent can be a naturally occurring substance, such as a protein (e.g., human serum albumin (HSA), low-density lipoprotein (LDL), or globulin); carbohydrate (e.g., a dextran, pullulan, chitin, chitosan, insulin, cyclodextrin or hyaluronic acid); or lipid. The carrier molecule can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Other useful carrier molecules can be identified by routine methods.

A carrier agent can be characterized by one or more of: (a) is at least 1 Da in size; (b) has at least 5 charged groups, preferably between 5 and 5000 charged groups; (c) is present in the complex at a ratio of at least 1:1 carrier agent to fusogenic agent; (d) is present in the complex at a ratio of at least 1:1 carrier agent to condensing agent; (e) is present in the complex at a ratio of at least 1:1 carrier agent to targeting agent.

Fusogenic agents. A fusogenic agent of a modular complex described herein can be an agent that is responsive to, e.g., changes charge depending on, the pH environment. Upon encountering the pH of an endosome, it can cause a physical change, e.g., a change in osmotic properties which disrupts or increases the permeability of the endosome membrane. Preferably, the fusogenic agent changes charge, e.g., becomes protonated, at pH lower than physiological range. For example, the fusogenic agent can become protonated at pH 4.5-6.5. The fusogenic agent can serve to release the iRNA agent into the cytoplasm of a cell after the complex is taken up, e.g., via endocytosis, by the cell, thereby increasing the cellular concentration of the iRNA agent in the cell.

In one embodiment, the fusogenic agent can have a moiety, e.g., an amino group, which, when exposed to a specified pH range, will undergo a change, e.g., in charge, e.g., protonation. The change in charge of the fusogenic agent can trigger a change, e.g., an osmotic change, in a vesicle, e.g., an endocytic vesicle, e.g., an endosome. For example, the fusogenic agent, upon being exposed to the pH environment of an endosome, will cause a solubility or osmotic change substantial enough to increase the porosity of (preferably, to rupture) the endosomal membrane.

The fusogenic agent can be a polymer, preferably a polyamino chain, e.g., polyethyleneimine (PEI). The PEI can be linear, branched, synthetic or natural. The PEI can be, e.g., alkyl substituted PEI, or lipid substituted PEI.

In other embodiments, the fusogenic agent can be polyhistidine, polyimidazole, polypyridine, polypropyleneimine, mellitin, or a polyacetal substance, e.g., a cationic polyacetal. In some embodiment, the fusogenic agent can have an alpha helical structure. The fusogenic agent can be a membrane disruptive agent, e.g., mellittin.

A fusogenic agent can have one or more of the following characteristics: (a) is at least 1 Da in size; (b) has at least 10 charged groups, preferably between 10 and 5000 charged groups, more preferably between 50 and 1000 charged groups; (c) is present in the complex at a ratio of at least 1:1 fusogenic agent to carrier agent; (d) is present in the complex at a ratio of at least 1:1 fusogenic agent to condensing agent; (e) is present in the complex at a ratio of at least 1:1 fusogenic agent to targeting agent.

Other suitable fusogenic agents can be tested and identified by a skilled artisan. The ability of a compound to respond to, e.g., change charge depending on, the pH environment can be tested by routine methods, e.g., in a cellular assay. For example, a test compound is combined or contacted with a cell, and the cell is allowed to take up the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in endosome population in the cells. The test compound can be labeled. In another type of assay, a modular complex described herein is constructed using one or more test or putative fusogenic agents. The modular complex can be constructed using a labeled nucleic acid instead of the iRNA. A two-step assay can be performed, wherein a first assay evaluates the ability of a test compound alone to respond to, e.g., change charge depending on, the pH environment; and a second assay evaluates the ability of a modular complex that includes the test compound to respond to, e.g., change charge depending on, the pH environment.

Condensing agent. The condensing agent of a modular complex described herein can interact with (e.g., attracts, holds, or binds to) an iRNA agent and act to (a) condense, e.g., reduce the size or charge of the iRNA agent and/or (b) protect the iRNA agent, e.g., protect the iRNA agent against degradation. The condensing agent can include a moiety, e.g., a charged moiety, that can interact with a nucleic acid, e.g., an iRNA agent, e.g., by ionic interactions. The condensing agent would preferably be a charged polymer, e.g., a polycationic chain. The condensing agent can be a polylysine (PLL), spermine, spermidine, polyamine, pseudopeptide-polyamine, peptidomimetic polyamine, dendrimer polyamine, arginine, amidine, protamine, cationic lipid, cationic porphyrin, quarternary salt of a polyamine, or an alpha helical peptide.

A condensing agent can have the following characteristics: (a) at least 1 Da in size; (b) has at least 2 charged groups, preferably between 2 and 100 charged groups; (c) is present in the complex at a ratio of at least 1:1 condensing agent to carrier agent; (d) is present in the complex at a ratio of at least 1:1 condensing agent to fusogenic agent; (e) is present in the complex at a ratio of at least 1:1 condensing agent to targeting agent.

Other suitable condensing agents can be tested and identified by a skilled artisan, e.g., by evaluating the ability of a test agent to interact with a nucleic acid, e.g., an iRNA agent. The ability of a test agent to interact with a nucleic acid, e.g., an iRNA agent, e.g., to condense or protect the iRNA agent, can be evaluated by routine techniques. In one assay, a test agent is contacted with a nucleic acid, and the size and/or charge of the contacted nucleic acid is evaluated by a technique suitable to detect changes in molecular mass and/or charge. Such techniques include non-denaturing gel electrophoresis, immunological methods, e.g., immunoprecipitation, gel filtration, ionic interaction chromatography, and the like. A test agent is identified as a condensing agent if it changes the mass and/or charge (preferably both) of the contacted nucleic acid, compared to a control. A two-step assay can also be performed, wherein a first assay evaluates the ability of a test compound alone to interact with, e.g., bind to, e.g., condense the charge and/or mass of, a nucleic acid; and a second assay evaluates the ability of a modular complex that includes the test compound to interact with, e.g., bind to, e.g., condense the charge and/or mass of, a nucleic acid.

Amphipathic Delivery Agents

An RNA, e.g., an iRNA agent, described herein can be used with an amphipathic delivery conjugate or module, such as those described herein. In addition, an iRNA agent described herein, e.g., a palindromic iRNA agent, an iRNA agent having a noncanonical pairing, an iRNA agent which targets a gene described herein, e.g., an SNCA gene, an iRNA agent having a chemical modification described herein, e.g., a modification which enhances resistance to degradation, an iRNA agent having an architecture or structure described herein, an iRNA agent administered as described herein, or an iRNA agent formulated as described herein, combined with, associated with, and delivered by such an amphipathic delivery conjugate.

An amphipathic molecule is a molecule having a hydrophobic and a hydrophilic region. Such molecules can interact with (e.g., penetrate or disrupt) lipids, e.g., a lipid bilayer of a cell. As such, they can serve as delivery agent for an associated (e.g., bound) iRNA (e.g., an iRNA or sRNA described herein). A preferred amphipathic molecule to be used in the compositions described herein (e.g., the amphipathic iRNA constructs described herein) is a polymer. The polymer may have a secondary structure, e.g., a repeating secondary structure.

One example of an amphipathic polymer is an amphipathic polypeptide, e.g., a polypeptide having a secondary structure such that the polypeptide has a hydrophilic and a hybrophobic face. The design of amphipathic peptide structures (e.g., alpha-helical polypeptides) is routine to one of skill in the art. For example, the following references provide guidance: Grell et al. (2001) J Pept Sci 7(3):146-51; Chen et al. (2002) J Pept Res 59(1):18-33; Iwata et al. (1994) J Biol Chem 269(7):4928-33; Cornut et al. (1994) FEBS Lett 349(1):29-33; Negrete et al. (1998) Protein Sci 7(6):1368-79.

Another example of an amphipathic polymer is a polymer made up of two or more amphipathic subunits, e.g., two or more subunits containing cyclic moieties (e.g., a cyclic moiety having one or more hydrophilic groups and one or more hydrophobic groups). For example, the subunit may contain a steroid, e.g., cholic acid; or a aromatic moiety. Such moieties preferably can exhibit atropisomerism, such that they can form opposing hydrophobic and hydrophilic faces when in a polymer structure.

The ability of a putative amphipathic molecule to interact with a lipid membrane, e.g., a cell membrane, can be tested by routine methods, e.g., in a cell free or cellular assay. For example, a test compound is combined or contacted with a synthetic lipid bilayer, a cellular membrane fraction, or a cell, and the test compound is evaluated for its ability to interact with, penetrate, or disrupt the lipid bilayer, cell membrane or cell. The test compound can be labeled in order to detect the interaction with the lipid bilayer, cell membrane, or cell. In another type of assay, the test compound is linked to a reporter molecule or an iRNA agent (e.g., an iRNA or sRNA described herein), and the ability of the reporter molecule or iRNA agent to penetrate the lipid bilayer, cell membrane or cell is evaluated. A two-step assay can also be performed, wherein a first assay evaluates the ability of a test compound alone to interact with a lipid bilayer, cell membrane or cell; and a second assay evaluates the ability of a construct (e.g., a construct described herein) that includes the test compound and a reporter or iRNA agent to interact with a lipid bilayer, cell membrane or cell.

An amphipathic polymer useful in the compositions described herein has at least 2, preferably at least 5, more preferably at least 10, 25, 50, 100, 200, 500, 1000, 2000, 50000 or more subunits (e.g., amino acids or cyclic subunits). A single amphipathic polymer can be linked to one or more, e.g., 2, 3, 5, 1 0 or more iRNA agents (e.g., iRNA or sRNA agents described herein). In some embodiments, an amphipathic polymer can contain both amino acid and cyclic subunits, e.g., aromatic subunits.

The invention features a composition that includes an iRNA agent (e.g., an iRNA or sRNA described herein) in association with an amphipathic molecule. Such compositions may be referred to herein as "amphipathic iRNA constructs." Such compositions and constructs are useful in the delivery or targeting of iRNA agents, e.g., delivery or targeting of iRNA agents to a cell. While not wanting to be bound by theory, such compositions and constructs can increase the porosity of, e.g., can penetrate or disrupt, a lipid (e.g., a lipid bilayer of a cell), e.g., to allow entry of the iRNA agent into a cell.

In one aspect, the invention relates to a composition comprising an iRNA agent (e.g., an iRNA or sRNA agent described herein) linked to an amphipathic molecule. The iRNA agent and the amphipathic molecule may be held in continuous contact with one another by either covalent or noncovalent linkages.

The amphipathic molecule of the composition or construct is preferably other than a phospholipid, e.g., other than a micelle, membrane or membrane fragment.

The amphipathic molecule of the composition or construct is preferably a polymer. The polymer may include two or more amphipathic subunits. One or more hydrophilic groups and one or more hydrophobic groups may be present on the polymer. The polymer may have a repeating secondary structure as well as a first face and a second face. The distribution of the hydrophilic groups and the hydrophobic groups along the repeating secondary structure can be such that one face of the polymer is a hydrophilic face and the other face of the polymer is a hydrophobic face.

The amphipathic molecule can be a polypeptide, e.g., a polypeptide comprising an a-helical conformation as its secondary structure.

In one embodiment, the amphipathic polymer includes one or more subunits containing one or more cyclic moiety (e.g., a cyclic moiety having one or more hydrophilic groups and/or one or more hydrophobic groups). In one embodiment, the polymer is a polymer of cyclic moieties such that the moieties have alternating hydrophobic and hydrophilic groups. For example, the subunit may contain a steroid, e.g., cholic acid. In another example, the subunit may contain an aromatic moiety. The aromatic moiety may be one that can exhibit atropisomerism, e.g., a 2,2'-bis(substituted)-1-1'-binaphthyl or a 2,2'-bis(substituted) biphenyl. A subunit may include an aromatic moiety of Formula (M):

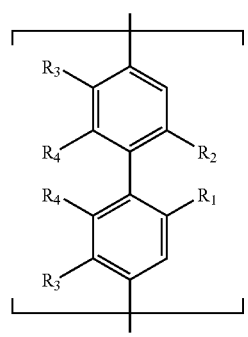

(M)

The invention features a composition that includes an iRNA agent (e.g., an iRNA or sRNA described herein) in association with an amphipathic molecule. Such compositions may be referred to herein as "amphipathic iRNA constructs." Such compositions and constructs are useful in the delivery or targeting of iRNA agents, e.g., delivery or targeting of iRNA agents to a cell. While not wanting to be bound by theory, such compositions and constructs can increase the porosity of, e.g., can penetrate or disrupt, a lipid (e.g., a lipid bilayer of a cell), e.g., to allow entry of the iRNA agent into a cell.

Referring to Formula M, $R_1$ is $C_1$-$C_{100}$ alkyl optionally substituted with aryl, alkenyl, alkynyl, alkoxy or halo and/or optionally inserted with O, S, alkenyl or alkynyl; $C_1$-$C_{100}$ perfluoroalkyl; or $OR_5$.

$R_2$ is hydroxy; nitro; sulfate; phosphate; phosphate ester; sulfonic acid; $OR_6$; or $C_1$-$C_{100}$ alkyl optionally substituted with hydroxy, halo, nitro, aryl or alkyl sulfinyl, aryl or alkyl sulfonyl, sulfate, sulfonic acid, phosphate, phosphate ester, substituted or unsubstituted aryl, carboxyl, carboxylate, amino carbonyl, or alkoxycarbonyl, and/or optionally inserted with O, NH, S, S(O), $SO_2$, alkenyl, or alkynyl.

$R_3$ is hydrogen, or when taken together with $R_4$ forms a fused phenyl ring.

$R_4$ is hydrogen, or when taken together with $R_3$ forms a fused phenyl ring.

$R_5$ is $C_1$-$C_{100}$ alkyl optionally substituted with aryl, alkenyl, alkynyl, alkoxy or halo and/or optionally inserted with O, S, alkenyl or alkynyl; or $C_1$-$C_{100}$ perfluoroalkyl; and $R_6$ is $C_1$-$C_{100}$ alkyl optionally substituted with hydroxy, halo, nitro, aryl or alkyl sulfinyl, aryl or alkyl sulfonyl, sulfate, sulfonic acid, phosphate, phosphate ester, substituted or unsubstituted aryl, carboxyl, carboxylate, amino carbonyl, or alkoxycarbonyl, and/or optionally inserted with O, NH, S, S(O), $SO_2$, alkenyl, or alkynyl.

Increasing Cellular Uptake of dsRNAs

A method of the invention that can include the administration of an iRNA agent and a drug that affects the uptake of the iRNA agent into the cell. The drug can be administered before, after, or at the same time that the iRNA agent is administered. The drug can be covalently linked to the iRNA agent. The drug can have a transient effect on the cell.

The drug can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

iRNA Conjugates

An iRNA agent can be coupled, e.g., covalently coupled, to a second agent. For example, an iRNA agent used to treat a particular disorder can be coupled to a second therapeutic agent, e.g., an agent other than the iRNA agent. The second therapeutic agent can be one which is directed to the treatment of the same disorder. For example, in the case of an iRNA used to treat a disorder characterized by alpha-synuclein aggregates, e.g., PD, the iRNA agent can be coupled to a second agent which is useful for the treatment of PD.

iRNA Production

An iRNA can be produced, e.g., in bulk, by a variety of methods. Exemplary methods include: organic synthesis and RNA cleavage, e.g., in vitro cleavage.

Organic Synthesis. An iRNA can be made by separately synthesizing each respective strand of a double-stranded RNA molecule. The component strands can then be annealed.

A large bioreactor, e.g., the OligoPilot II from Pharmacia Biotec AB (Uppsala Sweden), can be used to produce a large amount of a particular RNA strand for a given iRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the iRNA. Typically, the two complementary strands are produced separately and then annealed, e.g., after release from the solid support and deprotection.

Organic synthesis can be used to produce a discrete iRNA species. The complementary of the species to a particular target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsRNA Cleavage. iRNAs can also be made by cleaving a larger ds iRNA. The cleavage can be mediated in vitro or in vivo. For example, to produce iRNAs by cleavage in vitro, the following method can be used:

In vitro transcription. dsRNA is produced by transcribing a nucleic acid (DNA) segment in both directions. For example, the HiScribe™ RNAi transcription kit (New England Biolabs) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsRNA is cleaved in vitro into iRNAs, for example, using a Dicer or comparable RNAse III-based activity. For example, the dsRNA can be incubated in an in vitro extract from Drosophila or using purified components, e.g. a purified RNAse or RISC complex (RNA-induced silencing complex). See, e.g., Ketting et al. *Genes Dev* 2001 Oct. 15; 15(20):2654-9. and Hammond *Science* 2001 Aug. 10; 293 (5532):1146-50.

dsRNA cleavage generally produces a plurality of iRNA species, each being a particular 21 to 23 nt fragment of a source dsRNA molecule. For example, iRNAs that include sequences complementary to overlapping regions and adjacent regions of a source dsRNA molecule may be present.

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Synthesis of modified and nucleotide surrogate iRNA agents is discussed below.

Formulation

The iRNA agents described herein can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA that can mediated RNAi with respect to a second gene, or with respect to the same gene. Still other preparation can include at least three, five, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than an RNA or a DNA). For example, a iRNA composition for the treatment of a neurodegenerative disease, e.g. PD, might include a known PD therapeutic (e.g., levadopa or depronil)

Targeting

For ease of exposition the formulations, compositions and methods in this section are discussed largely with regard to unmodified iRNAs. It should be understood, however, that these formulations, compositions and methods can be practiced with other iRNA agents, e.g., modified iRNA agents, and such practice is within the invention.

In some embodiments, an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) is targeted to a particular cell. For example, a liposome or particle or other structure that includes a iRNA can also include a targeting moiety that recognizes a specific molecule on a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell.

An antigen, can be used to target an iRNA to a neural cell in the brain.

In one embodiment, the targeting moiety is attached to a liposome. For example, U.S. Pat. No. 6,245,427 describes a method for targeting a liposome using a protein or peptide. In another example, a cationic lipid component of the liposome is derivatized with a targeting moiety. For example, WO 96/37194 describes converting N-glutaryldioleoylphosphatidyl ethanolamine to a N-hydroxysuccinimide activated ester. The product was then coupled to an RGD peptide.

Antibodies

An composition described herein can include an antibody that targets a synuclein polypeptide, e.g., to block synuclein activity and/or inhibit synuclein aggregation. An antibody can be an antibody or a fragment thereof, e.g., an antigen binding portion thereof. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat et al., *Sequences of Proteins of Immunological Interest*, Fifth Edition, U.S. Department of Health and Human Services, NIH Publication No. 91-3242, 1991, and Chothia et al., *J. Mol. Biol.* 196:901-917, 1987, which are incorporated herein by reference). Each VH and VL is composed of three CDR's and four FRs, arranged from amino-terminus to carboxyl-terminus in the following order: FR1, CDR1, FR2, CDR2, FR3, CDR3, FR4.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "antigen-binding fragment" of an antibody (or simply "antibody portion," or "fragment"), as used herein, refers to one or more fragments of a full-length antibody that retain the ability to specifically bind to an antigen (e.g., a polypeptide encoded by an SNCA nucleic acid). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated complementarity determining region (CDR). Furthermore, although the two domains of the Fv fragment, VL and VH, are coded for by separate nucleic acids, they can be joined, using recombinant methods, by a synthetic linker that enables them to be made as a single protein chain in which the VL and VH regions pair to form monovalent molecules (known as single chain Fv (scFv); see e.g., Bird et al., *Science* 242:423-426, 1988, and Huston et al., *Proc. Natl. Acad. Sci. USA* 85:5879-5883, 1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

Anti-protein/anti-peptide antisera or monoclonal antibodies can be made as described herein by using standard protocols (See, for example, *Antibodies: A Laboratory Manual* ed. by Harlow and Lane, Cold Spring Harbor Press, 1988).

A protein described herein, e.g., an alpha synuclein polypeptide, can be used as an immunogen to generate antibodies that bind the component using standard techniques for polyclonal and monoclonal antibody preparation. The full-length component protein can be used or, alternatively, antigenic peptide fragments of the component can be used as immunogens.

Typically, a peptide is used to prepare antibodies by immunizing a suitable subject, (e.g., rabbit, goat, mouse or other mammal) with the immunogen. An appropriate immunogenic preparation can contain, for example, a recombinant form of a protein described herein, e.g., an alpha-synuclein polypeptide. See, e.g., U.S. Pat. No. 5,460,959; and co-pending U.S. applications U.S. Ser. No. 08/334,797; U.S. Ser. No. 08/231,439; U.S. Ser. No. 08/334,455; and U.S. Ser. No. 08/928,881, which are hereby expressly incorporated by, reference in their entirety. The nucleotide and amino acid sequences of alpha-synuclein are known. The preparation can further include an adjuvant, such as Freund's complete or incomplete adjuvant, or similar immunostimulatory agent. Immunization of a suitable subject with an immunogenic protein described herein, e.g., an alpha-synuclein polypeptide, or fragment preparation induces a polyclonal antibody response.

Additionally, antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., *Science* 240:1041-1043, 1988; Liu et al., *PNAS* 84:3439-3443, 1987; Liu et al., *J. Immunol.* 139:3521-3526, 1987; Sun et al., *PNAS* 84:214-218, 1987; Nishimura et al., *Canc. Res.* 47:999-1005, 1987; Wood et al., *Nature* 314:446-449, 1985; and Shaw et al., *J. Natl. Cancer Inst.* 80:1553-1559, 1988); Morrison, S. L., *Science* 229:1202-1207, 1985; Oi et al., *BioTechniques* 4:214, 1986; Winter U.S. Pat. No. 5,225,539; Jones et al., *Nature* 321:552-525, 1986; Verhoeyan et al., *Science* 239:1534, 1988; and Beidler et al., *J. Immunol.* 141: 4053-4060, 1988.

In addition, a human monoclonal antibody directed against a protein described herein, e.g., an alpha-synuclein protein, can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906; Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication WO 94/25585; Rajewsky et al. PCT publication WO 94/04667; Ditullio et al. PCT publication WO 95/17085; Lonberg et al., *Nature* 368:856-859, 1994; Green et al., *Nature Genet.* 7:13-21, 1994; Morrison et al., *Proc. Natl. Acad. Sci. USA* 81:6851-6855, 1994; Bruggeman et al., *Year Immunol* 7:33-40, 1993; Choi et al., *Nature Genet.* 4:117-123, 1993; Tuaillon et al., *PNAS* 90:3720-3724, 1993; Bruggeman et al., *Eur J Immunol* 21:1323-1326, 1991; Duchosal et al. PCT publication WO 93/05796; U.S. Pat. No. 5,411,749; McCune et al., *Science* 241:1632-1639, 1988; Kamel-Reid et al., *Science* 242:1706, 1988; Spanopoulou, *Genes & Development* 8:1030-1042, 1994; and Shinkai et al., *Cell* 68:855-868, 1992. A human antibody-transgenic mouse or an immune deficient mouse engrafted with human antibody-producing cells or tissue can be immunized with a protein described herein, e.g., an alpha-synuclein protein, or an antigenic peptide thereof, and splenocytes from these immunized mice can then be used to create hybridomas. Methods of hybridoma production are well known.

Human monoclonal antibodies against a protein described herein, e.g., an alpha-synuclein polypeptide, can also be prepared by constructing a combinatorial immunoglobulin library, such as a Fab phage display library or an scFv phage display library, using immunoglobulin light chain and heavy chain cDNAs prepared from mRNA derived from lymphocytes of a subject. See, e.g., McCafferty et al. PCT publication WO 92/01047; Marks et al., *J. Mol. Biol.* 222:581-597, 1991; and Griffiths et al., *EMBO J.* 12:725-734, 1993. In addition, a combinatorial library of antibody variable regions can be generated by mutating a known human antibody. For example, a variable region of a human antibody known to bind a protein described herein can be mutated by, for example, using randomly altered mutagenized oligonucleotides, to generate a library of mutated variable regions which can then be screened to bind to a protein described herein, e.g., an alpha-synuclein. Methods of inducing random mutagenesis within the CDR regions of immunoglobulin heavy and/or light chains, methods of crossing randomized heavy and light chains to form pairings and screening methods can be found in, for example, Barbas et al. PCT publication WO 96/07754; and Barbas et al., *Proc. Nat'l Acad. Sci. USA* 89:4457-4461, 1992.

The immunoglobulin library can be expressed by a population of display packages, preferably derived from filamentous phage, to form an antibody display library. Examples of methods and reagents particularly amenable for use in generating an antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al., *Bio/Technology* 9:1370-1372; 1991; Hay et al., *Hum Antibod Hybridomas* 3:81-85, 1992; Huse et al., *Science* 246:1275-1281, 1989; Griffiths et al., 1993, supra; Hawkins et al., *J Mol Biol* 226:889-896, 1992; Clackson et al., *Nature* 352:624-628, 1991; Gram et al., *PNAS* 89:3576-3580, 1992; Garrad et al., *Bio/Technology* 9:1373-1377, 1991; Hoogenboom et al., *Nuc Acid Res* 19:4133-4137, 1991; and Barbas et al., *PNAS* 88:7978-7982, 1991. Once displayed on the surface of a display package (e.g., filamentous phage), the antibody library is screened to identify and isolate packages that express an antibody that binds a protein described herein, e.g., an alpha-synuclein polypeptide. In a preferred embodiment, the primary screening of the library involves panning with an immobilized protein described herein, and display packages expressing antibodies that bind immobilized proteins described herein are selected.

Antisense Nucleic Acid Sequences

Nucleic acid molecules that are antisense to a nucleotide encoding a protein described herein, e.g., an alpha-synuclein polypeptide, can also be used as an agent that inhibits expression of the protein. An "antisense" nucleic acid includes a nucleotide sequence that is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to a portion of a coding strand or the noncoding strand.

The coding strand sequences encoding alpha-synuclein proteins are known. Given a coding strand sequence (e.g., the sequence of a sense strand of a cDNA molecule), antisense nucleic acids can be designed according to the rules of Watson and Crick base pairing. The antisense nucleic acid molecule can be complementary to a portion of the coding or noncoding region of mRNA. For example, the antisense oligonucleotide can be complementary to the region surrounding the translation start site of the mRNA, e.g., the 5' UTR. An antisense oligonucleotide can be, for example, about 10 to 25 nucleotides in length (e.g., 11, 12, 13, 14, 15, 16, 18, 19, 20, or 24 nucleotides in length).

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides that can be used to generate the antisense nucleic acid include 2'-O-methylated nucleotides, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

An antisense agent can include ribonucleotides only, deoxyribonucleotides only (e.g., oligodeoxynucleotides), or both deoxyribonucleotide and ribonucleotide sequences. For example, an antisense agent consisting only of ribonucleotides can hybridize to a complementary RNA, e.g., an alpha-synuclein RNA, and prevent access of the translation machinery to the target RNA transcript, thereby preventing protein synthesis. An antisense molecule including only deoxyribonucleotides, or deoxyribonucleotides and ribonucleotides, e.g., DNA sequence flanked by RNA sequence at the 5' and 3' ends of the antisense agent, can hybridize to a complementary RNA, and the RNA target can be subsequently cleaved by an enzyme, e.g., RNAseH. Degradation of the target RNA prevents translation. The flanking RNA sequences can include 2'-O-methylated nucleotides, and phosphorothioate linkages, and the internal DNA sequence can include phosphorothioate internucleotide linkages. The internal DNA sequence is preferably at least five nucleotides in length when targeting by RNAseH activity is desired.

For increased nuclease resistance, an antisense agent can be further modified by inverting the nucleoside at the 3'-terminus with a 3'-3' linkage. In another alternative, the 3'-terminus can be blocked with an aminoalkyl group.

Zinc Finger Proteins (ZFPs)

Zinc finger protein technology can be used to down-regulate transcription of a candidate target gene, e.g., an SNCA gene. For example, an SNCA gene-specific DNA binding domain can be fused to a repressor domain to down-regulate SNCA gene expression. Zinc finger proteins can be assembled using variable numbers of zinc finger domains of varied specificity providing DNA binding proteins that not only recognize novel sequences but also sequences of varied length. Zinc finger binding proteins for the regulation of gene expression are described, for example, in U.S. Pat. Nos. 6,607,882, and 6,534,261.

The target site recognized by a ZFP can be any suitable site in the target gene (e.g., the SNCA gene) that will allow repression of gene expression by a ZFP, optionally linked to a regulatory domain. Preferred target sites include regions adjacent to, downstream, or upstream of the transcription start site. In addition, target sites can also be located in enhancer regions, repressor sites, RNA polymerase pause sites, and specific regulatory sites (e.g., a REP1 site), sites in the cDNA encoding region or in an expressed sequence tag (EST) coding region. Typically each finger recognizes 2-4 base pairs, with a two finger ZFP binding to a 4 to 7 bp target site, a three finger ZFP binding to a 6 to 10 base pair site, and a six finger ZFP binding to two adjacent target sites, each target site having from about 6-10 base pairs.

Typically, the zinc finger DNA-binding domain is linked to a regulatory domain, e.g, a transcription factor repressor domain such as the Kruppel-associated box (KRAB), the ERF repressor domain (ERD), or the mSIN3 interaction domain (SID). For repression of gene expression, typically the expression of the gene is reduced by about 20% (i.e., 80% of non-ZFP modulated expression), more preferably by about 50% (i.e., 50% of non-ZFP modulated expression), more preferably by about 75-100% (i.e., 25% to 0% of non-ZFP modulated expression).

A zinc finger protein can be engineered to respond to a small molecule, such that the small molecule can regulate activity of the zinc finger protein. In one embodiment, a cell comprises two zinc finger proteins. The zinc finger proteins can target two different candidate genes. For example, one ZFP can target an SNCA gene to inhibit expression, and a second ZFP can target a gene encoding a component of the proteosome machinery, e.g, to enhance expression. Alternatively, the second ZFP can target and inhibit expression of a second gene that contributes to the alpha-synuclein aggregation phenotype. Alternatively, the zinc finger proteins can target two different target sites on the same candidate gene. Expression of each zinc finger protein can be under small molecule control (e.g., by two different small molecules) to allow for variations in the degree of repression of gene expression.

A "small molecule," as used herein is a chemical compound that can affect the phenotype of a cell or organism by, for example, modulating the activity of a specific protein or nucleic acid, e.g., an SNCA protein or nucleic acid, within a cell. Small molecules may affect a cell by directly interacting with a protein or by interacting with a molecule that acts upstream or downstream of the biochemical cascade that results in protein expression or activity. Typically, a small molecule has a molecular weight of less than about 3000, preferably less than about 2000, more preferably less than about 1000, less than about 900, less than about 800, less than about 700 or less than about 600 Da.

Treatment Methods and Routes of Delivery

The following discussion refers to treatment with an iRNA agent. However, it is to be understood that the invention includes analogous methods and compositions which use or embody other inhibitory agents disclosed herein, e.g., antisense molecules and ribozymes that target SNCA RNA, zinc finger proteins, and antibodies, and synthetic and naturally-occurring polypeptides, or small molecules that, in preferred embodiments, bind to and inhibit the SNCA protein. A composition that includes a composition targeting alpha-synuclein, e.g., a ribozyme, antisense oligonucleotide, iRNA agent, antibody, small molecule, or zinc finger protein, can be delivered to a subject by a variety of routes. Exemplary routes include intrathecal, parenchymal (e.g., in the brain), intravenous, nasal, and ocular delivery. A preferred route of delivery is directly to the brain. The anti-SNCA agents can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, or intrathecal or intraventricular administration.

The route of delivery can be dependent on the disorder of the patient. For example, a subject diagnosed with PD can be administered an anti-SNCA iRNA agent directly to the brain, e.g., directly to the substantia nigra of the brain (e.g., into the striatal dopamine domains within the substantia nigra). A subject diagnosed with multiple system atrophy can be administered an iRNA agent directly into the brain, e.g., into the striatum and substantia nigra regions of the brain, and into the spinal cord. A subject diagnosed with Lewy body dementia can be administered an iRNA agent directly into the brain, e.g., directly into the cortex of the brain, and administration can be diffuse. In addition to an agent which inhibits SNCA expression, e.g., an anti-SNCA iRNA agent, a patient can be administered a second therapy, e.g., a palliative therapy and/or disease-specific therapy. A palliative therapy can be a dopaminergic therapy, for example, such as methyldopa or coenzyme Q10.

In some embodiments, such as for the treatment of Parkinson's Disease, the secondary therapy can be, for example, symptomatic (e.g., for alleviating symptoms), neuroprotective (e.g., for slowing or halting disease progression), or restorative (e.g., for reversing the disease process). Symptomatic therapies include the drugs carbidopa/levodopa, entacapone, tolcapone, pramipexole, ropinerole, pergolide, bromocriptine, selegeline, amantadine, and several anticholingergic agents. Deep brain stimulation surgery as well as stereotactic brain lesioning may also provide symptomatic relief. Neuroprotective therapies include, for example, carbidopa/levodopa, selegeline, vitamin E, amantadine, pramipexole, ropinerole, coenzyme Q10, and GDNF. Restorative therapies can include, for example, surgical transplantation of stem cells.

An anti-SNCA iRNA agent can be delivered to neural cells of the brain. Delivery methods that do not require passage of the composition across the blood-brain barrier can be utilized. For example, a pharmaceutical composition containing an iRNA agent can be delivered to the patient by injection directly into the area containing the alpha-synuclein aggregates. For example, the pharmaceutical composition can be delivered by injection directly into the brain. The injection can be by stereotactic injection into a particular region of the brain (e.g., the substantia nigra, cortex, hippocampus, or globus pallidus). The iRNA agent can be delivered into multiple regions of the central nervous system (e.g., into multiple regions of the brain, and/or into the spinal cord). The iRNA agent can be delivered into diffuse regions of the brain (e.g., diffuse delivery to the cortex of the brain).

In one embodiment, the iRNA agent can be delivered by way of a cannula or other delivery device having one end implanted in a tissue, e.g., the brain, e.g., the substantia nigra, cortex, hippocampus, or globus pallidus of the brain. The cannula can be connected to a reservoir of iRNA agent. The flow or delivery can be mediated by a pump, e.g., an osmotic pump or minipump. In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An iRNA agent can be modified such that it is capable of traversing the blood brain barrier. For example, the iRNA agent can be conjugated to a molecule that enables the agent to traverse the barrier. Such modified iRNA agents can be administered by any desired method, such as by intraventricular or intramuscular injection, or by pulmonary delivery, for example.

The anti-SNCA iRNA agent can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the iRNA agent can also be applied via an ocular patch.

Administration can be provided by the subject or by another person, e.g., a another caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The subject can be monitored for reactions to the treatment, such as edema or hemorrhaging. For example, the patient can be monitored by MRI, such as daily or weekly following injection, and at periodic time intervals following injection.

The subject can also be monitored for an improvement or stabilization of disease symptoms. Such monitoring can be achieved, for example, by serial clinical assessments (e.g., using the United Parkinson's Disease Rating Scale) or functional neuroimaging. Monitoring can also include serial quantitative measures of striatal dopaminergic function (e.g., fluorodopa and positron emission tomography) comparing treated subjects to normative data collected from untreated subjects. Additional outcome measures can include survival and survival free of palliative therapy and nursing home placement. Statistically significant differences in these measurements and outcomes for treated and untreated subjects is evidence of the efficacy of the treatment.

A pharmaceutical composition containing an anti-SNCA iRNA agent can be administered to any patient diagnosed as having or at risk for developing a neurodegenerative disorder, such as a synucleinopathy. In one embodiment, the patient is diagnosed as having a neurodegenerative order, and the patient is otherwise in general good health. For example, the patient is not terminally ill, and the patient is likely to live at least 2, 3, 5, or 10 years or longer following diagnosis. The patient can be treated immediately following diagnosis, or treatment can be delayed until the patient is experiencing more debilitating symptoms, such as motor fluctuations and dyskinesis in PD patients. In another embodiment, the patient has not reached an advanced stage of the disease, e.g., the patient has not reached Hoehn and Yahr stage 5 of PD (Hoehn and Yahr, *Neurology* 17:427-442, 1967). In another embodiment, the patient is not terminally ill. In general, an anti-SNCA iRNA agent can be administered by any suitable method. As used herein, topical delivery can refer to the direct application of an iRNA agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the iRNA agent to the epidermis or dermis of a subject, or to specific strata thereof, or to an underlying tissue.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An anti-SNCA iRNA agent can be administered to a subject by pulmonary delivery. Pulmonary delivery compositions can be delivered by inhalation by the patient of a dispersion so that the composition, preferably iRNA, within the dispersion can reach the lung where it can be readily absorbed through the alveolar region directly into blood circulation. Pulmonary delivery can be effective both for systemic delivery and for localized delivery to treat diseases of the lungs. In one embodiment, an anti-SNCA iRNA agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An anti-SNCA iRNA agent can be administered by an oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an anti-SNCA iRNA agent administered by oral or nasal delivery has been modified to be capable of traversing the blood-brain barrier.

In one embodiment, unit doses or measured doses of a composition that include iRNA are dispensed by an implanted device. The device can include a sensor that monitors a parameter within a subject. For example, the device can include a pump, such as an osmotic pump and, optionally, associated electronics.

An iRNA agent can be packaged in a viral natural capsid or in a chemically or enzymatically produced artificial capsid or structure derived therefrom.

Dosage. An anti-SCNA iRNA agent can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an iRNA agent directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder, e.g., a disease or disorder associated with synucleinopathies.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has PD and the modality is a therapeutic agent other than an iRNA agent, e.g., other than a double-stranded iRNA agent, or sRNA agent. The therapeutic modality can be, for example, levadopa or depronil.

In one embodiment, a subject is administered an initial dose, and one or more maintenance doses of an iRNA agent, e.g., a double-stranded iRNA agent, or sRNA agent, (e.g., a precursor, e.g., a larger iRNA agent which can be processed into an sRNA agent, or a DNA which encodes an iRNA agent, e.g., a double-stranded iRNA agent, or sRNA agent, or precursor thereof). The maintenance dose or doses are generally lower than the initial dose, e.g., one-half less of the initial dose. A maintenance regimen can include treating the subject with a dose or doses ranging from 0.01 μg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. In another embodiment, the iRNA agent species has sequences that are non-overlapping and non-adjacent to another species with respect to a naturally occurring target sequence. In another embodiment, the plurality of iRNA agent species is specific for different naturally occurring target genes. In another embodiment, the iRNA agent is allele specific.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or sRNA agent (e.g., a precursor, e.g., a larger iRNA agent which can be processed into a sRNA agent, or a DNA which encodes an iRNA agent, e.g., a double-stranded iRNA agent, or sRNA agent, or precursor thereof) can include a single treatment or, preferably, can include a series of treatments. It will also be appreciated that the effective dosage of an iRNA agent such as an sRNA agent used for treatment may increase or decrease over the course of a particular treatment. Changes in dosage may result and become apparent from the results of diagnostic assays as described herein. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an SNCA RNA. The transgenic animal can be deficient for the corresponding endogenous RNA. In another embodiment, the composition for testing includes an iRNA agent that is complementary, at least in an internal region, to a sequence that is conserved between the target RNA in the animal model and the target RNA in a human.

Kits. In certain other aspects, the invention provides kits that include a suitable container containing a pharmaceutical formulation of an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an iRNA agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The invention is further illustrated by the following examples, which should not be construed as further limiting.

EXAMPLES

Example 1

Design of iRNA Agents Targeting SNCA

Double stranded RNAs having the sequences described in Table 1 were synthesized. FIG. 1A shows the sequence of the full-length SNCA mRNA, and the target sites of the dsRNAs SNCA1-9 (Table 1).

The sequences of SNCA6, 7, 8, and 9 were designed using the dsRNA Selection Tool developed at the Whitehead Institute (Cambridge, Mass.) and available free on-line. By using the dsRNA Selection Tool, all possible siRNAs having a GC content between 30 and 70% were selected, except (a) any sequences containing runs of four or more A, T or G residues, and (b) any sequences with more than seven consecutive GC pairs in a row. A total of 237 candidate siRNAs matched this criteria. The 237 candidate siRNAs were then screened against the human UniGene database (Pontius et al., UniGene: a unified view of the transcriptome. In: The NCBI Handbook. Bethesda (Md.): National Center for Biotechnology Information; 2003) to identify those siRNAs having a sequence that only matched human alpha-synuclein. The screening was performed using BLAST search technology (Altschul et al., *Nucleic Acids Res.* 25:3389-3402, 1997). The identified subset of siRNAs was screened against mouse UniGene using BLAST to identify those siRNAs having a sequence that only matches the alpha-synuclein gene in mouse. Thirteen sequences were identified, and four non-overlapping duplexes (SNCA6, 7, 8, and 9) were selected for use in the assays described below.

TABLE 1 dsRNA sequences

| dsRNA[a] | SEQ ID NO | Strand | Sequence[b] |
|---|---|---|---|
| SNCA1 | 3 | Sense | 5'-GGUGUGGCAACAGUGGCUGAG-3' |
|  | 4 | Antisense | 3'-UACCACACCGUUGUCACCGACUC-5' |
| SNCA2 | 5 | Sense | 5'-AACAGUGGCUGAGAAGACCAA-3' |
|  | 6 | Antisense | 3'-CGUUGUCACCGACUCUUCUGGUU-5' |
| SNCA3 | 7 | Sense | 5'-AUUGCAGCAGCCACUGGCUUU-3' |
|  | 8 | Antisense | 3'-CGUAACGUCGUCGGUGACCGAAA-5' |
| SNCA4 | 9 | Sense | 5'-AAGUGACAAAUGUUGGAGGAG-3' |
|  | 10 | Antisense | 3'-CGUUCACUGUUUACAACCUCCAC-5' |
| SNCA5 | 11 | Sense | 5'-GAAGAAGGAGCCCCACAGGAA-3' |
|  | 12 | Antisense | 3'-UACUUCUUCCUCGGGGUGUCCUU-5' |
| SNCA6 | 13 | Sense | 5'-CGGGUGUGACAGCAGUAGCdTdT-3' |
|  | 14 | Antisense | 3'-dTdTGCCCACACUGUCGUCAUCG-5' |
| SNCA7 | 15 | Sense | 5'-UCCUGACAAUGAGGCUUAUdTdT-3' |
|  | 16 | Antisense | 3'-dTdTAGGACUGUUACUCCGAAUA-5' |
| SNCA7s | 17 | Sense | 5'-U*CCUGACAAUGAGGCUUAUdT*dT-3' |
|  | 18 | Antisense | 3'-dT*dTAGGACUGUUACUCCGAAU*A-5' |
| SNCA8 | 19 | Sense | 5'-CUACGAACCUGAAGCCUAAdTdT-3' |
|  | 20 | Antisense | 3'-dTdTGAUGCUUGGACUUCGGAUU-5' |
| SNCA 8s1 | 21 | Sense | 5'-C*UACGAACCUGAAGCCUAAdT*dT-3' |
|  | 22 | Antisense | 3'-dT*dTGAUGCUUGGACUUCGGAU*U-5' |
| SNCA 8s2 | 23 | Sense | 5'-C*UACGAACCUGAAGCCUAAdT*dT-3' |
|  | 24 | Antisense | 3'-dT*dTGAUGCUUGGACUUCGGAU*U-5' |
| SNCA9 | 25 | Sense | 5'-CUAUUGUAGAGUGGUCUAUdTdT-3' |
|  | 26 | Antisense | 3'-dTdTGAUAACAUCUCACCAGAUA-5' |
| ALN-DP-3000 | 27 | Sense | 5'-GAACUGUGUGUGAGAGGUCCU-3'-F |
|  | 28 | Antisense | 3'-C*C*CUUGACACACACUCUCCAGGA-5' |
| siRNA Mr | 29 | Sense | 5'-GACGUAAACGGCCACAAGUUC-3' |
|  | 30 | Antisense | 3'-CGCUGCAUUUGCCGGUGUUCA-5' |
| SNCA 8s2m | 50 | Sense | 5'-C*UAUGAGCCUGAAGCCUAAdT*dT-3' |
|  | 51 | Antisense | 3'-dT*dTGAUACUCGGACUUCGGAU*U-5' |

[a]SNCA name designations are equivalent to Mayo designations (e.g., SNCA 1 is equivalent to Mayo1);
[b]nucleotides marked with * carry a phosphorothioate modification; underlined nucleotides carry a 2'-O-Me modification; "F" indicates a fluorescein conjugate Example 2

SNCA dsRNAs Decreased Protein Expression In vitro

Neuroblastoma cells (BE(2)-M17) were co-transfected with 50 nM dsRNA and a plasmid expressing either EGFP or an α-synuclein-EGFP (EGFP/NACP) fusion protein (as used herein NACP is synonymous with the gene product of SNCA). Expression of the EGFP and EGFP/NACP fusion proteins was assayed by Western blot analysis (FIG. 2).

The in vitro cell-based assay monitors the ability of the test dsRNAs of Table 1 to downregulate expression of an SNCA RNA. The SNCA target RNA in these experiments is fused to an EGFP RNA. Antibodies against EGFP facilitate the detection of an EGFP/NACP fusion protein translated from the RNA.

Control experiments used in this assay included the use of a dsRNA targeting a luciferase RNA (see the lanes marked "siRNA Mr" in FIG. 2), and cells not transfected with siRNA. Antibodies against alpha tubulin were used as controls to monitor the amount of total protein loaded in each lane. The control experiments indicated that EGFP and the EGFP/NACP proteins are expressed in about equal amounts when in the absence of anti-SNCA dsRNA. The strongest down-regulatory effect of EGFP/NACP expression was observed with Mayo2, Mayo7, and Mayo8 dsRNAs (as used herein, MayoX siRNAs are synonymous with SNCAX dsRNAs). A weaker effect was observed with Mayo1, Mayo6, and Mayo9 dsRNAs. siRNA Mr affected expression of both the vector derived EGFP and the EGFP/NACP conjugate, demonstrating the suitability of the assay.

Figure 3:
FIG. 3 is a Western blot detecting EGFP/NACP fusion proteins expressed in BE(2)-M17 human neuroblastoma cells. The cells were cotransfected with a vector expressing an EGFP/NACP fusion protein and varying nM concentrations of Mayo2, Mayo7, or Mayo8 siRNA. These siRNAs are equivalent to siRNAs SNCA2, SNCA7, and SNCA8, of Table 1 respectively. The Western blots were stripped of the anti-GFP antibody, and reprobed with anti-tubulin antibody to monitor equivalent loading of protein between samples.

The inhibitory effect of the most effective dsRNAs (Mayo2, Mayo7, and Mayo8) was examined at varying dsRNA concentrations during a 24 h incubation (FIG. 3). The $IC_{50}$ value was determined to be less than 1 nM.

Figure 4:
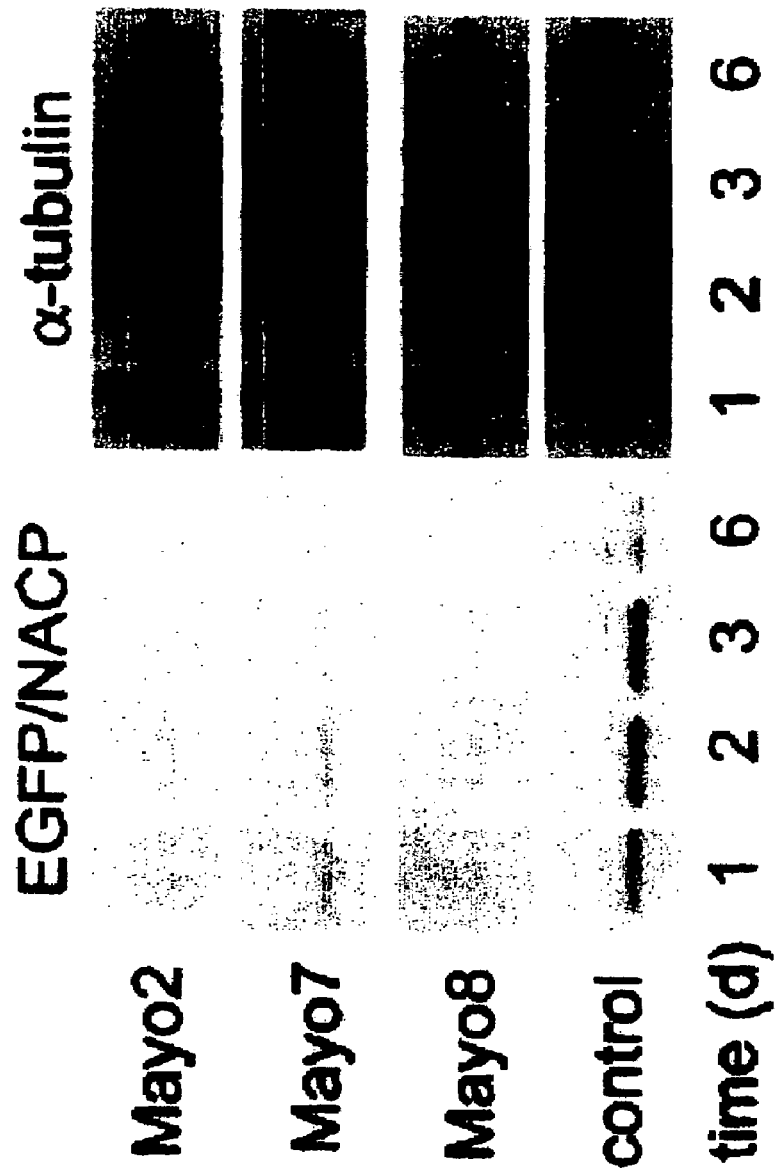
FIG. 4 is a Western blot detecting EGFP/NACP fusion expressed in BE(2)-M17 human neuroblastoma cells. The cells were cotransfected with a vector expressing an EGFP/NACP fusion protein and 50 nM Mayo2, Mayo7, or Mayo8 siRNA. These siRNAs are equivalent to siRNAs SNCA2, SNCA7, and SNCA8 of Table 1, respectively. In the "control" experiment, no siRNA was transfected with the fusion construct. Protein expression was monitored over the course of six days. The Western blots were stripped of the anti-GFP antibody, and reprobed with anti-tubulin antibody to monitor equivalent loading of protein between samples. The cells were non-dividing.
Figure 5:
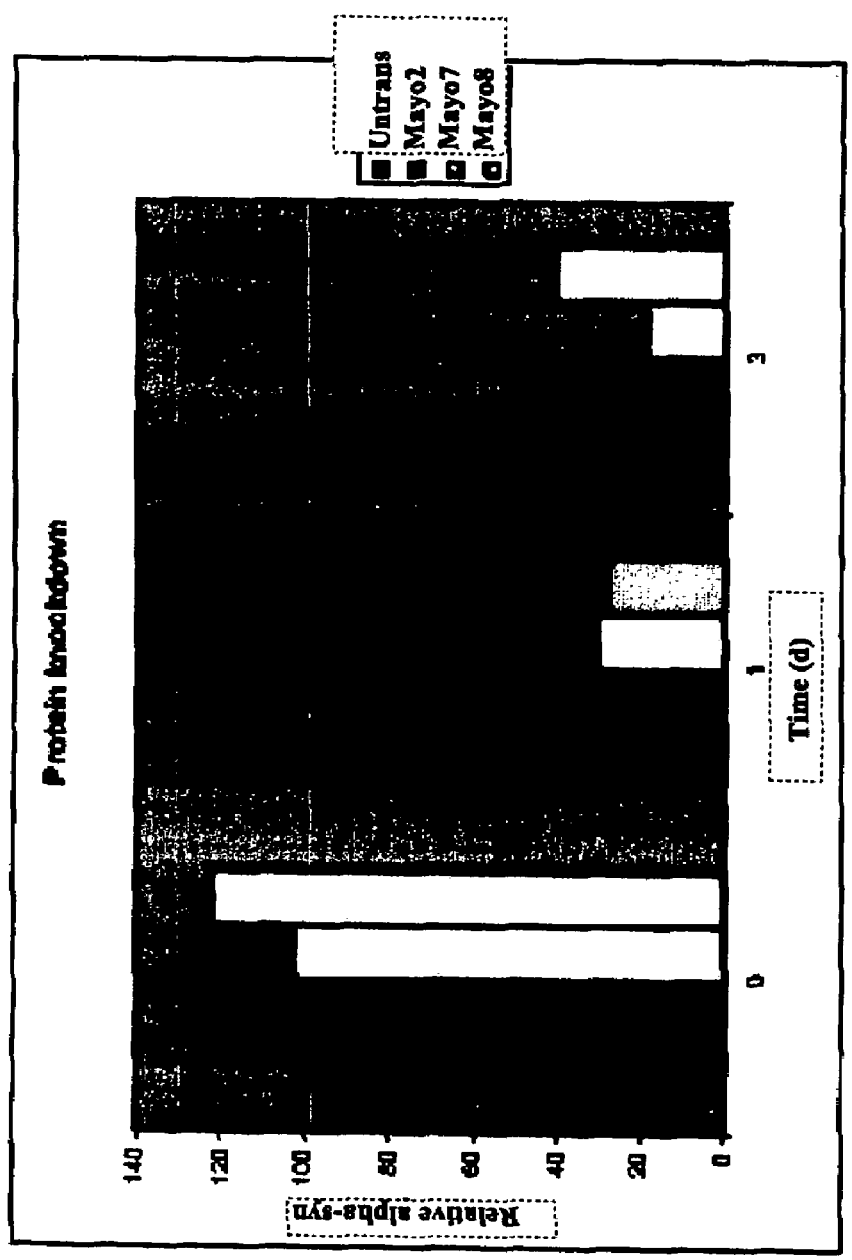
FIG. 5 is a graph depicting relative alpha-synuclein levels assayed by Western blot analysis. Neuroblastoma cells were transfected with Mayo2, Mayo7, or Mayo8 siRNA. Endogenous alpha synuclein protein expression was monitored over the course of three days. In the "untransfected" experiment, no siRNA was transfected, and protein levels in these samples were set as 100% normal expression.
Figure 6:
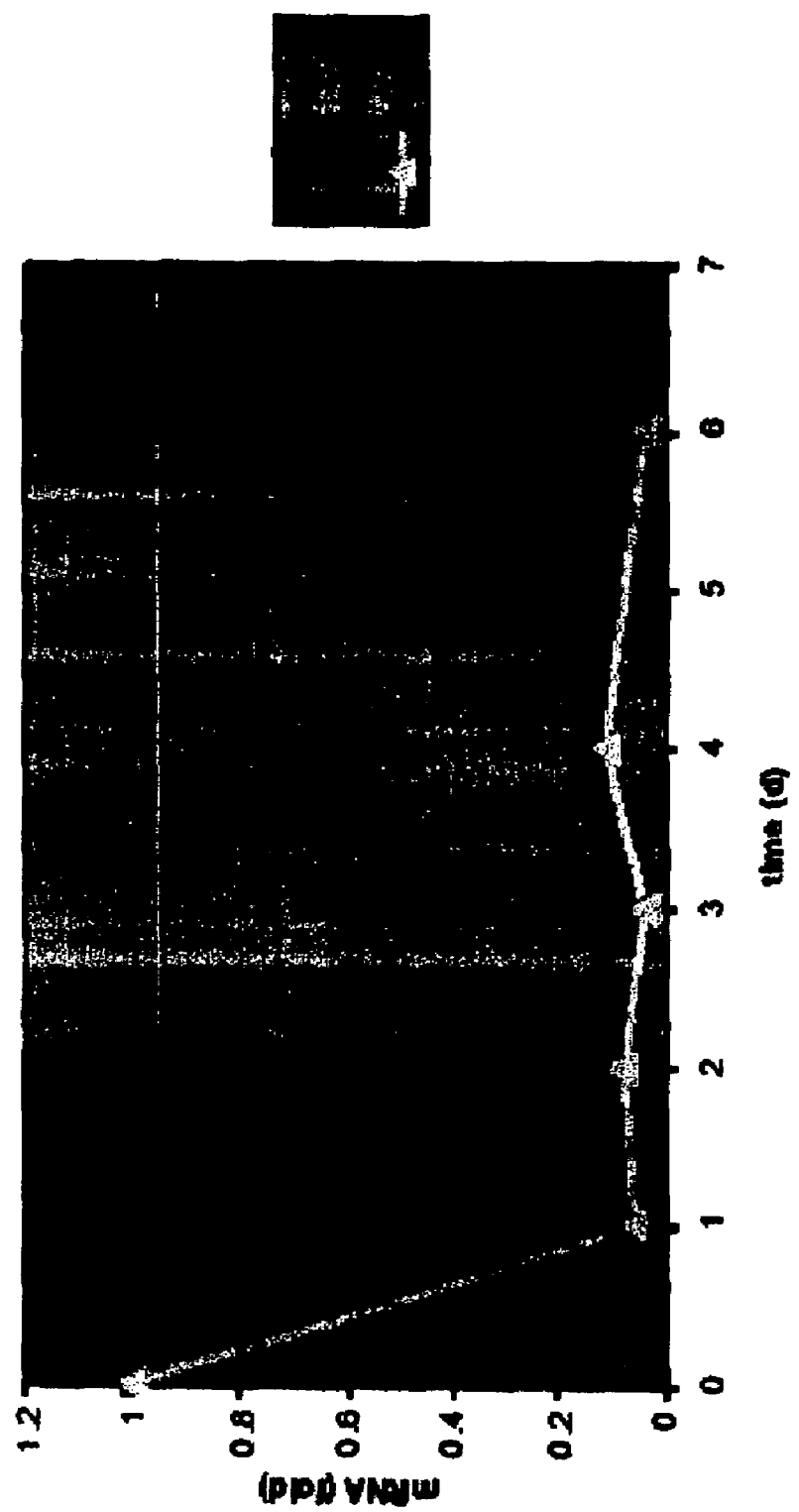
FIG. 6 is a graph depicting the effect of Mayo2, 7, and 8 siRNAs on levels of endogenous alpha-synuclein RNA.

The inhibitory effect of the most effective siRNAs was tested in slowly-dividing neuroblastoma cells in cultures with low levels of serum. BE(2)-M17 cells were transfected with a plasmid expressing the EGFP/NACP fusion protein alone (control) or cotransfected with the dsRNAs Mayo2, Mayo7, or Mayo8. Expression of the EGFP/NACP protein was monitored over a period of six days. Fusion protein expression was observed to be effectively silenced for at least three days (FIG. 4). The dsRNAs also inhibited endogenous protein expression in similar cells for at least three days (FIG. 5). The Mayo2, Mayo7, and Mayo8 siRNAs also inhibited expression of endogenous alpha synuclein RNA in slowly dividing cells (FIG. 6). After 6 days, Mayo2 and Mayo8 continued to effectively inhibit endogenous SNCA expression. Levels of alpha synuclein mRNA in the cells were measured by the Taqman® method of quantitative RT-PCR normalized against 18S rRNA expression levels. Mayo9, which targets the 3'UTR of SNCA, did not inhibit expression of endogenous alpha synuclein RNA.

Figure 7:
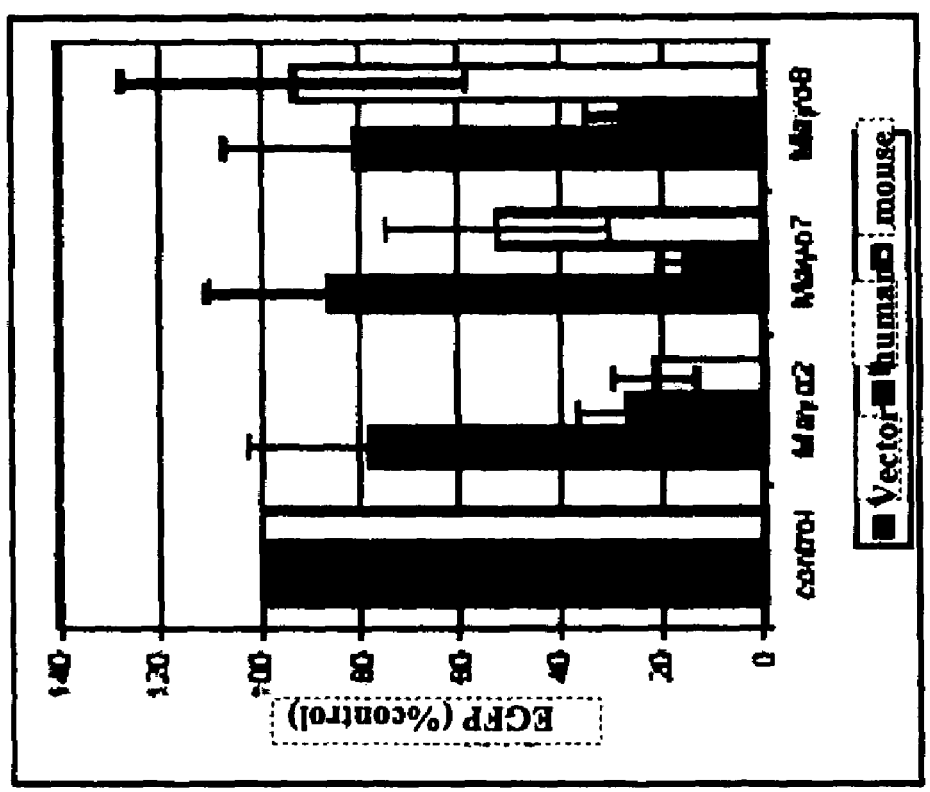
FIG. 7 is a graph depicting the activity of the siRNAs on human and mouse alpha-synuclein/EGFP conjugate expression. BE(2)-M17 human neuroblastoma cells were cotransfected with a plasmid encoding EGFP (vector) or EGFP conjugated to either human or mouse alpha-synuclein and Mayo2, Mayo7 or Mayo8. Expression was equalized using tubulin immunoreactivity and measured as a proportion of the expression of the plasmid-only EGFP immunoreactivity (control).

The efficacy of the Mayo2, 7, and 8 dsRNAs were tested against mouse SNCA. Cells were cotransfected with the dsRNAs and a plasmid encoding EGFP alone (vector) or EGFP-NACP of human or mouse origin. Expression of EGFP and EGFP-NACP was assayed by Western blot. While all three dsRNAs inhibited expression of human EGFP-NACP, only Mayo2 inhibited expression in mouse EGFP-NACP (FIG. 7). The human and mouse mRNA sequence is identical at the Mayo2 locus, but diverges by two nucleotides at each of the Mayo7 and Mayo8 loci.

Figure 11:
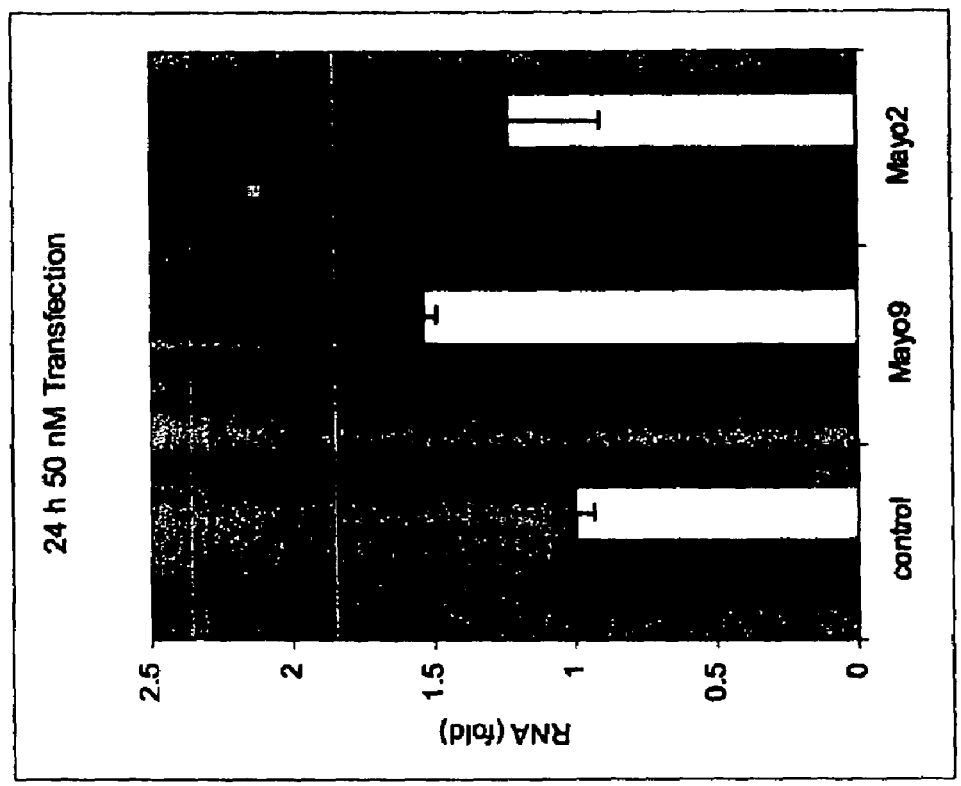
FIG. 11 is a graph demonstrating the gene specificity of Mayo2.

SNCB (beta-synuclein) shares sequence similarity with alpha-synuclein at the Mayo2 locus, but differs in sequence by four nucleotides. The efficacy of the Mayo2 was tested against SNCB. BE(2)-M17 cells were transfected with a plasmid expressing the dsRNAs Mayo2 or Mayo9. Expression of endogenous SNCA and SNCB RNA was assayed by Taqman® method quantitative RT-PCR. Mayo2 inhibited expression of SNCA but not expression of SNCB (FIG. 11). As was expected, Mayo9 did not inhibit expression of SNCB or SNCA.

Example 3

Stability of SNCA siRNAs

The stability of the sense and antisense strands of the SNCA siRNAs was examined in 90% mouse serum or 90% human serum, and in mouse brain tissue. To perform the stability assays, siRNA was radioactively labeled on the sense or antisense strand (both strands were assayed for stability in the serum and brain tissue). Protein extracts were prepared from mouse brain, and 100 nM siRNA duplex was incubated with the extract at 37° C. At time points over the course of 4-5 hours, sample was removed and analyzed on a polyacrylamide denaturing gel.

The stability of Mayo2, 7, and 8 was tested in mouse serum and brain extract. Further, the cleavage sites of Mayo7 and Mayo8 were mapped by T1 analysis (FIGS. 8A and 8B). RNAse T1 cleaves 3' of G nucleotides, and T1 digestion of an RNA that has a known sequence provides orientation and a basis for comparison to detect non-RNAse T1 cleavage sites. T1 was used to map the cleavage sites of Mayo7 (also called SNCA7, or AL-DUP-1477) and Mayo8 (also called SNCA8, or AL-DUP-1478) siRNAs (FIGS. 8A and 8B, respectively, and Table 1). Mayo7 and 8 were 5' end labeled with $^{32}$P on the sense strand, and RNAse T1 digestion was performed for four hours. The samples were analyzed by electrophoresis. Mayo7 was found to be susceptible to endonucleolytic cleavage 3' of U16 and U17. Mayo8 was found to be susceptible to endonucleolytic cleavage 3' of U16.

Figure 9B:
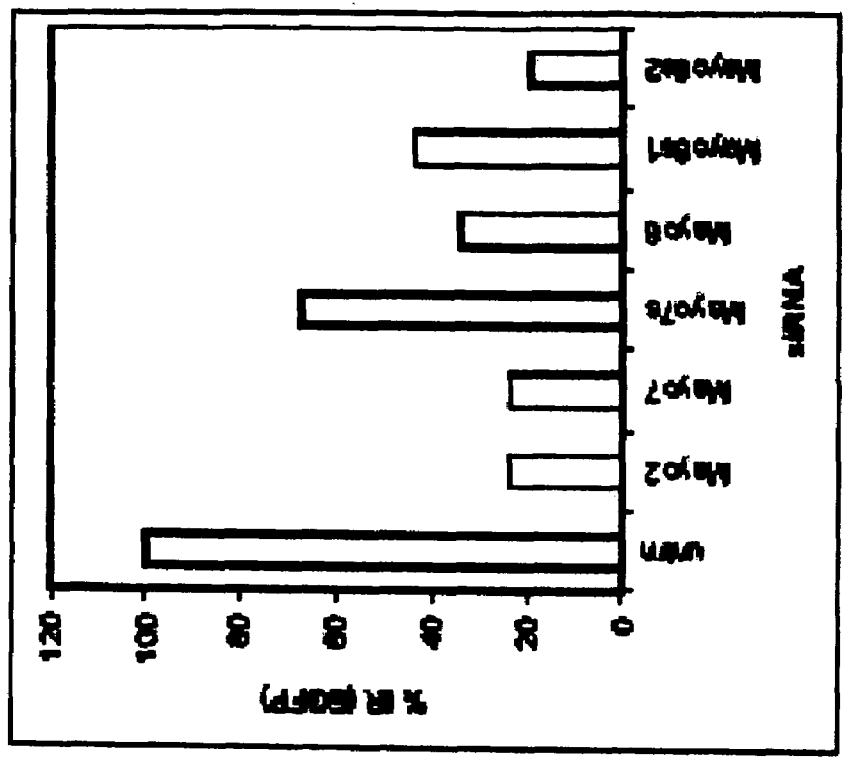
FIG. 9B is a graph depicting the effect of the dsRNAs of FIG. 9A on EGFP/alpha-synuclein protein expression. The y-axis represents percent EGFP immunoreactivity (IR) compared to the control untransfected experiment (untrn).
Figure 9A:
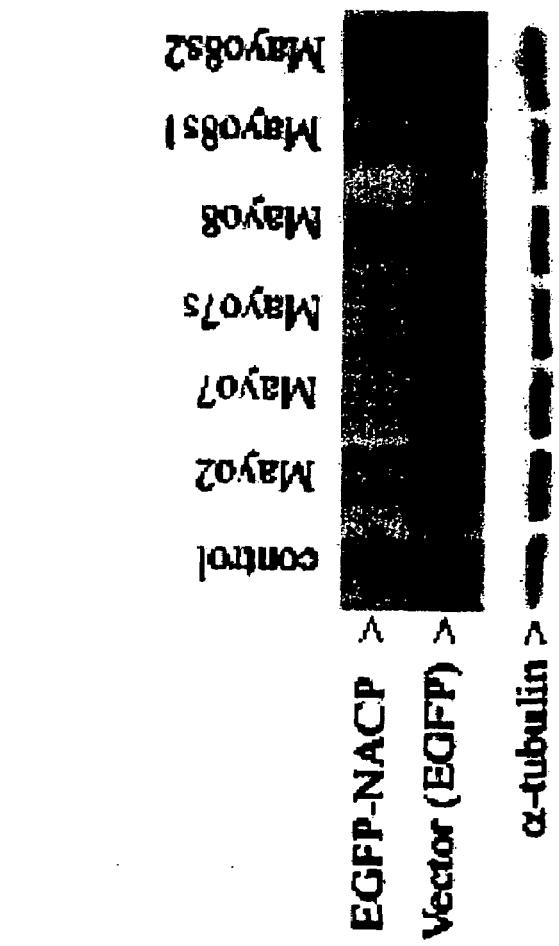
FIG. 9A is a Western blot of EGFP or EGFP/NACP fusion proteins expressed in a neuroblastoma cell line. The cells were cotransfected with either a plasmid expressing EGFP, or a plasmid expressing EGFP/NACP fusion protein, and an siRNA listed in Table 1. In the figure, siRNAs Mayo2, Mayo7, Mayo7s, Mayo8, Mayo8s1, and Mayo8s2 are equivalent to the siRNAs of Table 1 (SNCA2, SNCA7, SNCA7s, SNCA8, SNCA8s1, and SNCA8s2, respectively). In the control experiment, siRNA was not transfected into cells with the EGFP and EGFP-NACP vectors. The Western blots were stripped of the anti-GFP antibody, and reprobed with anti-tubulin antibody to monitor equivalent loading of protein between samples.

To increase stability of the Mayo7 and Mayo8 siRNAs, nucleotides were modified with a 2'-O-Me group or a phosphorothioate linkage to create Mayo7s, Mayo8s1, and Mayo8s2 (Table 1). The modified siRNAs (50 nM) were cotransfected with an EGFP-NACP vector into cells as described above. Untransfected cells served as a control. Gene expression was monitored by Western blot analysis. Each of the three modified siRNAs inhibited expression of the EGFP-NACP construct (FIGS. 9A and 9B).

The modified and unmodified Mayo8 siRNAs were analyzed by Stains-All (cat. #E9379, Sigma, St. Louis, Mo.), which was performed as follows. All solutions were prepared in nuclease-free water (cat. #9930, Ambion, Austin, Tex.), using nuclease-free reagents. A 50 µM stock of dsRNA for use in the stability assays was prepared by mixing 50 µM sense strand RNA and 50 µM antisense strand in 1×PBS. This mixture was incubated at 90° C. for 2 minutes to denature the nucleic acids, then 37° C. for one hour for annealing.

To perform the stability assay, human serum from clotted male whole blood type AB (cat. #H1513, Sigma, St. Louis, Mo.) was used. Serum was thawed on ice, and mixed with dsRNA to a final concentration of about 4.5 µM (i.e., about 4.2 µg, or about 300 pmoles dsRNA). At time point "0," one control sample was frozen on dry ice immediately following addition of dsRNA to serum, and the sample was stored at −80° C. For other time points (15, 30, 60, 120, and 240 minutes in human serum), the samples were incubated at 37° C. in a Thermomixer (Eppendorf, Hamburg, Germany). At each endpoint, the samples were frozen on dry-ice and stored at −80° C.

To extract the RNA from the serum, samples were thawed on ice, and then 0.5 M NaCl (nuclease free; cat#9760, Ambion, Austin, Tex.) was added to the sample to yield a final concentration of about 0.45 M NaCl. The sample was vortexed briefly (about 5 seconds), and then transferred to a prepared and chilled Phase Lock-Gel-Eppis (Eppendorf, Hamburg, Germany). Five hundred microliters phenol:chloroform:isoamyl alcohol (25:24:1) and 300 µL chloroform were added to the mix. The sample was vortexed briefly for 30 seconds, then centrifuged at 13,200 rpm for 15 minutes at 4° C.

The aqueous phase was transferred to a clean eppendorf tube, and 3M NaOAc, pH 5.2, was added to a final concentration of about 0.1M NaOAc. The solution was vortexed for about 20 seconds and then 1 µL of Glyco Blue (Ambion, Austin, Tex.) was added. The solution was vortexed briefly and gently, then 1 mL ice-cold 100% ethanol was added. The solution was vortexed for about 20 seconds, then stored at −80° C. for one hour, or at −20° C. overnight to precipitate the RNA. Following precipitation, the mixture was centrifuged at 13,200 rpm for 30 min. at 4° C., and the RNA pellet was washed with 500 µL 70% ethanol. The pellet was air-dried, then 30 µL of gel loading buffer (95% formamide, 50 mM EDTA, Xylenecyanol, bromophenol blue) was added to the mix, and the mix vortexed for 2 minutes to resuspend.

The RNA sample was analyzed on a 20 cm×20 cm×0.8 mm (length×width×thickness) 20% polyacrylamide gel. To make the gel, 24 g 8 M Urea, 25 mL 40% (19:1) Acrylamide, and 8 mL formamide was mixed in 1×TBE in a 50 mL solution. Polymerization was activated by 50 uL Temed and 200 uL 10% APS (ammonium persulfate). The gel was run in 1×TBE. The gel was pre-run for 30 minutes at 40 mA. The samples were heated at 100° C. for 5 min. and then immediately chilled on ice. For control experiments, 2 µL of dsRNA was mixed with 8 µL of gel loading buffer. The samples were centrifuged at 13,200 rpm (20 seconds, 4° C.) and 10 µL was loaded onto the gel. The gel was run for about one hour at 40 mA.

To visualize the RNA, the gel was stained with Stains-All solution (cat. #E9379, Sigma, St. Louis, Mo.) (100 mg Stains-All dissolved in 800 mL formamide:water (1:1 v/v)) for 30 minutes. The gel was destained in water for 30-60 minutes as needed. The gel was them imaged on a scanner and analyzed.

Figure 10C:
FIG. 10C is a polyacrylamide gel demonstrating the stability of SNCA8 siRNA (see Table 1). The RNA in the gel is detected with Stains-All (Sigma, St. Louis, Mo.). Lane 1 is SNCA8s2 siRNA duplex. Lane 2 is SNCA8s2 siRNA in PBS control at 0 hour time point. Lane 3 is SNCA8s2 siRNA in PBS control at 24 hour time point. Lane 4 is SNCA8s2 siRNA in human serum at 0 hour time point. Lane 5 is SNCA8s2 siRNA in human serum following incubation for 30 minutes. Lane 6 is SNCA8s2 siRNA in human serum following incubation for 4 hours. Lane 7 is SNCA8s2 siRNA in human serum following incubation for 24 hours.
Figure 10B:
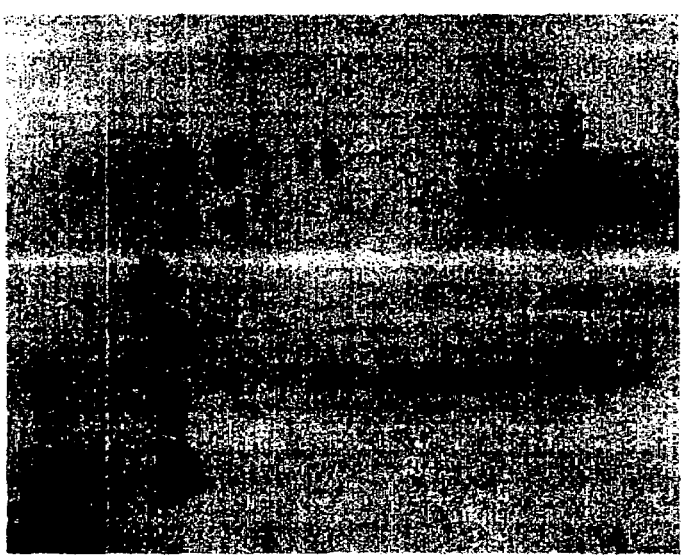
FIG. 10B is a polyacrylamide gel demonstrating the stability of SNCA8 siRNA (see Table 1). The RNA in the gel is detected with Stains-All (Sigma, St. Louis, Mo.). Lane 1 is SNCA8s1 siRNA duplex. Lane 2 is SNCA8s1 siRNA in PBS control at 0 hour time point. Lane 3 is SNCA8s1 siRNA in PBS control at 24 hour time point. Lane 4 is SNCA8s1 siRNA in human serum at 0 hour time point. Lane 5 is SNCA8s1 siRNA in human serum following incubation for 30 minutes. Lane 6 is SNCA8s1 siRNA in human serum following incubation for 4 hours. Lane 7 is SNCA8s1 siRNA in human serum following incubation for 24 hours.
Figure 10A:
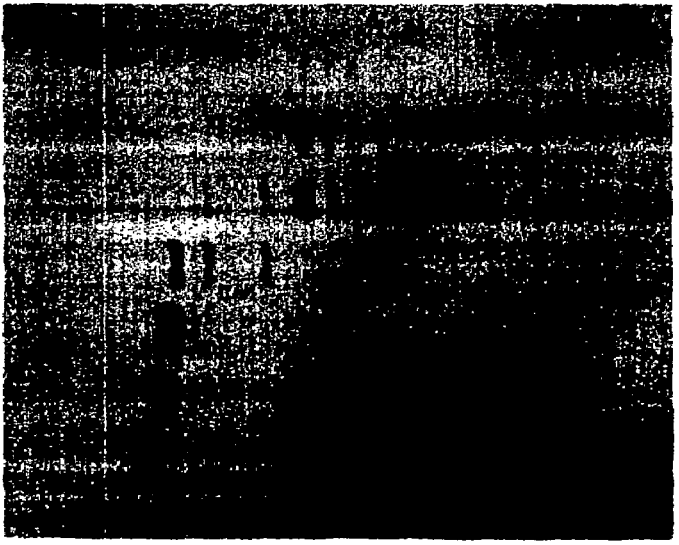
FIG. 10A is a polyacrylamide gel demonstrating the stability of SNCA8 siRNA (see Table 1). The RNA in the gel is detected with Stains-All (Sigma, St. Louis, Mo.). Lane 1 is SNCA8 siRNA duplex. Lane 2 is SNCA8 siRNA in PBS control at 0 hour time point. Lane 3 is SNCA8 siRNA in PBS control at 24 hour time point. Lane 4 is SNCA8 siRNA in human serum at 0 hour time point. Lane 5 is SNCA8 siRNA in human serum following incubation for 30 minutes. Lane 6 is SNCA8 siRNA in human serum following incubation for 4 hours. Lane 7 is SNCA8 siRNA in human serum following incubation for 24 hours.

The results of the stability assay are shown in FIGS. 10A, 10B and 10C. Comparison indicates that the unmodified SNCA8 dsRNA is rapidly degraded, the partially modified dsRNA (SNCA8s1) is partially stabilized, and the further modified SNCA8s2) is the most stable of the three duplexes.

Example 4

In vivo Analysis of siRNA Biodistribution

To determine whether siRNA could be delivered into neural cells in vivo, siRNA targeting luciferase (ALN-DP-3000) (Table 1) was conjugated with a fluorescein label and administered to distinct areas of mouse brain by stereotactic injection (Table 2). ALN-DP-3000 was injected into the cortex, the hippocampus, and the globus pallidus areas of the brain. At different time points post-injection, brain tissue was harvested, sectioned, and examined microscopically for the localization of the fluorescently-labeled siRNA. In all brain regions examined (cortex, hippocampus, and globus pallidus), and at all time points post-injection, siRNA was found to localize to extracellular spaces as well as intracellularly.

TABLE 2

Analysis of ALN-DP-3000 biodistribution in brain tissue

| Injection Site | Stereotactic coordinates | | Time post-injection of tissue analysis |
|---|---|---|---|
| Cortex | AP | −0.0 | 1 hr. |
| | L | −3.5 | |
| | DV | −1.8 | |
| Cortex | AP | −0.0 | 24 hr. |
| | L | −3.5 | |
| | DV | −1.8 | |
| Hippocampus | AP | −1.8 | 1 hr. |
| | L | −2.2 | |
| | DV | −1.2 | |

TABLE 2-continued

Analysis of ALN-DP-3000 biodistribution in brain tissue

| Injection Site | Stereotactic coordinates | | Time post-injection of tissue analysis |
|---|---|---|---|
| Hippocampus | AP | −1.8 | 24 hr. |
| | L | −2.2 | |
| | DV | −1.2 | |
| Globus Pallidus | AP | −0.3 | 1 hr. |
| | L | −1.8 | |
| | DV | −3.5 | |
| Globus Pallidus | AP | −0.3 | 2 hr. |
| | L | −1.8 | |
| | DV | −3.5 | |
| Globus Pallidus | AP | −0.3 | 4 hr. |
| | L | −1.8 | |
| | DV | −3.5 | |

To assess activity in vivo, siRNA duplexes were administered by stereotactic injection to the substantia nigra of wild-type mice (C57BL/6 mice; Taconic, Germantown, N.Y.). Coordinates for stereotactic injection were as follows: AP −3.4 mm; L −1.5 mm; DV −3.8 mm. Three animals each received two microliters of a 200 µM solution of Mayo-8s2m siRNA in phosphate buffered saline (PBS) (Table 1; FIG. 12A, bars labeled "E"). As a control, three animals were injected with PBS (FIG. 12B, bars labeled "C"). Twenty-four hours after injection, animals were sacrificed and brains were removed. Tissue blocks encompassing the injection track were dissected and total RNA was isolated from about 100 mg of tissue using Trizol reagent (Invitrogen, Carlsbad, Calif.). Taqman® quantitative RT-PCR (Applied Biosystems, Foster City, Calif.) was used to measure relative levels of alpha-synuclein mRNA. As a normalization standard, 18S rRNA was measured separately ("individual tube") or in the same Taqman® reaction with alpha-synuclein ("duplex"). Reverse transcription was performed at 48° C. for 30 minutes, and PCR was performed for 40 cycles of (95° C. for 15 sec., 65° C. for 1 min.). Each experiment was performed three times, and in each experiment, reactions were performed in quadruplicate. The comparative count method (ΔΔCt) was used to determine relative levels of alpha synuclein compared to control (Heid et al., *Genome Res.* 6:986-994, 1996). SDS 2.1 software (Applied Biosystems, Foster City, Calif.) was applied with automatic threshold values and automatic outlier removal.

The preliminary results shown in FIGS. 12A and 12B indicated that, on average, the Mayo-8s2m siRNA specifically decreased SNCA mRNA levels in mouse brain, as relative levels of the control 18S rRNA were not affected.

Example 5

Silencing of Endogenous Alpha-synuclein by Intraparenchymal Infusion of siRNA

Methods

Using stereotactic surgery, infusion cannulae were implanted into the hippocampus of eight-week old, female B6 mice (coordinates from bregma: x=(−)2.0, y=(−)1.5, z=2.0 calculated from Paxinos and Franklin, The Mouse Brain in Stereotaxic Coordinates). Cannulae were implanted into the right hemisphere of the brain. The cannulae were connected via catheters to osmotic mini-pumps (Alzet model 1002) containing approximately one hundred microliters of 2.1 mM siRNA solution in Phosphate Buffered Saline (PBS). The pumps were implanted subcutaneously. The infusion rate of 0.25 microliters per hour resulted in a dose of approximately 180 micrograms of siRNA per day. Infusion continued for a period of fifteen days. Treatment groups were: PBS (n=10), alpha-synuclein duplex (SNCA siRNA; n=8), cholesterol conjugated alpha-synuclein duplex (SNCA siRNA-chol; n=8), luciferase control duplex (n=8), cholesterol conjugated luciferase control duplex (n=10). The sequences of the duplexes, as well as chemical modifications are shown below in Table 3.

TABLE 3

| siRNA | | Sequence |
|---|---|---|
| Luc control | S | 5' cuuAcGcuGAGuAcuucGATsT 3' (SEQ ID NO: 52) |
| | AS | 5' UCGAAGuACUcAGCGuAAGTsT 3' (SEQ ID NO: 53) |
| Luc control | S | 5' cuuAcGcuGAGuAcuucGATsTs-chol 3' (SEQ ID NO: 54) |
| chol | AS | 5' UCGAAGuACUcAGCGuAAGTsT 3' (SEQ ID NO: 53) |
| SNCA | S | 5' CsuAUGAGCCUGAAGCcuaATsT 3' (SEQ ID NO: 55) |
| | AS | 5' usuAGGCUUCAGGCUCAuAGTsT 3' (SEQ ID NO: 56) |
| SNCA chol | S | 5' CsuAUGAGCCUGAAGCcuaATsT-chol 3' (SEQ ID NO: 57) |
| | AS | 5' usuAGGCUUCAGGCUCAuAGTsT 3' (SEQ ID NO: 56) |

Key
A, C, G, U-ribonucleotides
c, u-2'-OMe nucleotides
s-phosphorothioate linkage
T-thymidine Following the infusion period, brains were collected and the regions corresponding to the hippocampus were dissected from each hemisphere. Total RNA was isolated and used to prepare cDNA by random hexamer priming. Relative levels of alpha-synuclein were measured by TaqMan® quantitative PCR using gene expression MGB probes (SNCA Mm0044733_m1, GAPDH Mm99999915_g1, HPRT Mm00446968_m1, Tau Mm00521988_m1; Applied Biosystems). For more accurate normalization among tissues, levels of GAPDH, HPRT and tau were measured and used to determine a normalization factor. Relative levels of alpha-synuclein were calculated for the right and left hemispheres from each animal, and group means and standard deviations were calculated.

Results

Figure 13:
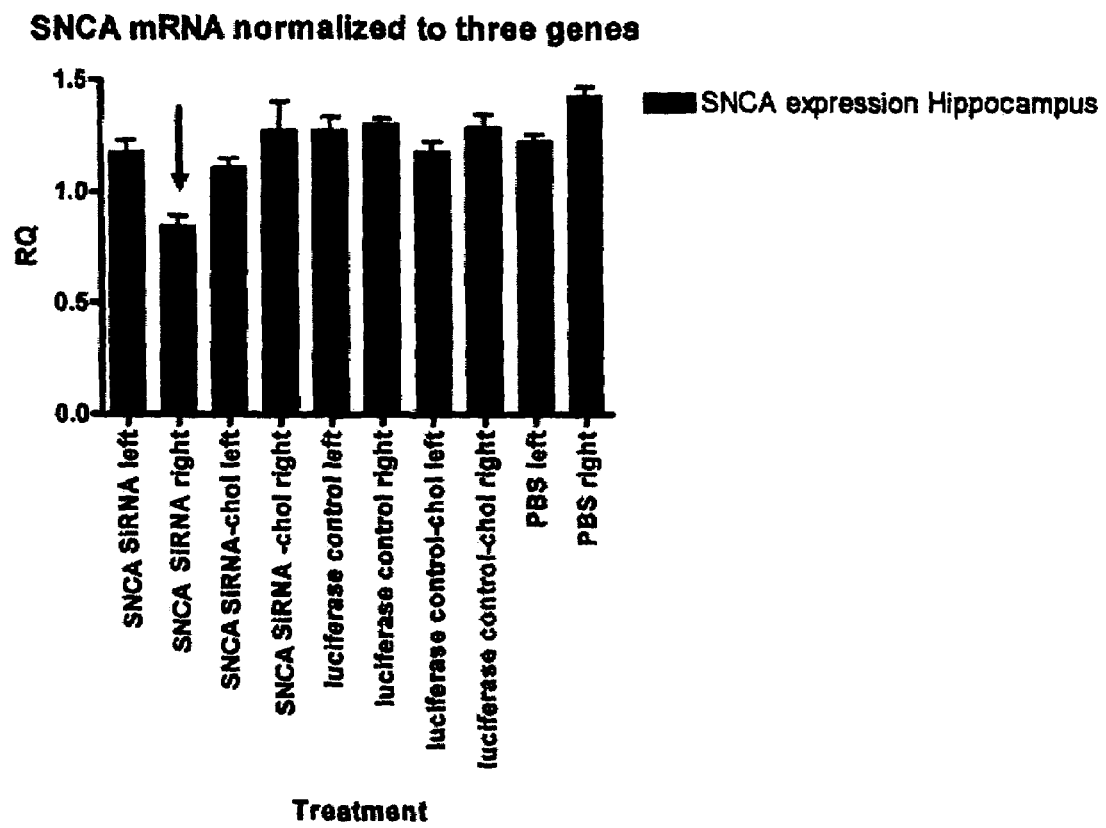
FIG. 13 is a graph showing silencing of endogenous alpha-synuclein by intraparenchymal infusion of siRNA.

A decrease of alpha-synuclein expression of approximately 30% (right vs left side) was measured in the animals infused with the SCNA siRNA. Statistical significance (p=0.036) was determined by T-test (FIG. 13).

Example 7

In situ Hybridization Showing Silencing of Endogenous α-synuclein by Intraparenchymal Infusion of siRNA Infusion cannulae were implanted into the hippocampus of eight-week old, female B6 mice (coordinates from bregma: x=(−)2.0, y=(−)1.5, z=2.0 calculated from Paxinos and Franklin, The Mouse Brain in Stereotaxic Coordinates). The cannulae were connected via catheters to osmotic mini-pumps (Alzet model 1002) containing approximately one hundred microliters of 2.1 mM siRNA solution in Phosphate Buffered Saline (PBS). The pumps were implanted subcutaneously. The infusion rate of 0.25 microliters per hour resulted in a dose of approximately 180 micrograms of siRNA per day. Infusion continued for a period of fifteen days. Treatment groups were: PBS (n=10), alpha-synuclein duplex (SNCA siRNA; n=9), luciferase control duplex (n=10). The sequences of the duplexes, as well as chemical modifications are shown below (Table 4).

TABLE 4

| siRNA | | Sequence |
|---|---|---|
| Luc control | S | 5' cuuAcGcuGAGuAcuucGATsT 3' (SEQ ID NO: 52) |
| | AS | 5' UCGAAGuACUcAGCGuAAGTsT 3' (SEQ ID NO: 53) |
| SNCA | S | 5' CsuAUGAGCCUGAAGCcuaATsT 3' (SEQ ID NO: 55) |
| | AS | 5' usuAGGCUUCAGGCUCAuAGTsT 3' (SEQ ID NO: 56) |

Key
A, C, G, U-ribonucleotides
c, u-2'-OMe nucleotides
s-phosphorothioate linkage
T-thymidine Following the infusion period, brains were dissected rapidly. To ensure sampling consistency, the brain was placed in a tissue matrix and the region anterior and posterior to the hippocampus was removed using a flat blade. The resulting three brain segments were snap frozen on dry ice and stored at −80° C. until use. Frozen sections were cut at 15 µm on a cryostat at −18° C. throughout the entire hippocampus and air dried for 20 minutes before freezing at −80° C. On the day of the experiment, frozen sections were removed on dry ice and dried quickly on a slide warmer at 55° C., then fixed in 4% paraformaldehyde in 0.1M Sorensen's Phosphate buffer for 20 minutes, washed twice in PBS and then dehydrated in ascending alcohols. Hybridization was then performed at 37° C. overnight, in a moist chamber, with approximately 0.02 ng of [α−$^{33}$P] dATP 3' end labeled probe per 1 µl of hybridization buffer (4×SSC, 1×Denhardt's solution, 50% (w/v) de-ionised formamide, 10% (w/v) dextran sulphate, 200 mg/µl herring sperm DNA). The probe (5'GGTCTTCTCAGCCACTGT-TGTCACTCCATGAACCAC'3) (SEQ ID NO: 58) was designed to exon 3 on mouse SNCA. Specific activity of the probe was >1×10$^8$ cpm/µg and after dilution in hybridization buffer corresponded to ~1×10$^4$ cpm/µl. Control hybridizations were also set up that contained a 50-fold molar excess of unlabelled probe to determine non-specific signal. Slides were washed in 1×SSC at room temperature (RT) to remove excess hybridization buffer; three times, each for 30 minutes, at 55° and at RT for 60 minutes. Slides were then dipped for 30 seconds in 70% (v/v) ethanol/300 mM ammonium acetate, then for 30 seconds in absolute alcohol, air dried and co-exposed with $^{14}$C microscale standards (Amersham) to Biomax MS film (Kodak) for 7-10 days.

The Metamorph software (Universal imaging) was used to perform densitometry. Specifically, optical density of mRNA labeled with the SNCA specific probe was measured in a standard square with and area of 240 pixels$^2$ in the cortex. Optical density was measured and values were compared to optical density of the known $^{14}$C standards. From these values and a graph was constructed and concentration of radioactivity in nCi/g in each sample was extrapolated. A t-test was used to determine if there was difference between groups.

Results

Figure 14:
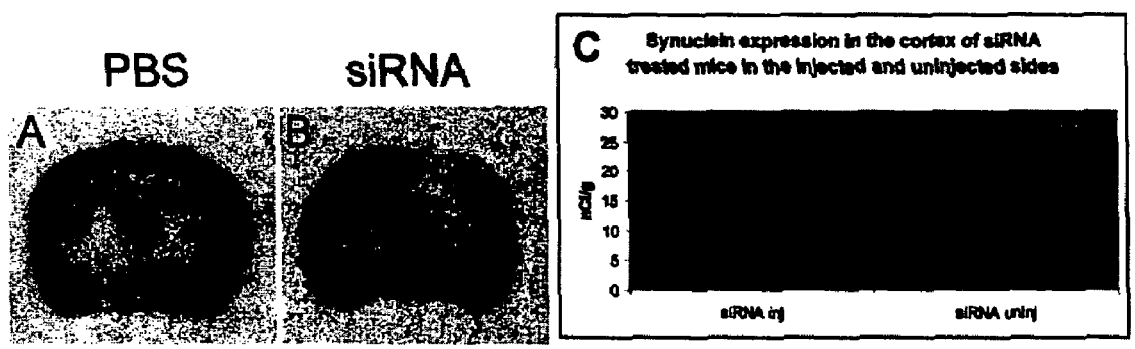
FIG. 14 shows synuclein expression in cortex of siRNA treated mice in the injected and non-injected sides of the brain.

There was a reduction in the expression of siRNA in the hippocampus and cortex in the injected side (right) compared uninjected side (left) of the siRNA treated animal (B). The PBS animal did not show a reduction in the injected side (A) in all the animals used in the in situ hybridization experiment (n=3). Densitometry analysis of the in situ hybridization film showed significant reduction (~60%) in SNCA mRNA expression in the injected side compared to the uninjected side (C) of the cortex (*p=0.003, t-test). Boxes in A and B show cortical region measured (FIG. 14).

Example 7

Method of Treating a Patient Diagnosed with a Synucleinopathy

A patient diagnosed with a synucleinopathy can be administered a pharmaceutical composition containing an iRNA agent that targets the SCNA gene. The composition can be delivered directly to the brain by a device that includes an osmotic pump and mini-cannula and is bilaterally implanted into the patient.

Prior to implantation of the device, the patient receives an MRI with stereotactic frame. A computer-guided trajectory is used for delivery of the cannula to the brain. The mini-pump device is implanted into the abdomen, and then the patient is hospitalized for 2-3 days to monitor for hemorrhaging.

Approximately two weeks post-implantation of the pump, the patient can receive an MRI to check the implanted device. If the human is healing well, and no complications have occurred as a result of implanting the device, then the anti-SNCA composition can be infused into the pump, and into the cannula. A test dose of the anti-SNCA agent can be administered prior to the initiation of the therapeutic regimen.

MRIs taken at 3 months, six months, and one year following the initial treatment can be used to monitor the condition of the device, and the reaction of the patient to the device and treatment with the iRNA agent. Clinicians should watch for the development of edema and an inflammatory response. Following the one-year anniversary of the initiation of the treatment, MRIs can be performed as needed.

The patient can be monitored for an improvement or stabilization in disease symptoms throughout the course of the therapy. Monitoring can include serial clinical assessments and functional neuroimaging, e.g., by MRI.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of inhibiting alpha-synuclein (SNCA) expression in a mammal comprising administering an iRNA agent directly to the brain of said mammal, wherein the iRNA agent comprises an antisense strand comprising SEQ ID NO: 22 and a sense strand comprising SEQ ID NO: 21, wherein each strand is 21-25 nucleotides in length.

2. The method of claim 1, further comprising a step of identifying a synucleinopathy in said mammal prior to the administering of said iRNA agent.

3. The method of claim 1, wherein said SNCA expression is reduced by at least 50% relative to expression in cells that had not been contacted by said iRNA agent.

4. The method of claim 2, wherein said mammal is a human.

5. The method of claim 1, wherein said iRNA agent is administered by stereotactic injection into the brain of said mammal.

6. The method of claim 1, wherein said iRNA agent is administered by intraparenchymal infusion or injection.

7. The method of claim 4, wherein said iRNA agent is administered by stereotactic injection into the brain of said human.

8. The method of claim 4, wherein said iRNA agent is administered by intraparenchymal infusion or injection.

9. The method of claim 1 or 4, further comprising a step of measuring SNCA expression in said mammal.

10. The method of claim 1 or 4, wherein said SNCA expression is measured before and after said administration of said iRNA agent.

11. The method of claim 1, wherein each strand of the iRNA agent is 21 nucleotides in length.

* * * * *

UNITED STATES PATENT AND TRADEMARK OFFICE
CERTIFICATE OF CORRECTION

| | | |
|---|---|---|
| PATENT NO. | : 7,595,306 B2 | Page 1 of 1 |
| APPLICATION NO. | : 11/548890 | |
| DATED | : September 29, 2009 | |
| INVENTOR(S) | : David Bumcrot | |

It is certified that error appears in the above-identified patent and that said Letters Patent is hereby corrected as shown below:

Title page item [73], please insert the Assignee information as follows: Alnylam Pharmaceuticals, Inc., Cambridge, MA (US).

Signed and Sealed this
Twenty-eighth Day of December, 2010

David J. Kappos
*Director of the United States Patent and Trademark Office*

SEQUENCE LISTING

<160> NUMBER OF SEQ ID NOS: 58

<210> SEQ ID NO 1
<211> LENGTH: 1543
<212> TYPE: DNA
<213> ORGANISM: Homo sapiens
<220> FEATURE:
<221> NAME/KEY: CDS
<222> LOCATION: (47)...(469)

<400> SEQUENCE: 1

```
ggagtggcca ttcgacgaca gtgtggtgta aaggaattca ttagcc atg gat gta        55
                                                   Met Asp Val
                                                     1 ttc atg aaa gga ctt tca aag gcc aag gag gga gtt gtg gct gct gct       103
Phe Met Lys Gly Leu Ser Lys Ala Lys Glu Gly Val Val Ala Ala Ala
      5                  10                  15 gag aaa acc aaa cag ggt gtg gca gaa gca gca gga aag aca aaa gag       151
Glu Lys Thr Lys Gln Gly Val Ala Glu Ala Ala Gly Lys Thr Lys Glu
 20                  25                  30                  35 ggt gtt ctc tat gta ggc tcc aaa acc aag gag gga gtg gtg cat ggt       199
Gly Val Leu Tyr Val Gly Ser Lys Thr Lys Glu Gly Val Val His Gly
                 40                  45                  50 gtg gca aca gtg gct gag aag acc aaa gag caa gtg aca aat gtt gga       247
Val Ala Thr Val Ala Glu Lys Thr Lys Glu Gln Val Thr Asn Val Gly
             55                  60                  65 gga gca gtg gtg acg ggt gtg aca gca gta gcc cag aag aca gtg gag       295
Gly Ala Val Val Thr Gly Val Thr Ala Val Ala Gln Lys Thr Val Glu
         70                  75                  80 gga gca ggg agc att gca gca gcc act ggc ttt gtc aaa aag gac cag       343
Gly Ala Gly Ser Ile Ala Ala Ala Thr Gly Phe Val Lys Lys Asp Gln
     85                  90                  95 ttg ggc aag aat gaa gaa gga gcc cca cag gaa gga att ctg gaa gat       391
Leu Gly Lys Asn Glu Glu Gly Ala Pro Gln Glu Gly Ile Leu Glu Asp
100                 105                 110                 115 atg cct gtg gat cct gac aat gag gct tat gaa atg cct tct gag gaa       439
Met Pro Val Asp Pro Asp Asn Glu Ala Tyr Glu Met Pro Ser Glu Glu
                120                 125                 130 ggg tat caa gac tac gaa cct gaa gcc taa gaaatatctt tgctcccagt         489
Gly Tyr Gln Asp Tyr Glu Pro Glu Ala *
                135                 140 ttcttgagat ctgctgacag atgttccatc ctgtacaagt gctcagttcc aatgtgccca     549
gtcatgacat ttctcaaagt ttttacagtg tatctcgaag tcttccatca gcagtgattg     609
aagtatctgt acctgccccc actcagcatt tcggtgcttc cctttcactg aagtgaatac     669
atggtagcag ggtctttgtg tgctgtggat tttgtggctt caatctacga tgttaaaaca     729
aattaaaaac acctaagtga ctaccactta tttctaaatc ctcactattt ttttgttgct     789
gttgttcaga agttgttagt gatttgctat catatattat aagattttta ggtgtctttt    849
aatgatactg tctaagaata atgacgtatt gtgaaatttg ttaatatata taatacttaa     909
aaatatgtga gcatgaaact atgcacctat aaatactaaa tatgaaattt taccattttg     969
cgatgtgttt tattcacttg tgtttgtata taatggtga gaattaaaat aaaacgttat     1029
ctcattgcaa aaatatttta tttttatccc atctcacttt aataataaaa atcatgctta    1089
taagcaacat gaattaagaa ctgacacaaa ggacaaaaat ataagttat taatagccat     1149 ttgaagaagg aggaatttta gaagaggtag agaaaatgga acattaaccc tacactcgga    1209
```

-continued

```
attccctgaa gcaacactgc cagaagtgtg ttttggtatg cactggttcc ttaagtggct    1269
gtgattaatt attgaaagtg gggtgttgaa gaccccaact actattgtag agtggtctat    1329
ttctcccttc aatcctgtca atgtttgctt tatgtatttt ggggaactgt tgtttgatgt    1389
gtatgtgttt ataattgtta tacatttta attgagcctt ttattaacat atattgttat     1449
ttttgtctcg aaataatttt ttagttaaaa tctattttgt ctgatattgg tgtgaatgct    1509
gtacctttct gacaataaat aatattcgac catg                                1543
```

```
<210> SEQ ID NO 2
<211> LENGTH: 140
<212> TYPE: PRT
<213> ORGANISM: Homo sapiens

<400> SEQUENCE: 2
```

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

```
<210> SEQ ID NO 3
<211> LENGTH: 21
<212> TYPE: RNA
<213> ORGANISM: Artificial Sequence
<220> FEATURE:
<223> OTHER INFORMATION: Primer

<400> SEQUENCE: 3
gguguggcaa caguggcuga g                                              21

<210> SEQ ID NO 4
<211> LENGTH: 23
<212> TYPE: RNA
<213> ORGANISM: Artificial Sequence
<220> FEATURE:
<223> OTHER INFORMATION: Primer

<400> SEQUENCE: 4
cucagccacu guugccacac cau                                            23

<210> SEQ ID NO 5
<211> LENGTH: 21
<212> TYPE: RNA
<213> ORGANISM: Artificial Sequence
<220> FEATURE:
<223> OTHER INFORMATION: Primer
```

```
<400> SEQUENCE: 5
aacaguggcu gagaagacca a                                                21

<210> SEQ ID NO 6
<211> LENGTH: 23
<212> TYPE: RNA
<213> ORGANISM: Artificial Sequence
<220> FEATURE:
<223> OTHER INFORMATION: Primer

<400> SEQUENCE: 6 uuggcuucu cagccacugu ugc                                               23

<210> SEQ ID NO 7
<211> LENGTH: 21
<212> TYPE: RNA
<213> ORGANISM: Artificial Sequence
<220> FEATURE:
<223> OTHER INFORMATION: Primer

<400> SEQUENCE: 7
auugcagcag ccacuggcuu u                                                21

<210> SEQ ID NO 8
<211> LENGTH: 23
<212> TYPE: RNA
<213> ORGANISM: Artificial Sequence
<220> FEATURE:
<223> OTHER INFORMATION: Primer

<400> SEQUENCE: 8
aaagccagug gcugcugcaa ugc                                              23

<210> SEQ ID NO 9
<211> LENGTH: 21
<212> TYPE: RNA
<213> ORGANISM: Artificial Sequence
<220> FEATURE:
<223> OTHER INFORMATION: Primer

<400> SEQUENCE: 9
aagugacaaa uguuggagga g                                                21

<210> SEQ ID NO 10
<211> LENGTH: 23
<212> TYPE: RNA
<213> ORGANISM: Artificial Sequence
<220> FEATURE:
<223> OTHER INFORMATION: Primer

<400> SEQUENCE: 10
caccuccaac auuugucacu ugc                                              23

<210> SEQ ID NO 11
<211> LENGTH: 21
<212> TYPE: RNA
<213> ORGANISM: Artificial Sequence
<220> FEATURE:
<223> OTHER INFORMATION: Primer

<400> SEQUENCE: 11
gaagaaggag ccccacagga a                                                21

<210> SEQ ID NO 12
<211> LENGTH: 23
```

```
<212> TYPE: RNA
<213> ORGANISM: Artificial Sequence
<220> FEATURE:
<223> OTHER INFORMATION: Primer

<400> SEQUENCE: 12
uuccuguggg gcuccuucuu cau                                               23

<210> SEQ ID NO 13
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 13 cggguguguac agcaguagcn n                                                21

<210> SEQ ID NO 14
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 14
gcuacugcug ucacacccgn n                                                 21

<210> SEQ ID NO 15
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 15
uccugacaau gaggcuuaun n                                                 21

<210> SEQ ID NO 16
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 16
auaagccuca uugucaggan n                                                 21

<210> SEQ ID NO 17
<211> LENGTH: 21
<212> TYPE: DNA
<213> ORGANISM: Artificial Sequence
<220> FEATURE:
```

```
<223> OTHER INFORMATION: Primer
<220> FEATURE:
<221> NAME/KEY: misc_feature
<222> LOCATION: 1
<223> OTHER INFORMATION: n = uridine phosphorothioate modification
<220> FEATURE:
<221> NAME/KEY: modified_base
<222> LOCATION: 16, 17
<223> OTHER INFORMATION: / 2'-O-Me-uridine modification
<220> FEATURE:
<221> NAME/KEY: misc_feature
<222> LOCATION: 20, 21
<223> OTHER INFORMATION: n = dT= deoxythymidine

<400> SEQUENCE: 17
nccugacaau gaggcuuaun n                                              21

<210> SEQ ID NO 18
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 2
<223> OTHER INFORMATION: / 2'-O-Me-uridine phosphorothioate modification
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine phosphorothioate
      modification

<400> SEQUENCE: 18
auaagccuca uugucaggan n                                              21

<210> SEQ ID NO 19
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 19
cuacgaaccu gaagccuaan n                                              21

<210> SEQ ID NO 20
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 20
uuaggcuuca gguucguagn n                                              21

<210> SEQ ID NO 21
<211> LENGTH: 21
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: 1
<223> OTHER INFORMATION: n = cytosine phosphorothioate modification
<220> FEATURE:
<221> NAME/KEY: modified_base
<222> LOCATION: 16
<223> OTHER INFORMATION: / 2'-O-Me-cytosine modification
<220> FEATURE:
<221> NAME/KEY: modified_base
<222> LOCATION: 17
<223> OTHER INFORMATION: / 2'-O-Me -uridine modification
<220> FEATURE:
<221> NAME/KEY: modified_base
<222> LOCATION: 18
<223> OTHER INFORMATION: / 2'-O-Me-adenine modification
<220> FEATURE:
<221> NAME/KEY: misc_feature
<222> LOCATION: 20
<223> OTHER INFORMATION: / deoxythymidine phosphorothioate modification
<220> FEATURE:
<221> NAME/KEY: misc_feature
<222> LOCATION: 21
<223> OTHER INFORMATION: n = dT= deoxythymidine

<400> SEQUENCE: 21
nuacgaaccu gaagccuaan n                                          21

<210> SEQ ID NO 22
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 1
<223> OTHER INFORMATION: / 2'-O-Me-uridine modification
<220> FEATURE:
<221> NAME/KEY: modified_base
<222> LOCATION: 2
<223> OTHER INFORMATION: / 2'-O-Me-uridine phosphorothioate modification
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
<222> LOCATION: 21
<223> OTHER INFORMATION: n = deoxythymidine phosphorothioate
      modification

<400> SEQUENCE: 22
uuaggcuuca gguucguagn n                                          21

<210> SEQ ID NO 23
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 1
<223> OTHER INFORMATION: / cytosine phosphorothioate modification
<220> FEATURE:
<221> NAME/KEY: modified_base
<222> LOCATION: 2, 17
<223> OTHER INFORMATION: / 2'-O-Me-uridine modification
<220> FEATURE:
<221> NAME/KEY: modified_base
<222> LOCATION: 16
```

```
<223> OTHER INFORMATION: / 2'-O-Me-cytosine modification
<220> FEATURE:
<221> NAME/KEY: modified_base
<222> LOCATION: 18
<223> OTHER INFORMATION: / 2'-O-Me-adenine modification
<220> FEATURE:
<221> NAME/KEY: misc_feature
<222> LOCATION: 20
<223> OTHER INFORMATION: n = deoxythymidine phosphorothioate
      modification
<220> FEATURE:
<221> NAME/KEY: misc_feature
<222> LOCATION: 21
<223> OTHER INFORMATION: n = dT= deoxythymidine

<400> SEQUENCE: 23
cuacgaaccu gaagccuaan n                                              21

<210> SEQ ID NO 24
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 1, 17
<223> OTHER INFORMATION: / 2'-O-Me-uridine modification
<220> FEATURE:
<221> NAME/KEY: modified_base
<222> LOCATION: 2
<223> OTHER INFORMATION: / 2'-O-Me-uridine phosphorothioate modification
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
<222> LOCATION: 21
<223> OTHER INFORMATION: n = deoxythymidine phosphorothioate
      modification

<400> SEQUENCE: 24
uuaggcuuca gguucguagn n                                              21

<210> SEQ ID NO 25
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 25
cuauuguaga guggucuaun n                                              21

<210> SEQ ID NO 26
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 26
auagaccacu cuacaauagn n                                              21
```

<210> SEQ ID NO 27
<211> LENGTH: 21
<212> TYPE: RNA
<213> ORGANISM: Artificial Sequence
<220> FEATURE:
<223> OTHER INFORMATION: Primer

<400> SEQUENCE: 27
gaacugugug ugagaggucc u                                                  21

<210> SEQ ID NO 28
<211> LENGTH: 23
<212> TYPE: RNA
<213> ORGANISM: Artificial Sequence
<220> FEATURE:
<223> OTHER INFORMATION: Primer
<220> FEATURE:
<221> NAME/KEY: modified_base
<222> LOCATION: 22, 23
<223> OTHER INFORMATION: / 2'-O-Me-cytosine phosphorothioate
      modification

<400> SEQUENCE: 28
aggaccucuc acacacaguu ccc                                                23

<210> SEQ ID NO 29
<211> LENGTH: 21
<212> TYPE: RNA
<213> ORGANISM: Artificial Sequence
<220> FEATURE:
<223> OTHER INFORMATION: Primer

<400> SEQUENCE: 29
gacguaaacg gccacaaguu c                                                  21

<210> SEQ ID NO 30
<211> LENGTH: 21
<212> TYPE: RNA
<213> ORGANISM: Artificial Sequence
<220> FEATURE:
<223> OTHER INFORMATION: Primer

<400> SEQUENCE: 30
acuuguggcc guuuacgucg c                                                  21

<210> SEQ ID NO 31
<211> LENGTH: 16
<212> TYPE: PRT
<213> ORGANISM: Artificial Sequence
<220> FEATURE:
<223> OTHER INFORMATION: Exemplary Cell Permeation Peptide

<400> SEQUENCE: 31

Arg Gln Ile Lys Ile Trp Phe Gln Asn Arg Arg Met Lys Trp Lys Lys
 1               5                  10                  15

<210> SEQ ID NO 32
<211> LENGTH: 14
<212> TYPE: PRT
<213> ORGANISM: Artificial Sequence
<220> FEATURE:
<223> OTHER INFORMATION: Exemplary Cell Permeation Peptide

<400> SEQUENCE: 32

Gly Arg Lys Lys Arg Arg Gln Arg Arg Arg Pro Pro Gln Cys
 1               5                  10

```
<210> SEQ ID NO 33
<211> LENGTH: 27
<212> TYPE: PRT
<213> ORGANISM: Artificial Sequence
<220> FEATURE:
<223> OTHER INFORMATION: Exemplary Cell Permeation Peptide

<400> SEQUENCE: 33

Gly Ala Leu Phe Leu Gly Trp Leu Gly Ala Ala Gly Ser Thr Met Gly
 1               5                  10                  15

Ala Trp Ser Gln Pro Lys Lys Lys Arg Lys Val
             20                  25

<210> SEQ ID NO 34
<211> LENGTH: 18
<212> TYPE: PRT
<213> ORGANISM: Artificial Sequence
<220> FEATURE:
<223> OTHER INFORMATION: Exemplary Cell Permeation Peptide

<400> SEQUENCE: 34

Leu Leu Ile Ile Leu Arg Arg Arg Ile Arg Lys Gln Ala His Ala His
 1               5                  10                  15

Ser Lys

<210> SEQ ID NO 35
<211> LENGTH: 26
<212> TYPE: PRT
<213> ORGANISM: Artificial Sequence
<220> FEATURE:
<223> OTHER INFORMATION: Exemplary Cell Permeation Peptide

<400> SEQUENCE: 35

Gly Trp Thr Leu Asn Ser Ala Gly Tyr Leu Leu Lys Ile Asn Leu Lys
 1               5                  10                  15

Ala Leu Ala Ala Leu Ala Lys Lys Ile Leu
             20                  25

<210> SEQ ID NO 36
<211> LENGTH: 18
<212> TYPE: PRT
<213> ORGANISM: Artificial Sequence
<220> FEATURE:
<223> OTHER INFORMATION: Exemplary Cell Permeation Peptide

<400> SEQUENCE: 36

Lys Leu Ala Leu Lys Leu Ala Leu Lys Ala Leu Lys Ala Ala Leu Lys
 1               5                  10                  15

Leu Ala

<210> SEQ ID NO 37
<211> LENGTH: 9
<212> TYPE: PRT
<213> ORGANISM: Artificial Sequence
<220> FEATURE:
<223> OTHER INFORMATION: Exemplary Cell Permeation Peptide

<400> SEQUENCE: 37

Arg Arg Arg Arg Arg Arg Arg Arg
 1               5

<210> SEQ ID NO 38
<211> LENGTH: 10
```

```
<212> TYPE: PRT
<213> ORGANISM: Artificial Sequence
<220> FEATURE:
<223> OTHER INFORMATION: Exemplary Cell Permeation Peptide

<400> SEQUENCE: 38

Lys Phe Phe Lys Phe Phe Lys Phe Phe Lys
 1               5                  10

<210> SEQ ID NO 39
<211> LENGTH: 37
<212> TYPE: PRT
<213> ORGANISM: Artificial Sequence
<220> FEATURE:
<223> OTHER INFORMATION: Exemplary Cell Permeation Peptide

<400> SEQUENCE: 39

Leu Leu Gly Asp Phe Phe Arg Lys Ser Lys Glu Lys Ile Gly Lys Glu
 1               5                  10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 40
<211> LENGTH: 31
<212> TYPE: PRT
<213> ORGANISM: Artificial Sequence
<220> FEATURE:
<223> OTHER INFORMATION: Exemplary Cell Permeation Peptide

<400> SEQUENCE: 40

Ser Trp Leu Ser Lys Thr Ala Lys Lys Leu Glu Asn Ser Ala Lys Lys
 1               5                  10                  15

Arg Ile Ser Glu Gly Ile Ala Ile Ala Ile Gln Gly Gly Pro Arg
                20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Exemplary Cell Permeation Peptide

<400> SEQUENCE: 41

Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
                20                  25                  30

<210> SEQ ID NO 42
<211> LENGTH: 36
<212> TYPE: PRT
<213> ORGANISM: Artificial Sequence
<220> FEATURE:
<223> OTHER INFORMATION: Exemplary Cell Permeation Peptide

<400> SEQUENCE: 42

Asp His Tyr Asn Cys Val Ser Ser Gly Gly Gln Cys Leu Tyr Ser Ala
 1               5                  10                  15

Cys Pro Ile Phe Thr Lys Ile Gln Gly Thr Cys Tyr Arg Gly Lys Ala
                20                  25                  30

Lys Cys Cys Lys
            35
```

<210> SEQ ID NO 43
<211> LENGTH: 12
<212> TYPE: PRT
<213> ORGANISM: Artificial Sequence
<220> FEATURE:
<223> OTHER INFORMATION: Exemplary Cell Permeation Peptide

<400> SEQUENCE: 43

Arg Lys Cys Arg Ile Val Val Ile Arg Val Cys Arg
1               5                   10

<210> SEQ ID NO 44
<211> LENGTH: 42
<212> TYPE: PRT
<213> ORGANISM: Artificial Sequence
<220> FEATURE:
<223> OTHER INFORMATION: Exemplary Cell Permeation Peptide

<400> SEQUENCE: 44

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 45
<211> LENGTH: 13
<212> TYPE: PRT
<213> ORGANISM: Artificial Sequence
<220> FEATURE:
<223> OTHER INFORMATION: Exemplary Cell Permeation Peptide

<400> SEQUENCE: 45

Ile Leu Pro Trp Lys Trp Pro Trp Trp Pro Trp Arg Arg
1               5                   10

<210> SEQ ID NO 46
<211> LENGTH: 16
<212> TYPE: PRT
<213> ORGANISM: Artificial Sequence
<220> FEATURE:
<223> OTHER INFORMATION: An exemplary hydrophobic peptide

<400> SEQUENCE: 46

Ala Ala Val Ala Leu Leu Pro Ala Val Leu Leu Ala Leu Leu Ala Pro
1               5                   10                  15

<210> SEQ ID NO 47
<211> LENGTH: 11
<212> TYPE: PRT
<213> ORGANISM: Artificial Sequence
<220> FEATURE:
<223> OTHER INFORMATION: An exemplary hydrophobic peptide

<400> SEQUENCE: 47

Ala Ala Leu Leu Pro Val Leu Leu Ala Ala Pro
1               5                   10

<210> SEQ ID NO 48
<211> LENGTH: 13
<212> TYPE: PRT
<213> ORGANISM: Human immunodeficiency virus

<400> SEQUENCE: 48

```
Gly Arg Lys Lys Arg Arg Gln Arg Arg Pro Pro Gln
  1               5                  10
```

<210> SEQ ID NO 49
<211> LENGTH: 16
<212> TYPE: PRT
<213> ORGANISM: Drosophila Antennapedia

<400> SEQUENCE: 49

```
Arg Gln Ile Lys Ile Trp Phe Gln Asn Arg Arg Met Lys Trp Lys Lys
  1               5                  10                  15
```

<210> SEQ ID NO 50
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1
<223> OTHER INFORMATION: n = cytosine phosphorothioate modification
<220> FEATURE:
<221> NAME/KEY: modified_base
<222> LOCATION: 2, 17
<223> OTHER INFORMATION: n = 2'-O-Me-uridine modification
<220> FEATURE:
<221> NAME/KEY: modified_base
<222> LOCATION: 16
<223> OTHER INFORMATION: / 2'-O-Me-cytosine modification
<220> FEATURE:
<221> NAME/KEY: modified_base
<222> LOCATION: 18
<223> OTHER INFORMATION: n = 2'-O-Me-adenine modification
<220> FEATURE:
<221> NAME/KEY: misc_feature
<222> LOCATION: 20
<223> OTHER INFORMATION: n = deoxythymidine phosphorothioate
      modification
<220> FEATURE:
<221> NAME/KEY: misc_feature
<222> LOCATION: 21
<223> OTHER INFORMATION: n = deoxythymidine

<400> SEQUENCE: 50
nuaugagccu gaagccuaan n                                           21

<210> SEQ ID NO 51
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: 1, 17
<223> OTHER INFORMATION: / 2'-O-Me-uridine modification
<220> FEATURE:
<221> NAME/KEY: modified_base
<222> LOCATION: 2
<223> OTHER INFORMATION: / 2'-O-Me-uridine phosphorothioate modification
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine phosphorothioate
      modification
<220> FEATURE:
<221> NAME/KEY: misc_feature
<222> LOCATION: 2

```
<223> OTHER INFORMATION: n = 2'-O-Me-uridine modification

<400> SEQUENCE: 51
uuaggcuuca ggcucauagn n                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 1, 5, 7, 14, 17
<223> OTHER INFORMATION: / 2'-O-Me-cytosine modification
<220> FEATURE:
<221> NAME/KEY: modified_base
<222> LOCATION: 2, 3, 8, 12, 15, 16
<223> OTHER INFORMATION: /2'-O-Me-uridine modification
<220> FEATURE:
<221> NAME/KEY: misc_feature
<222> LOCATION: 20
<223> OTHER INFORMATION: n = deoxythymidine phosphorothioate
      modification

<400> SEQUENCE: 52
cuuacgcuga guacuucgan t                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 7, 16
<223> OTHER INFORMATION: /2'-O-Me-uridine modification
<220> FEATURE:
<221> NAME/KEY: modified_base
<222> LOCATION: 11
<223> OTHER INFORMATION: / 2'-O-Me-cytosine modification
<220> FEATURE:
<221> NAME/KEY: misc_feature
<222> LOCATION: 20
<223> OTHER INFORMATION: n = deoxythymidine phosphorothioate
      modification

<400> SEQUENCE: 53
ucgaaguacu cagcguaagn t                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 1, 5, 7, 14, 17
<223> OTHER INFORMATION: / 2'-O-Me-cytosine modification
<220> FEATURE:
<221> NAME/KEY: modified_base
<222> LOCATION: 2, 3, 8, 12, 15, 16
<223> OTHER INFORMATION: /2'-O-Me-uridine modification
<220> FEATURE:
<221> NAME/KEY: misc_feature
<222> LOCATION: 20
<223> OTHER INFORMATION: n = deoxythymidine phosphorothioate
      modification
<220> FEATURE:
<221> NAME/KEY: misc_feature
<222> LOCATION: 21
```

<223> OTHER INFORMATION: n = deoxythymidine phosphorothioate
      modification conjugated cholesterol

<400> SEQUENCE: 54
cuuacgcuga guacuucgan n                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytosine deoxythymidine phosphorothioate
      modification
<220> FEATURE:
<221> NAME/KEY: modified_base
<222> LOCATION: 2, 17
<223> OTHER INFORMATION: /2'-O-Me-uridine modification
<220> FEATURE:
<221> NAME/KEY: modified_base
<222> LOCATION: 16
<223> OTHER INFORMATION: / 2'-O-Me-cytosine modification
<220> FEATURE:
<221> NAME/KEY: modified_base
<222> LOCATION: 18
<223> OTHER INFORMATION: / 2'-O-Me-adenine modification
<220> FEATURE:
<221> NAME/KEY: misc_feature
<222> LOCATION: 20
<223> OTHER INFORMATION: n = deoxythymidine phosphorothioate
      modification

<400> SEQUENCE: 55
nuaugagccu gaagccuaan t                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = uridine phosphorothioate
      modification
<220> FEATURE:
<221> NAME/KEY: modified_base
<222> LOCATION: 2, 17
<223> OTHER INFORMATION: /2'-O-Me-uridine modification
<220> FEATURE:
<221> NAME/KEY: misc_feature
<222> LOCATION: 20
<223> OTHER INFORMATION: n = deoxythymidine phosphorothioate
      modification

<400> SEQUENCE: 56
nuaggcuuca ggcucauagn t                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytosine deoxythymidine phosphorothioate
      modification

```
<220> FEATURE:
<221> NAME/KEY: modified_base
<222> LOCATION: 2, 17
<223> OTHER INFORMATION: /2'-O-Me-uridine modification
<220> FEATURE:
<221> NAME/KEY: modified_base
<222> LOCATION: 16
<223> OTHER INFORMATION: / 2'-O-Me-cytosine modification
<220> FEATURE:
<221> NAME/KEY: modified_base
<222> LOCATION: 18
<223> OTHER INFORMATION: / 2'-O-Me-adenine modification
<220> FEATURE:
<221> NAME/KEY: misc_feature
<222> LOCATION: 20
<223> OTHER INFORMATION: n = deoxythymidine phosphorothioate
      modification
<220> FEATURE:
<221> NAME/KEY: modified_base
<222> LOCATION: 21
<223> OTHER INFORMATION: / conjugated cholesterol

<400> SEQUENCE: 57
nuaugagccu gaagccuaan t                                                    21

<210> SEQ ID NO 58
<211> LENGTH: 36
<212> TYPE: DNA
<213> ORGANISM: Artificial Sequence
<220> FEATURE:
<223> OTHER INFORMATION: Synthetically generated oligonucleotide

<400> SEQUENCE: 58
ggtcttctca gccactgttg tcactccatg aaccac                                    36
```